United States Patent
Kulstad et al.

(10) Patent No.: US 12,115,027 B2
(45) Date of Patent: Oct. 15, 2024

(54) ESOPHAGEAL HEAT TRANSFER DEVICES AND METHODS FOR CARDIAC TISSUE ABLATION

(71) Applicant: Advanced Cooling Therapy, Inc., Chicago, IL (US)

(72) Inventors: Erik Kulstad, Chicago, IL (US); Jay D. Schieber, Chicago, IL (US)

(73) Assignee: Advanced Cooling Therapy, Inc., Chicago, IL (US)

( * ) Notice: Subject to any disclaimer, the term of this patent is extended or adjusted under 35 U.S.C. 154(b) by 873 days.

(21) Appl. No.: 17/044,907

(22) PCT Filed: Apr. 3, 2019

(86) PCT No.: PCT/US2019/025475
§ 371 (c)(1),
(2) Date: Oct. 2, 2020

(87) PCT Pub. No.: WO2019/195354
PCT Pub. Date: Oct. 10, 2019

(65) Prior Publication Data
US 2021/0145534 A1   May 20, 2021

Related U.S. Application Data

(60) Provisional application No. 62/795,916, filed on Jan. 23, 2019, provisional application No. 62/793,998, (Continued)

(51) Int. Cl.
*A61B 34/20* (2016.01)
*A61B 18/14* (2006.01)
(Continued)

(52) U.S. Cl.
CPC .......... *A61B 90/04* (2016.02); *A61B 18/1492* (2013.01); *A61B 34/20* (2016.02);
(Continued)

(58) Field of Classification Search
CPC ..... A61B 90/04; A61B 34/20; A61B 18/1492; A61B 2034/2051; A61B 2034/2063;
(Continued)

(56) References Cited

U.S. PATENT DOCUMENTS

| | | |
|---|---|---|
| 6,264,679 B1 | 7/2001 | Keller et al. |
| 9,352,174 B2 | 5/2016 | Sliwa |

(Continued)

FOREIGN PATENT DOCUMENTS

| | | |
|---|---|---|
| CN | 102106753 A | 6/2011 |
| CN | 104023663 A | 9/2014 |

(Continued)

OTHER PUBLICATIONS

The United States Patent and Trademark Office, International Search Report in International Application No. PCT/US2019/025475.

(Continued)

*Primary Examiner* — Ankit D Tejani
*Assistant Examiner* — Joshua Brendon Solomon
(74) *Attorney, Agent, or Firm* — Nutter McClennen & Fish LLP

(57) ABSTRACT

Method and apparatus are disclosed for esophageal heat transfer devices and methods for cardiac tissue ablation procedures. An exemplary method includes collecting esophageal data via one or more sensing elements of an esophageal heat transfer device positioned within an esophagus of the patient. The exemplary method includes determining, based on the esophageal data and/or operator selected power setting, a temperature setting and/or a flow rate setting for fluid flowing through the esophageal heat transfer device to maintain a target temperature of esophageal tissue adjacent to the ablation site via a heat transfer region. The exemplary method includes adjusting, via the controller, a fluid source to provide the fluid to the esopha- (Continued)

geal heat transfer device at the temperature setting and/or a flow rate setting.

15 Claims, 21 Drawing Sheets

Related U.S. Application Data filed on Jan. 18, 2019, provisional application No. 62/739,595, filed on Oct. 1, 2018, provisional application No. 62/652,641, filed on Apr. 4, 2018.

(51) Int. Cl.
*A61B 90/00* (2016.01)
*A61B 18/00* (2006.01)
*A61B 18/02* (2006.01)

(52) U.S. Cl.
CPC ............... A61B 2018/00023 (2013.01); A61B 2018/0022 (2013.01); A61B 2018/00351 (2013.01); A61B 2018/00488 (2013.01); A61B 2018/00577 (2013.01); A61B 2018/00714 (2013.01); A61B 2018/00744 (2013.01); A61B 2018/00791 (2013.01); A61B 2018/00982 (2013.01); A61B 2018/0212 (2013.01); A61B 2034/2051 (2016.02); A61B 2034/2063 (2016.02); A61B 2090/0418 (2016.02); A61B 2090/0463 (2016.02); A61B 2090/0481 (2016.02); A61B 2090/065 (2016.02)

(58) Field of Classification Search
CPC .... A61B 2090/0418; A61B 2090/0463; A61B 2090/0481; A61B 2090/065; A61B 2018/00023; A61B 2018/0022; A61B 2018/00351; A61B 2018/00488; A61B 2018/00577; A61B 2018/00714; A61B 2018/00744; A61B 2018/00791; A61B 2018/00982; A61B 2018/0212; A61F 7/123

See application file for complete search history.

(56) References Cited

U.S. PATENT DOCUMENTS

| | | | |
|---|---|---|---|
| 10,363,162 B2 | 7/2019 | Kulstad et al. | |
| 2001/0044644 A1 | 11/2001 | Keller et al. | |
| 2001/0047133 A1 | 11/2001 | Gilboa et al. | |
| 2002/0065455 A1 | 5/2002 | Ben-Haim et al. | |
| 2004/0210281 A1 | 10/2004 | Dzeng et al. | |
| 2005/0187545 A1 | 8/2005 | Hooven et al. | |
| 2005/0222652 A1 | 10/2005 | Mori | |
| 2007/0055328 A1 | 3/2007 | Mayse et al. | |
| 2008/0039746 A1* | 2/2008 | Hissong | A61N 7/02 601/3 |
| 2008/0077126 A1 | 3/2008 | Rashidi | |
| 2008/0161890 A1 | 7/2008 | Lafontaine | |
| 2008/0243112 A1 | 10/2008 | De Neve | |
| 2009/0069875 A1 | 3/2009 | Fishel | |
| 2010/0152590 A1* | 6/2010 | Moore | A61B 8/4461 600/466 |
| 2010/0168624 A1 | 7/2010 | Sliwa | |
| 2011/0152856 A1 | 6/2011 | Govari et al. | |
| 2012/0035603 A1 | 2/2012 | Lenihan | |
| 2012/0172703 A1 | 7/2012 | Esguerra et al. | |
| 2012/0265172 A1 | 10/2012 | Kulstad et al. | |
| 2013/0296983 A1 | 7/2013 | Keller et al. | |
| 2013/0211283 A1* | 8/2013 | Bunch | A61B 5/6853 600/549 |
| 2014/0155965 A1 | 6/2014 | Kulstad et al. | |
| 2014/0364848 A1 | 12/2014 | Heimbecher et al. | |
| 2015/0282858 A1 | 10/2015 | Baust et al. | |
| 2016/0235339 A1 | 8/2016 | Bar-Tal et al. | |
| 2016/0278845 A1 | 9/2016 | Mayse | |
| 2017/0014181 A1 | 1/2017 | Bar-Tal et al. | |
| 2017/0086919 A1 | 3/2017 | Calabro et al. | |
| 2018/0161097 A1* | 6/2018 | Zoabi | G06T 7/11 |

FOREIGN PATENT DOCUMENTS

| | | |
|---|---|---|
| CN | 105877743 A | 8/2016 |
| JP | 2004-283606 A | 10/2004 |
| JP | 2005-128035 A | 5/2005 |
| JP | 2007-167127 A | 7/2007 |
| JP | 2009-504284 A | 2/2009 |
| JP | 2010-088914 A | 4/2010 |
| JP | 2010-207619 A | 9/2010 |
| JP | 2012-80996 A | 4/2012 |
| JP | 2012-139502 A | 7/2012 |
| JP | 2015-047226 A | 3/2015 |
| WO | 1997048438 A2 | 12/1997 |
| WO | 2007010073 A2 | 1/2007 |
| WO | 2013130655 A1 | 9/2013 |
| WO | 2015063246 A1 | 5/2015 |

OTHER PUBLICATIONS

The United States Patent and Trademark Office, Written Opinion in International Application No. PCT/US2019/025475.
The European Patent Office, Supplementary European Search Report in European Application No. 19781556.6, Dec. 10, 2021 (6 pages).
Arruda MS, et al., Feasibility and safety of using an esophageal protective system to eliminate esophageal thermal injury: implications on atrial-esophageal fistula following AF ablation. Journal of Cardiovascular Electrophysiology 2009, 20(11):1272-1278.
Berjano EJ, et al., A cooled intraesophageal balloon to prevent thermal injury during endocardial surgical radiofrequency ablation of the left atrium: a finite element study. Physics in Medicine and Biology 2005, 50(20):N269-279.
Carroll BJ, et al., Multi-sensor esophageal temperature probe used during radiofrequency ablation for atrial fibrillation is associated with increased intraluminal temperature detection and increased risk of esophageal injury compared to single-sensor probe. J Cardiovasc Electrophysiol 2013, 24(9):958-964.
Das, M et al., Ablation index, a novel marker of ablation lesion quality: prediction of pulmonary vein reconnection at repeat electrophysiology study and regional differences in target values, Europace 2017, 19:775-583.
Good E, et al., Movement of the esophagus during left atrial catheter ablation for atrial fibrillation. J Am Coll Cardiol 2005, 46(11):2107-2110.
John J, et al., The effect of esophageal cooling on esophageal injury during radiofrequency catheter ablation of atrial fibrillation. J Interv Card Electrophysiol 2019, 58(1):43-50.
Kadado AJ, et al., Luminal esophageal temperature monitoring to reduce esophageal thermal injury during catheter ablation for atrial fibrillation: A review. Trends in Cardiovascular Medicine 2019, 29(5):264-271.
Kuwahara T, et al., Oesophageal cooling with ice water does not reduce the incidence of oesophageal lesions complicating catheter ablation of atrial fibrillation: randomized controlled study. Europace 2014, 16(6):834-839.
Lequerica JL, et al., A cooled water-irrigated intraesophageal balloon to prevent thermal injury during cardiac ablation: experimental study based on an agar phantom. Physics in Medicine and Biology 2008, 53(4):N25-34.
Lequerica JL, et al., Reliability assessment of a cooled intraesophageal balloon to prevent thermal injury during RF cardiac ablation: an agar phantom study. Journal of Cardiovascular Electrophysiology 2008, 19(11):1188-1193.
Leung LW, et al., Esophageal cooling for protection during left atrial ablation: a systematic review and meta-analysis. J Interv Card Electrophysiol 2019, 59(2):347-355.
Muller P, et al., Higher incidence of esophageal lesions after ablation of atrial fibrillation related to the use of esophageal temperature probes. Heart Rhythm 2015, 12(7):1464-1469.

(56) References Cited

OTHER PUBLICATIONS

Pappone C, et al., Atrio-esophageal fistula as a complication of percutaneous transcatheter ablation of atrial fibrillation. Circulation 2004, 109(22):2724-2726.
Scanavacca MI, et al., Cooled intra-esophageal balloon to prevent thermal injury of esophageal wall during radiofrequency ablation. In: European Society of Cardiology Congress Sep. 1-5, 2007: Sep. 1-5, 2007; Vienna, Austria; 2007: 156 (165?).
Sohara H, et al., Prevalence of esophageal ulceration after atrial fibrillation ablation with the hot balloon ablation catheter: what is the value of esophageal cooling? Journal of Cardiovascular Electrophysiology 2014, 25(7):686-692.
Tschabrunn CM, et al., Comparison between single- and multi-sensor oesophageal temperature probes during atrial fibrillation ablation: thermodynamic characteristics. Europace 2015, 17(6):891-897.
Tsuchiya T, et al., Atrial fibrillation ablation with esophageal cooling with a cooled water-irrigated intraesophageal balloon: a pilot study. Journal of Cardiovascular Electrophysiology 2007, 18(2):145-150.
English Translation of Official Action in corresponding Japanese patent application No. 503702/2021 (PCT/US19/25475), Dec. 19, 2023.
Decision of Refusal for Japanese Patent Application No. 2021/503702, with English translation, dated Dec. 13, 2023 (6 pages).
Decision of Dismissal of Amendment for Japanese Patent Application No. 2021/503702, with English translation, dated Dec. 13, 2023 (6 pages).
Notice of Reasons for Refusal for Japanese Patent Application No. 2021/503702, with English translation, dated May 24, 2023 (8 pages).
Notice of Reasons for Refusal for Japanese Patent Application No. 2021/503702, with English translation, dated Nov. 8, 2022 (8 pages).
First Office Action for Chinese Patent Application No. 201980037883, with English translation, dated Oct. 10, 2022 (4 pages).
Second Office Action for Chinese Patent Application No. 201980037883, with English translation, dated Jun. 5, 2023 (10 pages).
Third Office Action for Chinese Patent Application No. 201980037883, with English translation, dated Nov. 14, 2023 (9 pages).
Decision of Rejection for Chinese Patent Application No. 201980037883, with English translation, dated Apr. 19, 2024 (12 pages).
First Examination Report for Indian Patent Application No. 202017046043 dated Aug. 4, 2022 (6 pages).
Office Action for Israeli Patent Application No. 277723, with English translation, dated Jul. 16, 2023 (10 pages).
Office Action for Brazilian Patent Application No. 1120200203157, with English translation, dated May 9, 2023 (8 pages).
Examination Report No. 1 for Australian Patent Application No. 2019247659 dated Jan. 8, 2024 (4 pages).
Malaysian Substantitive Examination Adverse Report (Section 30(1)) for Malaysian Patent Application No. PI2020005048 dated May 21, 2024 (4 pages).

\* cited by examiner

ESOPHAGEAL HEAT TRANSFER DEVICES AND METHODS FOR CARDIAC TISSUE ABLATION

CROSS REFERENCE TO RELATED APPLICATIONS

This patent application is a National Stage Entry of International Application Number PCT/US2019/025475, which was filed on Apr. 3, 2019 and claims priority to U.S. Provisional Patent Application No. 62/652,641, filed on Apr. 4, 2018, U.S. Provisional Patent Application No. 62/739,595, filed on Oct. 1, 2018, U.S. Provisional Patent Application No. 62/793,998, filed on Jan. 18, 2019, and U.S. Provisional Patent Application No. 62/795,916, filed on Jan. 23, 2019; the entire contents of each of the aforementioned applications are incorporated herein by reference.

TECHNICAL FIELD

The present technology relates to devices, systems, and methods for protecting esophageal tissue of a patient while that patient is undergoing a cardiac tissue ablation procedure by managing the temperature of esophageal tissue adjacent to an ablation site. In one aspect, the present technology relates to an esophageal heat transfer device for managing the temperature of esophageal tissue adjacent to an ablation site during cardiac tissue ablation. In another aspect, the present technology relates to a temperature management system including an esophageal heat transfer device for managing the temperature of esophageal tissue adjacent to an ablation site during cardiac tissue ablation. In still another aspect, the present technology relates to a method of utilizing an esophageal heat transfer device to manage the temperature of esophageal tissue adjacent to an ablation site during cardiac tissue ablation.

BACKGROUND

Atrial fibrillation is a common type of heart arrhythmia in which an atrium of a heart beats in an irregular or abnormal manner. It is often associated with heart failure, stroke, and other illness. A person suffering from atrial fibrillation may also experience heart palpations, lightheadedness, chest pains, and shortness of breath.

Cardiac tissue ablation procedures have been used to treat atrial fibrillation in patients. Tissue ablation (also referred to as catheter ablation or cryoablation or cryoballoon ablation) is a minimally-invasive procedure that is designed to electrically isolate an atrium from the aberrant electrical activity that causes the atrial fibrillation. For instance, during an ablation procedure, a catheter, balloon, or other device designed to ablate tissue is inserted into a left atrium of the heart of the patient. The catheter ablates (e.g., destroys) cardiac tissue by heating or freezing that tissue. Thus, the catheter creates a scar, causing that small portion of the cardiac tissue to be electrically inactive and, thus, unable to propagate aberrant electrical currents underlying heart arrhythmias.

In some instances, atrial ablation may cause unintended damage to a portion of a patient's esophagus adjacent to the left atrium as a result of the energy (e.g., thermal energy, most commonly by radiofrequency or cryothermy) applied to cardiac tissue. Indeed, ablation on the posterior wall of the left atrium is associated with a risk of esophageal injury, including perforation, atrio-esophageal fistula formation, erythema, erosion, hemorrhagic lesion, ulcer, mediastinitis, phrenic nerve injury, and other pen-esophageal nerve injury. For instance, lesions are formed on the esophagus of about 3% to 60% of patients who undergo left atrium ablation procedures.

Pulmonary vein isolation (PVI) is a standard catheter ablation procedure. Achieving isolation of the pulmonary veins requires ablation on the posterior wall of the left atrium over the esophagus. Ablation on the posterior wall of the left atrium is associated with a risk of esophageal injury, including perforation, atrio-esophageal fistula formation, erythema, erosion, hemorrhagic lesion, ulcer, mediastinitis, phrenic nerve injury, and other pen-esophageal nerve injury. Development of an atrio-esophageal fistula can be difficult to detect and is almost uniformly fatal if not treated promptly. Thus, adequate lesion placement is often limited as esophageal temperature rises.

Recently, atrial ablation procedures have incorporated luminal esophageal temperature (LET) monitoring in an attempt to reduce the incidence of esophageal injury during atrial ablation. In LET monitoring, a temperature probe is used to monitor the temperature of the esophageal lumen. However, the success of LET monitoring to detect whether lesions and/or other damage to esophageal tissue are about to occur has varied widely. One concern is that temperature of the lumen does not correspond to the temperature of the esophageal tissue at risk for damage; additionally LET monitoring measures only a single spatial point. Moreover, the temperature probe used in the LET monitoring potentially may contribute to a thermal effect and enhance direct tissue heating to the esophagus. For instance, some studies indicate that esophageal lesions form on about between 40% and 50% of patients with LET monitoring, regardless of whether a single-sensor or multi-sensor temperature probe is used.

Further, some operators have attempted to reduce an amount of energy provided by the catheter to the cardiac tissue, particularly on the posterior atrial wall, before a lesion and/or other damage forms on esophageal tissue. However, operators have found it difficult to adjust the energy level applied to the cardiac tissue while performing the atrial ablation procedure. For example, in attempting to avoid damaging esophageal tissue, the operator may reduce the energy before a durable lesion is formed in the atrial wall. Additionally or alternatively, some operators have attempted to control the temperature of the esophagus while performing an atrial ablation procedure. Devices for transferring heat to or from esophageal tissue have been proposed. However, operators have found it difficult to accurately control the temperature of the esophagus during the atrial ablation procedure in such a manner that lesions and/or other damage to esophageal tissue are avoided yet a durable lesion is formed in the atrial wall.

US 2007/0055328 (Mayse) refers to a distensible, thermally conductive balloon that can be filled with a coolant. Mayse asserts that the coolant, when circulating through the balloon and an external cooling machine, protects the esophageal tissue in contact with the esophageal probe from thermal damage during ablation of the posterior wall of the left atrium of the heart, or other procedure. Certain drawbacks of Mayse's device are outlined in US 2012/0035603 (Lenihan). For one, there is no way to know if effective cooling of the wall of the esophagus is being achieved.

US 2008/0161890 (Lafontaine) refers to an esophageal protecting device that includes an esophageal heat sink, which can be placed inside an esophagus while an ablation catheter is directing energy towards a cardiac tissue site.

US 2010/0168624 (Sliwa) refers to a tissue protecting apparatus having a heat sink, which is an element or structure having the capability of (i) carrying away heat deposited in the esophagus wall tissue by an ablation device, and/or (ii) cooling or pre-cooling the esophageal tissue that is to be protected.

US 2012/0035603 (Lenihan) refers to a temperature probe that may receive a coolant to keep portions of the esophagus wall opposite a catheter tip at a desired temperature.

US 2016/0278845 (Mayse) refers to devices and methods for treating one or more pulmonary diseases while avoiding or minimizing injury to esophageal tissue and branches of the vagus nerve that run along the outside of the esophagus.

None of these references acknowledge, let alone address, the interplay between achieving a durable ablation while simultaneously protecting esophageal tissue during a cardiac ablation (e.g., PVI procedure). Moreover, such devices and methods have been met with skepticism. For example, use of a cooling balloon could reduce the possibility of achieving a transmural lesion in the atrium, particularly in cases where the atrium is of considerable thickness, and when using a short duration and a low target temperature. See Berjano & Hornero, *Phys Med Biol* 2005, 50(20):N269-279.

Tsuchiya et al. (*J Cardiovasc Electrophysiol* 2007, 18(2): 145-150) reported that the luminal esophageal temperature during low-powered left atrial ablation was lowered by esophageal cooling using a cooled water-irrigated intraesophageal balloon catheter. Tsuchiya employed low-powered radiofrequency ablation, and as a consequence relatively low esophageal temperatures were obtained during the ablation. In view of the study design, Tsuchiya concluded that it might be impossible to determine whether or not its intervention actually prevented any esophageal injury. Moreover, later reports confirmed that Tsuchiya's method was complicated to perform in clinical practice and no follow-up studies were conducted. See Kuwahara et al., *Europace* 2014, 16:834-839.

Arruda et al. (*J Cardiovasc Electrophysiol* 2009, 20(11): 1272-1278) reported that, using a 12 Fr probe with a distal expandable compliant latex sac and circulating fluid within the sac at 5° C. or 10° C., esophageal tissue was spared from thermal injury in 2 animals in which the esophagus was not displaced against the left atrium. Conversely, Arruda reported that circulating fluid at 25° C. failed to spare esophageal tissue from thermal injury. Moreover, in an in vitro model, Arruda reported collateral esophageal thermal injury when fluid was circulated at 15° C. and 25° C. Thus, Arruda concluded that its method required a compliant sac and circulating fluid at 5° C. or 10° C.

Subsequent reports by Kuwahara et al. (*Europace* 2014, 16:834-839) and Sohara et al. (*J Cardiovasc Electrophysiol* 2014, 25(7):686-692) addressed the value of introducing a cooling fluid directly into the esophagus prior to radiofrequency ablation (Kuwahara) or hot balloon ablation when luminal esophageal temperature exceeded 39° C. or 43° C. (Sohara). Kuwahara reported that its method did not reduce the incidence of esophageal lesions due to radiofrequency ablation.

Thus, there is a need for devices and methods to improve esophageal protection during cardiac ablation procedures and improve the ability to achieve durable trans mural or partially-transmural atrial lesions, particularly in the posterior left atrial wall when esophageal tissue adjacent to the atrial wall is particularly susceptible to damage.

SUMMARY

The appended claims define this application. The present disclosure summarizes aspects of the embodiments and should not be used to limit the claims. Other implementations are contemplated in accordance with the techniques described herein, as will be apparent to one having ordinary skill in the art upon examination of the following drawings and detailed description, and these implementations are intended to be within the scope of this application.

The present disclosure provides devices and methods for balancing the desire to create a durable, transmural or partially-transmural lesion in the atrium with the desire to minimize, reduce, or eliminate collateral damage to esophageal tissue.

In one aspect, the present disclosure provides methods for preventing or reducing the risk of thermal injury to esophageal tissue in a patient undergoing a cardiac tissue ablation procedure. An exemplary method includes managing the temperature of the esophageal tissue, preferably the esophageal tissue adjacent to the ablation site, with an esophageal heat transfer device, wherein the esophageal heat transfer device includes (i) a heat transfer region, which is configured to be positioned within the esophagus, and more specifically, in thermal contact with the esophageal tissue adjacent to the ablation site, and (ii) one or more lumens configured to provide heat transfer fluid (e.g., water or saline) to and remove heat transfer fluid from the heat transfer region. In certain embodiments, the method also includes collecting esophageal data via one or more sensing elements of the esophageal heat transfer device. In certain embodiments, the method also includes determining, based on the esophageal data and/or an operator-selected power setting, a temperature setting and/or a flow rate setting for the fluid flowing through the esophageal heat transfer device to maintain a target temperature of esophageal tissue adjacent to the ablation site via the heat transfer region. In certain embodiments, the method also includes adjusting, via a controller, a fluid source to provide the fluid to the esophageal heat transfer device in accordance with the temperature setting and/or the flow rate setting.

In one aspect, the present disclosure provides methods for preventing or reducing the risk of thermal injury to esophageal tissue in a patient undergoing a pulmonary vein isolation (PVI) procedure. An exemplary method includes orally or nasally inserting an esophageal heat transfer device described herein into the patient's esophagus. The esophageal heat transfer device includes (i) a heat transfer region, which is configured to be positioned within the esophagus, and more specifically, in thermal contact with the esophageal tissue adjacent to the ablation site, and (ii) one or more lumens that provide heat transfer fluid (e.g., water or saline) to the heat transfer region. In certain embodiments, the method comprises performing the PVI procedure while simultaneously managing the temperature of esophageal tissue with the esophageal heat transfer device. For example, the method may comprise maintaining a target temperature of the esophageal tissue adjacent to the ablation site. In certain embodiments, the method comprises extracting heat from the esophageal tissue in a patient undergoing a radiofrequency (RF) ablation procedure. In some such embodiments, the PVI procedure comprises application of ablation energy to a posterior atrial wall segment of the patient and (a) a target minimum Ablation Index ($AI_{min}$) value of 300 on the posterior atrial wall segment or (b) a target minimum Force-Time Integral ($FTI_{min}$) value of 150 on the posterior atrial wall segment. In certain embodiments, the method further comprises improving an outcome in the patient undergoing the PVI procedure. In some such embodiments, the outcome is achievement of a durable lesion on a posterior segment of an atrial wall; freedom from any symptomatic atrial arrhythmia (atrial fibrillation, atrial flutter, atrial tachycardia) 12 months post-PVI procedure; and/or reduction in amount and/or severity of damage to esophageal tissue relative to performing the PVI procedure without such temperature management.

In one aspect, the present disclosure provides esophageal heat transfer devices for preventing or reducing the risk of thermal injury to esophageal tissue of a patient during cardiac tissue ablation. An exemplary esophageal heat transfer device includes a heat transfer region configured to add heat to or extract heat from esophageal tissue adjacent to an ablation site, one or more lumens defining a fluid path to provide fluid to the heat transfer region, a location sensing element to, for example, identify the esophageal tissue adjacent to an ablation site, and, optionally, a temperature sensor configured to measure a current temperature of the esophageal tissue adjacent to the ablation site when the heat transfer region is in contact with the esophageal tissue adjacent to the ablation site. In some embodiments, the location sensing element is or includes an esophageal heat transfer device location sensing element ("device-location sensing element") that enables the location of the esophageal heat transfer device to be identified (e.g., in relation to the ablation device and/or esophageal tissue identified as at risk for injury). A temperature setting and/or a flow rate setting of the fluid provided to the heat transfer region is adjusted by a controller based on one or more of an operator-selected power setting for the ablation catheter and the current temperature of the esophageal tissue adjacent to the ablation site.

In one aspect, the present disclosure provides esophageal heat transfer devices for preventing or reducing the risk of thermal injury to esophageal tissue of a patient during cardiac tissue ablation. An exemplary esophageal heat transfer device described herein includes a heat transfer region configured to add heat to or extract heat from esophageal tissue adjacent to an ablation site, one or more lumens defining a fluid path to provide fluid to the heat transfer region, and a non-contact temperature sensor configured to measure a current temperature of the esophageal tissue adjacent to the ablation site when the heat transfer region is in contact with the esophageal tissue adjacent to the ablation site. In certain embodiments, a temperature setting and/or a flow rate setting of the fluid provided to the heat transfer region is adjusted (e.g., by a controller) based on the current temperature of the esophageal tissue adjacent to the ablation site.

In another aspect, the present disclosure provides a heat transfer device that includes a tube having an outer wall that at least partially defines a lumen for flow of a heat transfer medium, a heat transfer region comprising at least a portion of the outer wall, and a non-contact temperature sensor that is physically separated from the heat transfer region and is configured to sense temperature of patient tissue adjacent to the heat transfer region. In certain embodiments, the heat transfer device of the present technology includes a temperature sensor that does not substantially impact heat transfer between the heat transfer region and the patient tissue adjacent to the heat transfer region.

In another aspect, the present disclosure provides a heat transfer device that includes a tube having an outer wall, the outer wall at least partially defining a lumen for flow of a heat transfer medium, wherein the outer wall is configured to contact patient tissue; a support surface disposed within the lumen; and a temperature sensor mounted to or embedded in the support surface, wherein the sensor is configured to sense temperature of a tissue in contact with the outer wall.

In another aspect, the present disclosure provides a multi-lumen heat transfer device that includes a tube having an outer wall, wherein the outer wall is configured to contact patient tissue; a plurality of lumens separated by at least one inner common support wall; and a temperature sensor mounted to or embedded in the at least one inner common support wall, wherein the sensor is configured to sense temperature of a tissue in contact with the outer wall. In certain embodiments, the present technology provides a heat transfer device that includes a temperature sensor that does not substantially impact heat transfer across the outer wall of the heat transfer device.

In yet another aspect, the present technology provides a heat transfer device that includes an infrared temperature sensor. In some embodiments, the infrared temperature sensor comprises one or more charge-coupled devices (CCDs). In some embodiments, the temperature sensor comprises one or more micro-electro-mechanical systems (MEMS). In embodiments where the infrared temperature sensor comprises a plurality of CCDs and/or MEMS, the individual sensors are preferably arranged in an array. In some such embodiments, the plurality of infrared temperature sensors are configured in a linear array. In other such embodiments, the plurality of infrared temperature sensors are configured in a two-dimensional array.

In still another aspect, the present disclosure provides methods for preventing or reducing the risk of thermal injury to esophageal tissue of a patient during cardiac tissue ablation using an esophageal heat transfer device disclosed herein. The esophageal heat transfer device includes (i) a heat transfer region, which can be positioned within the esophagus and, more specifically, in thermal contact with the esophageal tissue adjacent to the ablation site, and (ii) one or more lumens that provide fluid to the heat transfer region. An exemplary method disclosed herein includes sensing, via a non-contact temperature sensor, the temperature of the esophageal tissue adjacent to an ablation site. In some such embodiments, the non-contact temperature sensor is physically separated from the heat transfer region of the heat transfer device.

In certain embodiments, the method also includes collecting and/or storing esophageal temperature data. In certain embodiments, the method also includes determining, based on the esophageal temperature data, a temperature and/or a flow rate for the fluid flowing through the esophageal heat transfer device to maintain a target temperature of esophageal tissue adjacent to the ablation site. In certain embodiments, the method also includes adjusting, via a controller, a fluid source to provide the fluid to the esophageal heat transfer device in accordance with a temperature setting and/or a flow rate setting that is based, at least in part, on esophageal temperature data.

In certain embodiments, the sensing elements include a temperature sensor, such as a non-contact temperatures sensor, preferably an infrared temperature sensor. In some such embodiments, the temperature sensor is physically separated from the heat transfer region of the device.

BRIEF DESCRIPTION OF THE DRAWINGS

For a better understanding of the invention, reference may be made to embodiments shown in the following drawings. The components in the drawings are not necessarily to scale and related elements may be omitted, or in some instances proportions may have been exaggerated, so as to emphasize and clearly illustrate the novel features described herein. In addition, system components can be variously arranged, as known in the art. Further, in the drawings, like reference numerals designate corresponding parts throughout the several views.

DETAILED DESCRIPTION

Figure 1:
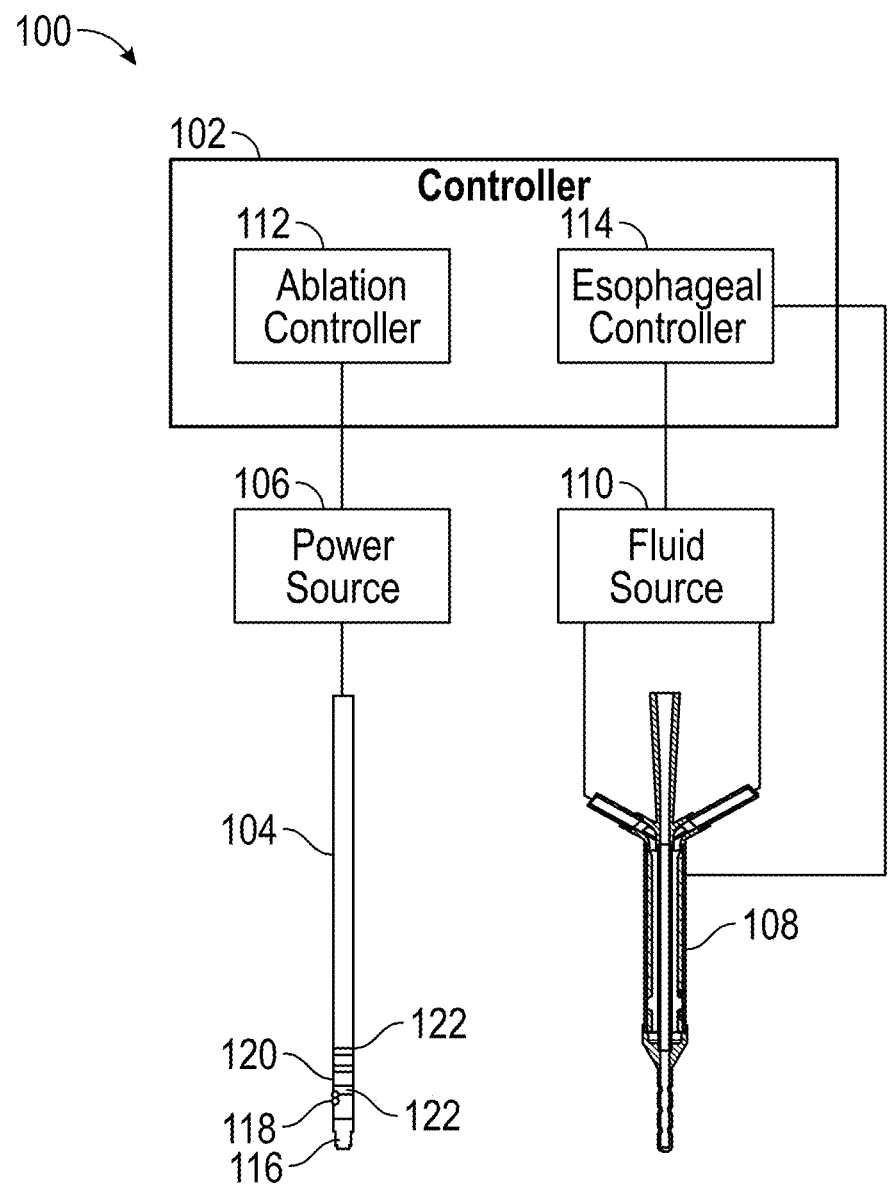
FIG. 1 illustrates an example ablation system in accordance with the teachings herein.

While the invention may be embodied in various forms, there are shown in the drawings, and will hereinafter be described, some exemplary and non-limiting embodiments, with the understanding that the present disclosure is to be considered an exemplification of the invention and is not intended to limit the invention to the specific embodiments illustrated.

A. METHODS

In one aspect, the present disclosure provides a method for protecting esophageal tissue in a patient undergoing a pulmonary vein isolation (PVI) procedure. The patient may suffer from, for example, atrial fibrillation (AF).

The method comprises orally or nasally inserting an esophageal heat transfer device into the patient's esophagus. In certain embodiments, the esophageal heat transfer device comprises a heat transfer region. In some such embodiments, the method comprises extracting heat from esophageal tissue adjacent to an ablation site in a patient undergoing a radiofrequency (RF) ablation procedure. In other such embodiments, the method comprises adding heat to esophageal tissue adjacent to an ablation site in a patient undergoing a cryoablation procedure.

In one aspect, the present disclosure provides a method for creating a durable ablation lesion during pulmonary vein isolation (PVI) without damaging esophageal tissue. In certain embodiments, the lesion is a transmural lesion. In certain embodiments, the lesion is a partially-transmural lesion.

The method comprises orally or nasally inserting an esophageal heat transfer device into the patient's esophagus. In certain embodiments, the esophageal heat transfer device comprises a heat transfer region. In some such embodiments, the method comprises simultaneously extracting heat from esophageal tissue adjacent to an ablation site while ablating a portion of the patient's left atrium using a radiofrequency (RF) ablation procedure. In other such embodiments, the method comprises simultaneously adding heat to esophageal tissue adjacent to an ablation site while ablating a portion of the patient's left atrium using a cryoablation procedure.

In one aspect, the present disclosure provides a method for preventing or reducing the risk of thermal injury to esophageal tissue in a patient undergoing a pulmonary vein isolation (PVI) procedure.

The method comprises orally or nasally inserting an esophageal heat transfer device into the patient's esophagus. In certain embodiments, the esophageal heat transfer device includes (i) a heat transfer region, which is configured to be positioned within the esophagus, and more specifically, in thermal contact with the esophageal tissue adjacent to the ablation site, and (ii) one or more lumens that provide heat transfer fluid (e.g., water or saline) to the heat transfer region.

In certain embodiments, the method comprises performing the PVI procedure while simultaneously managing the temperature of esophageal tissue with the esophageal heat transfer device. For example, the method may comprise maintaining a target temperature of esophageal tissue adjacent to the ablation site.

In certain embodiments, the method comprises adding heat to the esophageal tissue in a patient undergoing a cryoablation procedure. In certain other embodiments, the method comprises extracting heat from the esophageal tissue in a patient undergoing a radiofrequency (RF) ablation procedure. In some such embodiments, the PVI procedure comprises application of ablation energy to a posterior atrial wall segment of the patient and (a) a target minimum Ablation Index ($AI_{min}$) value of 300 on the posterior atrial wall segment or (b) a target minimum Force-Time Integral ($FTI_{min}$) value of 150 on the posterior atrial wall segment. As used herein, the term "Ablation Index" refers to a lesion quality marker that utilizes contact force, time, and power in a weighted formula as described in, for example, Nakagawa H, et al., Circulation 2013; 128:A12104; Das M, et al., Europace May 1 2017; 19:775-783. Ablation Index may be calculated as follows: $AI=(k*\int_0^t CF^a(\tau)P^b(\tau)d\tau)^c$, where CF is contact force, P is power, and d is duration. As used herein, the term "Force-Time Integral" refers to a lesion quality assessment tool that multiplies contact force by radiofrequency application duration. Force-Time Integral (FTI) may be calculated as follows: FTI=CF×d, where CF is mean contact force and d is duration.

It is believed that the methods described herein not only prevent or reduce the risk of thermal injury to esophageal tissue, but also permit the creation of a durable transmural or partially-transmural lesion on the posterior atrial wall segment by allowing for application of higher ablation energy, higher contact forces, and/or longer contact times than would otherwise be safely applied to the posterior atrial wall segment without such temperature management. Moreover, it is believed that the methods described herein reduce overall PVI procedure time because interruptions and/or stoppages to ablation treatment during the PVI procedure are minimized or even eliminated.

In certain embodiments, the PVI procedure comprises application of ablation energy to a posterior atrial wall segment of the patient and a target $AI_{min}$ value of at least 300, alternatively at least 310, alternatively at least 320, alternatively at least 330, alternatively at least 340, alternatively at least 350, alternatively at least 360, alternatively at least 370, alternatively at least 380, alternatively at least 390, alternatively at least 400, alternatively at least 410, alternatively at least 420, alternatively at least 430, alternatively at least 440, alternatively at least 450, alternatively at least 460, alternatively at least 470, alternatively at least 480, alternatively at least 490, alternatively at least 500, alternatively at least 510, alternatively at least 520, alternatively at least 530, alternatively at least 540, or alternatively at least 550 on the posterior atrial wall segment. In certain embodiments, the PVI procedure comprises application of ablation energy to a posterior atrial wall segment of the patient and a target $AI_{min}$ value from 300 to 550, alternatively from 350 to 500, or alternatively from 400 to 450 on the posterior atrial wall segment. In some such embodiments, the PVI procedure comprises a target $AI_{min}$ value of 310, 320, 330, 340, 350, 360, 370, 380, 390, 400, 410, 420, 430, 440, 450, 460, 470, 480, 490, 500, 510, 520, 530, 540, or 550 on the posterior atrial wall segment.

In certain embodiments, the PVI procedure does not comprise luminal esophageal temperature (LET) monitoring. In certain other embodiments, the PVI procedure comprises LET monitoring.

In certain embodiments, the method further comprises improving an outcome in the patient undergoing the PVI procedure. In some such embodiments, the outcome is achievement of a durable lesion on a posterior segment of an atrial wall and/or reduction in amount and/or severity of damage to esophageal tissue relative to performing the PVI procedure without such temperature management.

In one aspect, the present disclosure provides a method for reducing the risk of pulmonary vein (PV) reconnection and/or arrhythmia recurrence comprising performing a pulmonary vein isolation (PVI) procedure while simultaneously managing, and optionally monitoring, the temperature of esophageal tissue. It is believed that the method reduces the risk of pulmonary vein (PV) reconnection and/or arrhythmia recurrence by allowing for application of higher ablation energy, higher contact forces, and/or longer contact times than would otherwise be safely applied in the absence of such temperature management.

In certain embodiments, esophageal tissue temperature is managed using an esophageal heat transfer device, which may be orally or nasally inserted into the patient's esophagus.

In certain embodiments of any of the above aspects, the esophageal heat transfer device comprises a heat transfer region.

In some such embodiments, the heat transfer region is a discrete heat transfer region that is positioned adjacent to the portion of esophageal tissue at highest risk for being damaged. For example, the portion of esophageal tissue at highest risk for being damaged can be identified by imaging, such as thermal imaging, fluoroscopy, intracardiac echocardiography (ICE), and/or imaging the tip of the ablation catheter. As another example, the portion of esophageal tissue at highest risk for being damaged can be identified by mapping via one or more sensing elements; for example, a sensing element may be contained in the esophageal heat transfer device or, alternatively or additionally, outside the esophageal heat transfer device.

In some such embodiments, the heat transfer region comprises a thermally conductive wall. In operation, a heat transfer medium can flow along the thermally conductive wall to extract heat from, or add heat to, an adjacent anatomical structure (e.g., the esophagus) or a portion thereof.

In some such embodiments, the heat transfer region is substantially free of metallic temperature sensors, which have been implicated in worsening radiofrequency energy transfer through the esophagus and/or contributing to the formation of esophageal thermal lesions because of power absorption by the metallic sensors. In a particular embodiment, the heat transfer region is substantially free of metallic conductive pathways.

In some such embodiments, the flowing heat transfer medium has a temperature from about 0° C. to about 42° C., alternatively from about 5° C. to about 30° C., alternatively from about 10° C. to about 25° C., or alternatively from about 15° C. to about 20° C. Additional ranges for the temperature of the flowing heat transfer medium include from about 0° C. to about 5° C., alternatively from about 5° C. to about 15° C., alternatively from about 10° C. to about 20° C., alternatively from about 15° C. to about 25° C., alternatively from about 20° C. to about 30° C., alternatively from about 25° C. to about 35° C., alternatively from about 30° C. to about 40° C., alternatively from about 35° C. to about 45° C., alternatively from about 40° C. to about 50° C., alternatively from about 45° C. to about 55° C., alternatively from about 50° C. to about 60° C., alternatively from about 55° C. to about 65° C., alternatively from about 60° C. to about 70° C., alternatively from about 65° C. to about 75° C., or alternatively from about 70° C. to about 80° C. In certain embodiments, the flowing heat transfer medium has a temperature less than about 25° C., alternatively less than about 20° C., alternatively less than about 15° C., or alternatively less than about 10° C. in radiofrequency ablation applications. In certain embodiments, the flowing heat transfer medium has a temperature up to about 37° C., alternatively up to about 42° C., alternatively up to about 45° C., or alternatively up to about 80° C. in cryoablation applications.

For example, for a PVI procedure employing an RF ablation energy from about 20 W to about 30 W, the flowing heat transfer medium has a temperature from about 5° C. to about 30° C., alternatively from about 10° C. to about 25° C., or alternatively from about 15° C. to about 20° C.

As another example, for a PVI procedure employing an RF ablation energy from about 20 W to about 30 W and a contact force from about 10 g to about 40 g, the flowing heat transfer medium has a temperature from about 5° C. to about 30° C., alternatively from about 10° C. to about 25° C., or alternatively from about 15° C. to about 20° C.

As yet another example, for a PVI procedure employing an RF ablation energy from about 20 W to about 30 W, a contact force from about 10 g to about 40 g, and a contact time from about 10 sec to about 40 sec, the flowing heat transfer medium has a temperature from about 5° C. to about 30° C., alternatively from about 10° C. to about 25° C., or alternatively from about 15° C. to about 20° C.

In one aspect, the present disclosure provides a method for protecting esophageal tissue in a patient undergoing a pulmonary vein isolation (PVI) procedure for atrial fibrillation (AF) without impairing the attainment of a durable ablation. The method comprises circulating heat transfer medium along a fluid path in a heat transfer device placed in the esophagus of the patient. The method further comprises selecting a temperature of the circulating heat transfer medium that provides at least one isotherm in atrial tissue ("atrial isotherm(s)") having a temperature sufficient to produce cell death in the atrial tissue and at least one isotherm in esophageal tissue ("esophageal isotherm(s)") having a temperature that would not cause cell death.

Experimental studies have shown that irreversible tissue destruction occurs when tissue temperature exceeds 50° C. and, therefore, 50° C. is often regarded as the boundary of necrotic cells and survival cells in radiofrequency ablation. Thus, the 50° C. isotherm in the tissue can be used to estimate lesion size.

In certain embodiments relating to radiofrequency ablation, the temperature of the atrial isotherm(s) is above 50° C. and the temperature of the esophageal isotherm(s) are below 50° C. In certain embodiments relating to radiofrequency ablation, the temperature of the atrial isotherm(s) are from about 50° C. to about 90° C., alternatively from about 60° C. to about 85° C., or alternatively from about 70° C. to about 80° C. and the temperature of the esophageal isotherm(s) are from about 30° C. to about 50° C., alternatively from about 35° C. to about 45° C., or alternatively from about 37° C. to about 42° C.

In certain embodiments, the atrial isotherm(s) are transmural, spanning the entire posterior wall of the left atrium. In certain embodiments, the atrial isotherm(s) are partially-transmural. In certain embodiments, the depth of the atrial isotherm(s) is about 1 mm to about 6 mm.

Experimental studies also have shown that tissue damage is a function of both temperature and time. Thus, a model that takes the temperature history into account, such as cumulative equivalent minutes of thermal treatment at 43° C. (CEM43° C.), in the tissue can also be used to estimate lesion size.

In one aspect, the present disclosure provides a method for protecting esophageal tissue from thermal damage during a cardiac ablation procedure (e.g., a pulmonary vein isolation procedure). The method comprises orally or nasally inserting an esophageal heat transfer device into a patient and positioning a heat transfer region of the device within the esophagus and, in particular, near esophageal tissue that is susceptible to inadvertent damage during the cardiac ablation procedure.

The method further comprises flowing a heat transfer medium along a fluid path of the device. In certain embodiments, the heat transfer medium is at a temperature sufficient to protect esophageal tissue from thermal damage without substantially interfering with the ability to obtain a durable, transmural lesion on the wall of the atrium.

During ablation procedures at the posterior wall of the left atrium, an appropriate temperature for the heat transfer medium may depend upon the operator-selected power setting, contact force, and/or time. For example, in certain embodiments, the temperature of the heat transfer medium is selected in accordance with the guidance set forth in Tables A-G below.

TABLE A

Recommended water temperature (° C.) for selected ablation energy.

| Watts | ° C. |
|---|---|
| 10 | 5-40 |
| 20 | 0-25 |
| 30 | 0-20 |
| 40 | 0-15 |
| 50 | 0-15 |

TABLE B

Recommended water temperature (° C.) for selected ablation energy applied for 30 seconds.

| Watts | ° C. |
|---|---|
| 5 | 20-30 |
| 10 | 15-25 |
| 15 | 10-20 |
| 20 | 5-15 |
| 25 | 0-10 |
| 30 | 0-10 |

TABLE C

Recommended water temperature (° C.) for selected ablation energy applied for 15 seconds.

| Watts | ° C. |
|---|---|
| 5 | 25-35 |
| 10 | 20-30 |
| 15 | 15-25 |
| 20 | 10-20 |
| 25 | 5-15 |
| 30 | 0-10 |

TABLE D

Recommended water temperature (° C.) for selected ablation energy applied for about 30 seconds at about 15 g contact force.

| Watts | ° C. |
|---|---|
| 10 | 5-15 |
| 20 | 0-10 |
| 30 | 0-10 |
| 40 | 0-5 |
| 50 | 0-5 |

TABLE E

Recommended water temperature (° C.) for selected ablation energy applied for about 20 seconds at about 15 g contact force.

| Watts | ° C. |
|---|---|
| 10 | 10-20 |
| 20 | 5-15 |
| 30 | 0-10 |
| 40 | 0-10 |
| 50 | 0-5 |

TABLE F

Recommended water temperature (° C.) for selected ablation energy applied for about 10 seconds at about 15 g contact force.

| Watts | ° C. |
|---|---|
| 10 | 25-30 |
| 20 | 10-15 |
| 30 | 10-15 |
| 40 | 5-10 |
| 50 | 5-10 |

TABLE G

Recommended water temperature (° C.) for selected ablation energy applied for about 4 seconds at about 15 g contact force (e.g., a HPSD ablation device).

| Watts | ° C. |
|---|---|
| 70 | 10-20 |
| 80 | 5-15 |
| 90 | 0-10 |

In certain embodiments, a recommended water temperature—or heat transfer medium temperature—may fall below 0° C., such as −5, −4, −3, −2, or −1° C. In some such embodiments, heat transfer medium temperatures below 0° C. may be employed for a relatively short duration of time, such as less than 15 minutes, alternatively less than 10 minutes, or alternatively less than 5 minutes.

In certain embodiments, the method comprises determining, via a controller, a temperature setting and/or a flow rate setting for the heat transfer fluid. The temperature setting and/or flow rate setting may be determined based on collected esophageal temperature data or an operator-selected ablation setting. In certain embodiments, the method also comprises circulating the heat transfer fluid through the one or more lumens at the determined temperature setting and/or flow rate setting to maintain a target temperature of the esophageal tissue susceptible to damage.

In certain embodiments, the method further comprises adjusting, via a controller, a fluid source to provide the fluid to the esophageal heat transfer device in accordance with the temperature setting and/or the flow rate setting.

In certain embodiments, the temperature setting is a specific value, such as 0, 5, 10, 15, 20, 25, 30, or 35° C. In certain other embodiments, the temperature setting is a range of values. For example, in some such embodiments, the temperature setting is from about 0° C. to about 10° C., alternatively from about 5° C. to about 15° C., alternatively from about 10° C. to about 20° C., alternatively from about 15° C. to about 25° C., alternatively from about 20° C. to about 30° C., or alternatively from about 25° C. to about 35° C.; additional ranges for the temperature setting include from about 0° C. to about 5° C., alternatively from about 5°

C. to about 10° C., alternatively from about 10° C. to about 15° C., alternatively from about 15° C. to about 20° C., alternatively from about 20° C. to about 25° C., alternatively from about 25° C. to about 30° C., or alternatively from about 30° C. to about 35° C.

In one aspect, the present disclosure provides a method for protecting esophageal tissue from thermal damage during an atrial fibrillation ablation procedure (e.g., a pulmonary vein isolation procedure). The method comprises orally or nasally inserting an esophageal heat transfer device described herein into a patient and positioning a heat transfer region of the device within the esophagus and, in particular, near esophageal tissue that is susceptible to inadvertent damage during the atrial fibrillation ablation procedure. In some embodiments the method includes monitoring the temperature of esophageal tissue using a non-contact temperature sensor described herein (i.e., a temperature sensor that is physically separated from the heat transfer region).

In certain embodiments, the method also includes collecting esophageal temperature data via a non-contact temperature sensor described herein (i.e., a temperature sensor that is physically separated from the heat transfer region).

In certain embodiments, the method includes adjusting, via a controller, the temperature setting and/or the flow rate setting of a fluid source to maintain the esophageal tissue at the target temperature. That is, the temperature setting and/or the flow rate setting can be adjusted during the cardiac tissue ablation procedure to control the temperature and/or flow rate of the fluid provided by the fluid source to the heat transfer region. For example, if a temperature sensor of the esophageal heat transfer device detects that the esophageal tissue adjacent to the ablation site is approaching a temperature at which lesion(s) form, the temperature setting and/or the flow rate setting is adjusted to control the temperature and/or flow rate of the fluid flowing from the fluid source to the heat transfer region, which in turn causes the temperature of that esophageal tissue to return toward the target temperature (i.e., a temperature at which lesion(s) do not form).

In certain embodiments, the method includes simultaneously measuring and managing temperature of esophageal tissue susceptible to damage during a cardiac ablation procedure by positioning a device of the present technology into the esophagus of a patient and, optionally, adjusting a temperature management parameter based on signals produced by the temperature sensor. In some such embodiments, the temperature management parameter is temperature of the heat transfer medium.

In one aspect, the present disclosure provides a method for simultaneously measuring and managing temperature of esophageal tissue susceptible to damage during a radiofrequency ablation procedure. In one embodiment, the present technology provides a method for simultaneously measuring and managing temperature of esophageal tissue susceptible to damage during a cryoablation procedure.

In one aspect, the present disclosure provides a method for preventing or reducing the risk of thermal injury to esophageal tissue during a cardiac tissue ablation procedure while simultaneously detecting the temperature of the esophageal tissue susceptible to thermal injury. The method comprises orally or nasally inserting an esophageal heat transfer device described herein into the patient's esophagus. In certain embodiments, the method comprises detecting and, optionally, monitoring the temperature of esophageal tissue and, preferably the esophageal tissue identified as being susceptible to damage during a cardiac ablation procedure. In some such embodiments, the method comprises extracting heat from the esophageal tissue in a patient undergoing a radiofrequency (RF) ablation procedure for AF. In other such embodiments, the method comprises adding heat to the esophageal tissue in a patient undergoing a cryoablation procedure for AF.

In certain embodiments, if the esophageal tissue adjacent to the ablation site is approaching a temperature at which lesion(s) form, the method comprises adjusting the temperature of the fluid provided to the esophageal heat transfer device to cause the temperature of the esophageal tissue to return toward a target temperature at which lesion(s) do not form.

In certain embodiments, the method also includes collecting esophageal temperature data via a non-contact temperature sensor described herein (i.e., a temperature sensor that is physically separated from the heat transfer region).

In one aspect, the present disclosure provides methods for preventing or reducing the risk of thermal injury to esophageal tissue of a patient during cardiac tissue ablation. An exemplary method includes activating, via a controller, a tissue ablation device at an operator-selected power setting. A tip of the tissue ablation device is positioned at an ablation site (e.g., a portion of the wall of the left atrium) of the patient. In certain embodiments, the method also includes collecting esophageal data via one or more sensing elements of an esophageal heat transfer device positioned within an esophagus of the patient. The esophageal heat transfer device includes a heat transfer region, which is positioned within the esophagus adjacent to the ablation site and one or more lumens that provide fluid to the heat transfer region. In certain embodiments, the method also includes determining, based on the esophageal data and/or an operator-selected power setting, a temperature setting and/or a flow rate setting for the fluid flowing through the esophageal heat transfer device to maintain a target temperature of esophageal tissue adjacent to the ablation site via the heat transfer region. In certain embodiments, the method also includes adjusting, via the controller, a fluid source to provide the fluid to the esophageal heat transfer device in accordance with the temperature setting and/or the flow rate setting.

In one aspect, the present disclosure provides methods for preventing or reducing the risk of thermal injury to esophageal tissue of a patient during cardiac tissue ablation. In certain embodiments, the method includes activating a tissue ablation device at an operator-selected power setting via a controller. The tissue ablation device is positioned at an ablation site in, for example, the left atrium of the patient when the tissue ablation device is activated. In certain embodiments, the tissue ablation device remains activated at the operator-selected power setting throughout the cardiac tissue ablation procedure. That is, in such examples, the operator-selected power setting is a constant value (e.g., between about 5 Watts and 90 Watts, for example 50 Watts) that remains unchanged throughout the cardiac tissue ablation procedure.

In certain embodiments, the method includes, prior to activating the tissue ablation device, positioning the tissue ablation device next to the ablation site and positioning an esophageal heat transfer device within an esophagus of the patient such that a heat transfer region of the esophageal heat transfer device is in thermal contact with the esophageal tissue adjacent to the ablation site of the cardiac tissue. For example, the method may include detecting a position of the esophageal heat transfer device using a device-location sensing element. Further, in certain embodiments, to position the heat transfer region of the esophageal heat transfer device near the ablation site of the cardiac tissue, the method may include detecting a position of the tissue ablation device and identifying the esophageal tissue adjacent to the ablation site based upon the position of the tissue ablation device. For example, the position of the tissue ablation device and/or esophageal heat transfer device can be detected via one or more magnetic field sensors (e.g., one or more coils, such as three orthogonally configured coils) integrated with the tissue ablation device and/or esophageal heat transfer device. As another example, the position of the tissue ablation device and/or esophageal heat transfer device can be detected via an acoustic transducer integrated with the esophageal heat transfer device and/or tissue ablation device. The acoustic transducer in one device may be configured to emit acoustic waves and further configured to receive a pulse-echo reflection of the signal and communicate the signal to a processor to determine the position of the other device. Further, in certain embodiments, the esophageal tissue adjacent to the ablation site is identified via a thermal imaging element of the esophageal heat transfer device. In certain embodiments, radiofrequency ablation is performed to the ablation site. In other examples, cryoablation is performed to the ablation site.

In certain embodiments, the ablation device and/or system may be a High Power Short Duration (HPSD) RF catheter system. In some such embodiments, the ablation energy applied is greater than 50 Watts, such as 60, 70, 80, 90 or 100 Watts and the duration is less than 10 seconds, such as about 9, 8, 7, 6, 5, 4, 3, 2, or 1 seconds.

In certain embodiments, the method also includes collecting esophageal data via one or more sensing elements of an esophageal heat transfer device when the esophageal heat transfer device is positioned within the esophagus of the patient. In certain embodiments, the esophageal data includes a temperature, a pressure, and/or other data, and the one or more sensing elements include a temperature sensor, a pressure sensor, and/or other sensing element(s) to collect the esophageal data. For example, a temperature sensor of the esophageal heat transfer device is configured to measure a current temperature of the esophageal tissue adjacent to the ablation site and/or a pressure sensor of the esophageal heat transfer device is configured to measure a current pressure applied by the esophageal heat transfer device onto the esophageal tissue adjacent to the ablation site.

In certain embodiments, the method includes selecting (e.g., via a controller) a temperature setting and/or a flow rate setting for the fluid flowing through the esophageal heat transfer device to the heat transfer region based on the collected esophageal data and/or other data. The temperature setting and/or the flow rate setting of the fluid can be selected to enable the esophageal heat transfer device to maintain, via the heat transfer region, a target temperature of esophageal tissue adjacent to the ablation site that, for example, deters lesions and/or other damage to esophageal tissue. In certain embodiments, the other data utilized to determine the temperature setting and/or the flow rate setting includes a duration of time the ablating energy is applied to the ablation site and/or the contact force applied to the ablation site by the ablation catheter.

In certain embodiments, the method includes adjusting, via a controller, the temperature setting and/or the flow rate setting to maintain the esophageal tissue at the target temperature. That is, the temperature setting and/or the flow rate setting is adjusted during the cardiac tissue ablation procedure to prevent or reduce the risk of lesions from forming at the esophageal tissue adjacent to the ablation site. For instance, if a temperature sensor of the esophageal heat transfer device detects that the esophageal tissue adjacent to the ablation site is approaching a temperature at which lesion(s) form in esophageal tissue, the temperature setting and/or the flow rate setting is adjusted to cause the temperature of that esophageal tissue to return toward the target temperature at which lesion(s) do not form. In certain embodiments, the temperature setting and/or the flow rate setting is adjusted for a duration of the cardiac tissue ablation procedure. Further, in certain embodiments, the esophageal heat transfer device is deactivated via the controller in response to identifying that the tissue ablation device has been deactivated.

B. DEVICES

An exemplary esophageal heat transfer device is a multi-lumen tube having an inflow lumen and outflow lumen and, optionally, a gastric access lumen. The esophageal heat transfer device includes a heat transfer region, which is configured to be positioned within the esophagus, and more specifically, in thermal contact with esophageal tissue adjacent to cardiac tissue, such as a posterior atrial wall segment. In certain embodiments, the heat transfer region comprises at least a portion of an outer wall of the multi-lumen tube (e.g., a discrete portion of the outer wall that has been positioned in thermal contact with esophageal tissue adjacent to an ablation site). In some such embodiments, the portion of the outer wall is uninsulated and/or comprises a material with high thermal conductivity while a second portion of the outer wall is insulated and/or comprises a material with low thermal conductivity. In operation, the inflow lumen can be fluidly connected to a fluid source (e.g., an external heat exchanger) to provide heat transfer fluid to the heat transfer region of the device. In addition, the outflow lumen can be fluidly connected to the fluid source (e.g., an external heat exchanger) to allow the heat transfer fluid to return to the fluid source. In certain embodiments, the esophageal heat transfer device includes a gastric access tube defining a gastric access lumen which allows for at least one of gastric decompression, gastric suctioning, or enteral administration of fluids. In certain embodiments, the multi-lumen tube is a non-compliant tube. In certain embodiments, the multi-lumen tube is a multi-lumen silicone tube.

In certain embodiments, the esophageal heat transfer device includes a device-location sensing element. In some embodiments, the device-location sensing element includes a fiducial marker detectable by a mapping and/or imaging system. In some embodiments, the device-location sensing element includes a radiopaque marker visible to a visualization instrument, to, for example, aid in placement of the esophageal heat transfer device and/or enable orientation of the heat transfer region. In some embodiments, the device-location sensing element includes one or more magnetic field sensors. In some such embodiments, the one or more magnetic field sensors create a signal in response to a magnetic field emitted by a magnetic field emitter (e.g., a locator pad that is placed beneath the patient during the procedure). In some embodiments, the device-location sensing element includes a tri-axial sensor, preferably a tri-axial sensor that includes three orthogonally configured coils.

In certain embodiments, the heat transfer region is bordered by a region of limited thermal conductivity (e.g., a partially-conductive or non-conductive region) such that heat transfer between the device and the patient tissue is localized to the heat transfer region of the esophageal heat transfer device. In some such embodiments, the partially-conductive or non-conductive region includes an insulating material surrounding, or at least partially surrounding, a portion of the outer wall of the multi-lumen tube. Additionally or alternatively, the partially-conductive or non-conductive region may include a portion of the outer wall that comprises a material with low thermal conductivity. In some such embodiments, the heat transfer region includes a material with high thermal conductivity and the partially-conductive or non-conductive region includes a material with low thermal conductivity. Thus, in some embodiments, the heat transfer region may be a physically discrete region bordered by at least one partially-conductive or non-conductive region. In certain embodiments, the heat transfer region is adjacent to a partially-conductive or non-conductive region such that the partially-conductive or non-conductive region at least partially defines a boundary of the heat transfer region.

In one aspect, the present disclosure provides an esophageal heat transfer device for preventing or reducing the risk of thermal injury to esophageal tissue of a patient during a cardiac tissue ablation procedure. In certain embodiments, the esophageal heat transfer device comprises at least one lumen defining a fluid path for flow of a heat transfer medium and a heat transfer region. In some such embodiments, the esophageal heat transfer device is configured such that the heat transfer region can be positioned within the esophagus and, in particular, near esophageal tissue that is susceptible to inadvertent damage during the ablation procedure. In some such embodiments, the heat transfer region comprises the entirety of the portion of the esophageal heat transfer device that is positioned within the esophagus. In other such embodiments, the heat transfer region comprises a discrete portion of the esophageal heat transfer device that is positioned within the esophagus. For example, the heat transfer region may be about 1 centimeter to about 15 centimeters in length, alternatively about 3 centimeters to about 7 centimeters in length, or alternatively about 4 centimeters to about 6 centimeters in length. As another example, a first portion of the esophageal heat transfer device that is positioned within the esophagus is insulated and a second portion of the esophageal heat transfer device that is positioned within the esophagus is uninsulated, thereby forming the heat transfer region. In certain embodiments, the esophageal heat transfer device further comprises one or more sensing element, such as a location sensing element. In some such embodiments, the location sensing element includes a magnetic coil, an acoustic transducer, a thermal imaging element, and/or any other sensing element configured to detect the location of the ablation site, the esophageal tissue adjacent to the ablation site, and/or a tissue ablation device performing the tissue ablation procedure.

In one aspect, the present disclosure provides an esophageal heat transfer device for preventing or reducing the risk of thermal injury to esophageal tissue of a patient during a cardiac tissue ablation procedure and, furthermore, is capable of providing information, including location information, to, for example, a mapping and/or imaging system. For example, the esophageal heat transfer device may have one or more fiducial markers, which are detectable by the mapping and/or imaging system and provide a point of reference (e.g., in relation to the ablation device and/or esophageal tissue identified as at risk for injury). In some such embodiments, the heat transfer device comprises a marker, such as a marker visible to a visualization instrument to allow the heat transfer device to be visualized. For example, the marker may be a radiopaque marker.

In certain embodiments, the esophageal heat transfer device includes a location sensing element and, preferably, a device-location sensing element (e.g., a magnetic coil, an acoustic transducer) that enables the location of the esophageal heat transfer device to be identified (e.g., in relation to the ablation device and/or esophageal tissue identified as at risk for injury).

In some embodiments, the device-location sensing element includes one or more magnetic field sensors. In some such embodiments, the esophageal heat transfer device includes two or more (e.g., three) magnetic field sensors. In some embodiments, the magnetic field sensor(s) create a signal in response to a magnetic field emitted by a magnetic field emitter, such as a locator pad placed beneath the patient.

In some embodiments, the device-location sensing element includes a tri-axial sensor. In some such embodiments, the tri-axial sensor includes three orthogonally configured coils.

In a particular embodiment, the esophageal heat transfer device may include one or more magnetic coils (e.g., one, two, or three magnetic coils) that enable the location of the esophageal heat transfer device to be identified.

Thus, in operation of certain embodiments, the magnetic field strength is detected by two or more, preferably three, magnetic field sensors. The magnetic field strength is inversely proportional to the distance between the particular magnetic field sensor and magnetic field emitter. Hence, by integrating an emitter's field strength and converting this measurement into a distance, the device-location sensing element (and therefore, esophageal heat transfer device or, preferably, the heat transfer region of the esophageal heat transfer device) can be triangulated in space.

In one aspect, the present disclosure provides an esophageal heat transfer device for preventing or reducing the risk of thermal injury to esophageal tissue of a patient during a cardiac tissue ablation procedure. The esophageal heat transfer device comprises (i) a heat transfer region to regulate the temperature of esophageal tissue adjacent to an ablation site during the cardiac tissue ablation procedure and (ii) a non-contact temperature sensor configured to measure a current temperature of the esophageal tissue adjacent to the ablation site when the heat transfer region is in contact with that esophageal tissue. The temperature sensor is physically separated from the heat transfer region. In certain embodiments, the heat transfer region comprises a thermally conductive wall. In operation, a heat transfer medium can flow along the thermally conductive wall to extract heat from, or add heat to, an adjacent anatomical structure (i.e., the esophagus) or a portion thereof.

As used herein, the term "non-contact temperature sensor" refers to a sensor that senses, without physically contacting the target object (e.g., human tissue), a temperature-related parameter, such as infrared energy emitted by the object, and converts the temperature-related parameter into an electrical signal representative of object temperature. Thus, a non-contact temperature sensor can be, and preferably is, physically separated from the esophageal tissue adjacent to the ablation site. Moreover, in certain embodiments, the non-contact temperature sensor is also physically separated from the portion of the heat transfer region in thermal contact with the esophageal tissue adjacent to an ablation site; it is believed that such an arrangement does not substantially impact heat transfer between the heat transfer region and the patient tissue adjacent to the heat transfer region. In certain embodiments, the non-contact temperature sensor comprises an infrared temperature sensor, such as a charge-coupled device (CCD). In some such embodiments, the non-contact temperature sensor comprises includes a plurality of CCDs. In certain embodiments, the non-contact temperature sensor comprises a micro-electro-mechanical system (MEMS). In some such embodiments, the non-contact temperature sensor comprises a plurality of MEMS. In embodiments where the non-contact temperature sensor comprises a plurality of CCDs and/or MEMS, the individual sensors are preferably arranged in an array. In some such embodiments, the array is a linear array. In other such embodiments, the array is a two-dimensional array.

In certain embodiments, the esophageal heat transfer device includes a heat transfer region comprising an outer wall of a tube. In some such embodiments, the outer wall at least partially defines a lumen and the lumen is further defined by an interior wall. In some such embodiments, the temperature sensor, which is configured for sensing the temperature of esophageal tissue in contact with the outer wall, is embedded in or mounted on the interior wall.

In certain embodiments, the esophageal heat transfer device is a multi-lumen heat transfer device with a tissue-contacting outer wall defining a plurality of lumens separated by an inner common support wall that contains a temperature sensor embedded therein or mounted thereon, wherein the sensor is configured to sense temperature of a tissue in contact with the outer wall.

In one aspect, the present disclosure provides esophageal heat transfer devices for preventing or reducing the risk of thermal injury to esophageal tissue of a patient during cardiac tissue ablation. An exemplary esophageal heat transfer device includes a heat transfer region configured to add heat to or extract heat from esophageal tissue adjacent to an ablation site, one or more lumens defining a fluid path to provide fluid to the heat transfer region, a location sensing element to identify the ablation catheter, the ablation site, and/or the esophageal tissue adjacent to the ablation site, and a temperature sensor that is physically separated from the heat transfer region and configured to sense a current temperature of the esophageal tissue adjacent to the ablation site when the heat transfer region is in contact with the esophageal tissue adjacent to the ablation site.

In one aspect, the present disclosure provides an esophageal heat transfer device comprising a heat transfer region and a non-contact temperature sensor that is physically separated from the heat transfer region. In certain embodiments, the heat transfer device includes a tube having an outer wall that at least partially defines a lumen, wherein the lumen is further defined by a support wall and the support wall includes the temperature sensor, which is configured to sense the temperature of esophageal tissue in contact with the outer wall. In some embodiments, the heat transfer device is a multi-lumen heat transfer device with a tissue-contacting outer wall defining a plurality of lumens separated by an inner common support wall that contains a temperature sensor, wherein the sensor is configured to sense temperature of a tissue in contact with the outer wall. In certain embodiments, the temperature sensor comprises an infrared temperature sensor. In certain embodiments, the temperature sensor comprises a CCD. In certain embodiments, optics, such as lenses may be used to increase or optimize the area monitored by the sensor. In certain embodiments, cooling fluid may act as a lens. In certain embodiments, the heat transfer device comprises a marker, such as a marker visible to a visualization instrument, to enable orientation of the heat transfer region and/or temperature sensor in the esophagus. In some such embodiments, the visible marker is a radiopaque marker.

In one aspect, the present disclosure provides an esophageal heat transfer device that is configured to prevent or reduce the risk of thermal injury to esophageal tissue of a patient during cardiac tissue ablation. In certain embodiments, the esophageal heat transfer device includes a heat transfer region that is configured to add heat to or extract heat from esophageal tissue adjacent to an ablation site. For example, the heat transfer region extends from about 1 centimeter to about 15 centimeters along a length of the esophageal heat transfer device to enable the esophageal heat transfer device to transfer heat in a localized manner. In certain embodiments, the heat transfer region includes an intra-esophageal balloon through which the fluid flows to add heat to or extract heat from esophageal tissue. Further, in certain embodiments, the heat transfer region is defined at a portion of an exterior surface of the esophageal heat transfer device by an insulating layer that extends along another portion of the exterior surface. For example, the insulating layer includes a thick layer of tubing and/or a pocket of air enclosed within the esophageal heat transfer device. Further, in certain embodiments, the exterior surface forms a snug fit with an esophageal wall to stabilize a position of the heat transfer region within the esophagus of the patient. For example, the esophageal heat transfer device includes an inflatable portion to enable the exterior surface to form the snug fit with the esophageal wall and/or an outer diameter that enables the exterior surface to form the snug fit with the esophageal wall.

In certain embodiments, the esophageal heat transfer device includes an inflatable heat transfer region. In certain other embodiments, the esophageal heat transfer device includes a heat transfer region that is not inflatable. In certain embodiments, the heat transfer region includes a balloon. In certain other embodiments, the heat transfer region does not include a balloon. In certain embodiments, the heat transfer region comprises a portion of an outer wall of a balloon or length of compliant tubing. In certain embodiments, the heat transfer region comprises a portion of an outer wall of a length of non-compliant tubing.

In certain embodiments, the esophageal heat transfer device includes one or more lumens that define a fluid path to provide fluid to the heat transfer region, a location sensing element configured to identify the esophageal tissue adjacent to an ablation site, and/or a temperature sensor configured to measure a current temperature of the esophageal tissue adjacent to the ablation site when the heat transfer region is in contact with the esophageal tissue adjacent to the ablation site. For example, the location sensing element may include a magnetic coil, an acoustic emitter and/or receiver, a thermal imaging element, and/or any other sensing element configured to detect the location of the ablation site, the esophageal tissue adjacent to the ablation site, and/or a tissue ablation device performing the tissue ablation procedure. Further, in certain embodiments, the esophageal heat transfer device includes a pressure sensor that is configured to measure a current pressure applied to the esophageal tissue adjacent to the ablation site during the cardiac tissue ablation procedure.

In certain embodiments, a temperature setting and/or a flow rate setting of the fluid provided to the heat transfer region of the esophageal heat transfer device is adjusted by a controller that is coupled to the esophageal heat transfer device to prevent or reduce the risk of lesions and/or other damage to esophageal tissue during the cardiac tissue ablation procedure. That is, the temperature setting and/or the flow rate setting of the fluid flowing through the esophageal heat transfer device is adjusted during the cardiac tissue ablation procedure to prevent or reduce the risk of lesions from forming at the esophageal tissue adjacent to the ablation site. For example, the temperature setting and/or the flow rate setting is adjusted based on the current temperature, the current pressure, other esophageal data, and/or any other data that affects the formation of lesion(s) on the esophagus. In one particular embodiment, the temperature setting is adjusted based on the operator-selected power setting. In another particular embodiment, the flow rate setting is adjusted based on the operator-selected power setting. In another particular embodiment, the temperature setting and the flow rate setting are adjusted based on the operator-selected power setting. In another embodiment, if the temperature sensor detects that the esophageal tissue adjacent to the ablation site is approaching a temperature at which lesion(s) form in esophageal tissue, the temperature setting and/or the flow rate setting is adjusted to cause the temperature of that esophageal tissue to return toward a temperature at which lesion(s) do not form.

C. SYSTEMS

In one aspect, the present disclosure provides a system for preventing or reducing the risk of thermal injury to esophageal tissue of a patient during a cardiac tissue ablation procedure. In certain embodiments, the system includes a tissue ablation device, an esophageal heat transfer device, and a controller. The controller provides, via a power source, power to the tissue ablation device to perform the cardiac tissue ablation procedure at an ablation site of cardiac tissue of the patient. Further, the controller provides, via a fluid source, fluid to the esophageal heat transfer device to enable a heat transfer region of the esophageal heat transfer device to regulate a temperature of a portion of an esophagus next to the ablation site during the cardiac tissue ablation procedure.

In certain embodiments, the controller is communicatively coupled to the power source and the power source is electrically coupled to an ablation element of the tissue ablation device. To perform a cardiac tissue ablation, the tissue ablation device is at least partially inserted into the left atrium of the patient. Further, the ablation element is positioned near an ablation site in the left atrium of the patient. The tissue ablation device is configured to be activated via the controller when the ablation element is positioned near the ablation site. For example, an operator selects a power setting (e.g., between about 5 Watts and 50 Watts) of the ablation device via the controller. In certain embodiments, the controller sends a signal to cause the power source to provide power to the ablation element of the tissue ablation device at the operator-selected power setting. For example, the controller and the power source enable the tissue ablation device to remain activated at the operator-selected power setting throughout the cardiac tissue ablation procedure. Further, in certain embodiments, the tissue ablation device remains activated at the operator-selected power setting throughout the cardiac tissue ablation procedure. That is, in such examples, the operator-selected power setting is a constant value that remains unchanged throughout the cardiac tissue ablation procedure.

In certain embodiments, the controller is communicatively coupled to a fluid source and the fluid source is fluidly coupled to a fluid path of the esophageal heat transfer device. The esophageal heat transfer device is configured to be positioned at least partially within an esophagus of the patient to control the temperature of at least esophageal tissue during a cardiac tissue ablation procedure. For example, the esophageal heat transfer device includes one or more lumens defining the fluid path that is configured to provide the fluid to a heat transfer region of the esophageal heat transfer device. The heat transfer region is configured to add heat to or extract heat from esophageal tissue adjacent to an ablation site. In certain embodiments, the heat transfer region extends from about 1 centimeter to about 15 centimeters along a length of the esophageal heat transfer device to enable the esophageal heat transfer device to transfer heat in a localized manner.

In certain embodiments, the esophageal heat transfer device includes (i) a location sensing element configured to identify esophageal tissue adjacent to the ablation site of the cardiac tissue, (ii) a pressure sensor configured to measure a current pressure applied to the esophageal tissue adjacent to the ablation site during the cardiac tissue ablation procedure, and/or (iii) a temperature sensor configured to measure a current temperature of the esophageal tissue adjacent to the ablation site when the heat transfer region is in contact with that esophageal tissue. The sensing elements of the esophageal heat transfer device are communicatively coupled to the controller to enable the controller to control the fluid source based upon the measurements collected by the sensing elements. In certain embodiments, the location sensing element includes a magnetic coil, an acoustic transducer, a thermal imaging element, and/or any other sensing element configured to detect the location of the ablation site, the esophageal tissue adjacent to the ablation site, and/or a tissue ablation device performing the tissue ablation procedure. Further, in certain embodiments, the tissue ablation device includes a location sensing element, such as a magnetic coil and/or an acoustic transducer, to facilitate the esophageal heat transfer device in being positioned near the esophageal tissue adjacent to the ablation site.

In certain embodiments, the controller determines a temperature setting and/or a flow rate setting of the fluid provided to the heat transfer region of the esophageal heat transfer device that is to prevent or reduce the risk of lesion(s) and/or other damage from forming on the esophageal tissue adjacent to the ablation site during the cardiac tissue ablation procedure. For example, the controller determines the temperature setting and/or the flow rate setting based on the current temperature, the current pressure, other esophageal data, the operator-selected power setting, and/or any other data that affects the formation of lesion(s) on the esophagus. In one particular embodiment, the controller determines the temperature setting based on the operator-selected power setting. In another particular embodiment, the controller determines the flow rate setting based on the operator-selected power setting. In another particular embodiment, the controller determines the temperature setting and the flow rate setting based on the operator-selected power setting. Further, the controller causes the fluid source to provide the fluid to the esophageal heat transfer device in accordance with the temperature setting and/or the flow rate setting. In certain embodiments, if the temperature sensor detects that the esophageal tissue adjacent to the ablation site is approaching a temperature at which lesion(s) form in esophageal tissue, the controller causes the fluid source to adjust the temperature setting and/or the flow rate setting of the fluid provided to the esophageal heat transfer device to cause the temperature of the esophagus to return toward a target temperature at which lesion(s) do not form. In certain embodiments, the controller adjusts the combination of the temperature setting and the flow rate setting for a duration of the cardiac tissue ablation procedure to prevent or reduce the risk of lesion(s) throughout the cardiac tissue ablation procedure.

In one aspect, the present disclosure provides a system for preventing or reducing the risk of thermal injury to esophageal tissue of a patient during a cardiac tissue ablation procedure. In certain embodiments, the system includes an esophageal heat transfer device and a controller.

The esophageal heat transfer device includes a heat transfer region and a non-contact temperature sensor that is physically separated from the heat transfer region and is configured to measure a current temperature of the esophageal tissue adjacent to the ablation site when the heat transfer region is in contact with that esophageal tissue.

The temperature sensor of the esophageal heat transfer device is communicatively coupled to the controller to enable the controller to control a fluid source based upon the esophageal tissue temperature detected by the temperature sensor. In certain embodiments, the controller is communicatively coupled to a fluid source and the fluid source is fluidly coupled to a fluid path of the esophageal heat transfer device.

In certain embodiments, the system is configured to adjust a temperature setting and/or a flow rate setting of a fluid source, which provides fluid to the heat transfer region of the esophageal heat transfer device, to prevent or reduce the risk of lesions and/or other damage to esophageal tissue during the cardiac tissue ablation procedure. That is, the temperature setting and/or the flow rate setting of the fluid source can be adjusted during the cardiac tissue ablation procedure to control the temperature and/or flow rate of the fluid provided by the fluid source to the heat transfer region. In certain embodiments, the temperature setting and/or the flow rate setting is adjusted based on the esophageal tissue temperature detected by the temperature sensor. For example, if the temperature sensor detects that the esophageal tissue adjacent to the ablation site is approaching a temperature at which lesion(s) form, the temperature setting and/or the flow rate setting is adjusted to control the temperature and/or flow rate of the fluid flowing from the fluid source to the heat transfer region, which in turn causes the temperature of that esophageal tissue to return toward the target temperature (i.e., a temperature at which lesion(s) do not form).

In certain embodiments, the system is configured to adjust the amount of energy (in a radiofrequency ablation procedure) or the temperature of the ablation fluid (in a cryoablation procedure) used in the ablation procedure. In some such embodiments, a higher ablation energy or a cooler ablation fluid may be used because simultaneous measurement and management of adjacent esophageal tissue protects such tissue from damage.

In certain embodiments of any aspect of the present technology disclosed herein, the outer wall (e.g., a tissue-contacting outer wall) of the heat transfer device comprises a material with high thermal conductivity. In some such embodiments, the temperature of the esophageal tissue adjacent to the ablation site is essentially the same as the thermally conductive outer wall. Thus, in certain embodiments, measurement of a current temperature of the esophageal tissue adjacent to the ablation site can be achieved by measuring the temperature of outer wall.

D. EXEMPLARY EMBODIMENTS

A1: A method for preventing or reducing the risk of thermal injury to esophageal tissue of a patient during a cardiac tissue ablation procedure, the method comprising (a) activating, via a controller, a tissue ablation device at an operator-selected power setting, the tissue ablation device being positioned at an ablation site of cardiac tissue of the patient; (b) positioning an esophageal heat transfer device within an esophagus of the patient, the esophageal heat transfer device including a heat transfer region positioned within the esophagus near the ablation site of the cardiac tissue and one or more lumens that provide fluid to the heat transfer region; (c) optionally, collecting esophageal data via one or more sensing elements; (d) selecting, based on the esophageal data and/or the operator-selected power setting, a temperature setting and/or a flow rate setting for the fluid flowing through the esophageal heat transfer device to maintain a target temperature of esophageal tissue adjacent to the ablation site via the heat transfer region; and (e) adjusting, via the controller, a fluid source to provide the fluid to the esophageal heat transfer device in accordance with the temperature setting and/or the flow rate setting.

A2: The method of embodiment A1, further including: positioning the tissue ablation device next to the ablation site; positioning the esophageal heat transfer device within the esophagus such that the heat transfer region of the esophageal heat transfer device contacts the esophageal tissue adjacent to the ablation site; and contacting the tissue ablation device to the ablation site to perform ablation of the cardiac tissue at the ablation site.

A3: The method of any one of embodiments A1-A2, further including deactivating, via the controller, the esophageal heat transfer device in response to the tissue ablation device being deactivated.

A4: The method of any one of embodiments A1-A3, further including: detecting a position of the tissue ablation device relative to the esophageal heat transfer device; and identifying the esophageal tissue adjacent to the ablation site based upon the position of the tissue ablation device.

A5: The method of embodiment A4, further including detecting a position of the tissue ablation device and/or the esophageal heat transfer device via magnetic coils of the esophageal heat transfer device and/or the tissue ablation device.

A6: The method of embodiment A4, further including detecting a position of the tissue ablation device relative to the esophageal heat transfer device via acoustic transducers of the esophageal heat transfer device and/or the tissue ablation device.

A7: The method of any one of embodiments A1-A6, further including identifying the esophageal tissue adjacent to the ablation site via a thermal imaging element of the esophageal heat transfer device.

A8: The method of any one of embodiments A1-A7, wherein the esophageal data includes a current temperature of the esophageal tissue adjacent to the ablation site and the one or more sensing elements includes a temperature sensor to measure the current temperature.

A9: The method of any one of embodiments A1-A8, wherein the esophageal data includes a current pressure applied by the esophageal heat transfer device onto the esophageal tissue adjacent to the ablation site and the one or more sensing elements includes a pressure sensor to measure the current pressure.

A10: The method of any one of embodiments A1-A9, further including determining the temperature setting and/or the flow rate setting further based on a duration of time the ablating energy is applied to the ablation site and/or the contact force applied to the ablation site by the ablation catheter.

A11: The method of any one of embodiments A1-A10, wherein the ablation is radiofrequency ablation.

A12: The method of any one of embodiments A1-A11, wherein the ablation is cryoablation.

A13: The method of any one of embodiments A1-A12, wherein the tissue ablation device remains activated at the operator-selected power setting throughout the cardiac tissue ablation procedure.

A14: The method of embodiment A13, wherein the operator-selected power setting is a constant value that remains unchanged throughout the cardiac tissue ablation procedure.

A15: The method of any one of embodiments A1-A14, wherein the temperature setting and/or the flow rate setting is adjusted during the cardiac tissue ablation procedure to prevent or reduce the risk of a lesion from forming at the esophageal tissue adjacent to the ablation site.

A16: The method of any one of embodiments A1-A15, wherein the esophageal data is collected, the temperature setting is determined, and the temperature of the fluid provided to the esophageal heat transfer device is adjusted for a duration of the cardiac tissue ablation procedure.

A17: The method of any one of embodiments A1-A16, wherein the operator-selected power setting is between about 5 Watts and 50 Watts.

B1: A system for preventing or reducing the risk of thermal injury to esophageal tissue of a patient during a cardiac tissue ablation procedure, the system comprising (a) an esophageal heat transfer device comprising (i) a heat transfer region configured to transfer heat to esophageal tissue adjacent to an ablation site of cardiac tissue; (ii) one or more lumens defining a fluid path to provide fluid to the heat transfer region; (iii) a location sensing element to identify the esophageal tissue adjacent to an ablation site; and (iv) optionally, a temperature sensor configured to measure a current temperature of the esophageal tissue adjacent to the ablation site when the heat transfer region is in contact with the esophageal tissue adjacent to the ablation site; and (b) a controller configured to determine and/or adjust a temperature setting and/or a flow rate setting of the fluid provided to the heat transfer region.

B2: The system of embodiment B1, further including a pressure sensor configured to measure a current pressure applied to the esophageal tissue adjacent to the ablation site during the cardiac tissue ablation procedure, wherein the combination of the temperature setting and the flow rate setting further is adjusted based on the current pressure.

B3: The system of any one of embodiments B1-B2, wherein the location sensing element consists from the group consisting of a magnetic coil, an acoustic transducer, and a thermal imaging element.

B4: The system of any one of embodiments B1-B3, wherein the heat transfer region has a surface area from about 2 square millimeters to about 100 square millimeters.

B5: The system of any one of embodiments B1-B4, wherein the heat transfer region includes an intra-esophageal balloon through which the fluid flows to transfer heat.

B6: The system of any one of embodiments B1-B5, wherein the heat transfer device includes an exterior surface and an insulating layer extending along a first portion of the exterior surface to define the heat transfer region at a second portion of the exterior surface, wherein the second portion is uninsulated.

B7: The system of embodiment B6, wherein the insulating layer includes a pocket of air.

B8: The system of embodiment B7, wherein the insulating layer includes a thick layer of tubing.

B9: The system of embodiment B6, wherein the exterior surface forms a snug fit with an esophageal wall to stabilize a position of the heat transfer region within the esophagus of the patient.

B10: The system of embodiment B9, further including an inflatable portion to enable the exterior surface to form the snug fit with the esophageal wall.

B11: The system of embodiment B9, further including an outer diameter that enables the exterior surface to form the snug fit with the esophageal wall.

B12: The system of any one of embodiments B1-B11, wherein the temperature sensor is embedded in or attached to the esophageal heat transfer device.

C1: A system for preventing or reducing the risk of thermal injury to esophageal tissue of a patient during a cardiac tissue ablation procedure, the system comprising (a) an esophageal heat transfer device comprising (i) a heat transfer region configured to transfer heat to esophageal tissue adjacent to an ablation site of cardiac tissue; (ii) one or more lumens defining a fluid path to provide fluid to the heat transfer region; (iii) a location sensing element to identify the esophageal tissue adjacent to an ablation site; and (iv) optionally, a temperature sensor configured to measure a current temperature of the esophageal tissue adjacent to the ablation site when the heat transfer region is in contact with the esophageal tissue adjacent to the ablation site; and (b) a controller configured to determine and/or adjust a temperature setting and/or a flow rate setting of the fluid provided to the heat transfer region.

C2: The system of embodiment C1, wherein the temperature sensor is an infrared temperature sensor, preferably a charge-coupled device.

D1: A heat transfer device, the device comprising (a) a tube having an outer wall, the outer wall at least partially defining a lumen for flow of a heat transfer medium; (b) a heat transfer region comprising at least a portion of the outer wall; and (c) a non-contact temperature sensor configured to sense temperature of patient tissue adjacent to the heat transfer region, wherein the temperature sensor is physically separated from the heat transfer region.

D2: The device of embodiment D1, wherein the temperature sensor does not substantially impact heat transfer between the heat transfer region and the patient tissue adjacent to the heat transfer region.

E1: A heat transfer device, the device comprising (a) a tube having an outer wall, the outer wall at least partially defining a lumen for flow of a heat transfer medium, wherein the outer wall is configured to contact patient tissue; (b) a support surface disposed within the lumen; and (c) a temperature sensor mounted to or embedded in the support surface, wherein the sensor is configured to sense temperature of a tissue in contact with the outer wall.

E2: A multi-lumen heat transfer device, the device comprising (a) a tube having an outer wall, wherein the outer wall is configured to contact patient tissue; (b) a plurality of lumens separated by at least one inner common support wall; and (c) a temperature sensor mounted to or embedded in the at least one inner common support wall, wherein the sensor is configured to sense temperature of a tissue in contact with the outer wall.

E3: The device of any one of embodiments E1-E2, wherein the temperature sensor does not substantially impact heat transfer across the outer wall.

E4: The device of any one of embodiments D1-D2 or E1-E3, wherein the temperature sensor is an infrared sensor.

E5: The device of any one of embodiments D1-D2 or E1-E4, wherein the temperature sensor comprises one or more charge-coupled device.

E6: The device of any one of embodiments D1-D2 or E1-E5, wherein the temperature sensor comprises a plurality of charge-coupled devices.

E7: The device of embodiment E6, wherein the plurality of charge-coupled devices are arranged in an array.

E8: The device of any one of embodiments D1-D2 or E1-E6, wherein the temperature sensor comprises one or more micro-electro-mechanical systems.

E9: The device of any one of embodiments D1-D2 or E1-E6 or E8, wherein the temperature sensor comprises a plurality of micro-electro-mechanical systems.

E10: The device of embodiment E9, wherein the plurality of micro-electro-mechanical systems are arranged in an array.

E11: The device of any one of embodiments D1-D2 or E1-E10, wherein the tube comprises at least one marker visible to a visualization instrument.

E12: The device of embodiment E11, wherein the marker is a radiopaque marker or electromagnetic marker.

F1: A method for simultaneously measuring and managing temperature of esophageal tissue susceptible to damage during a cardiac ablation procedure, the method comprising positioning the device of any one of the preceding claims into the esophagus of a patient and, optionally, adjusting a temperature management parameter based on signals produced by the temperature sensor.

F2: The method of embodiment F1, wherein the temperature management parameter is temperature of esophageal tissue adjacent to an atrium, preferably a left atrium of a heart.

F3: The method of embodiment F1, wherein the temperature management parameter is temperature of the heat transfer medium.

F4: The method of any one of embodiments F1-F3, wherein the cardiac ablation procedure is a radiofrequency ablation procedure.

F5: The method of any one of embodiments F1-F3, wherein the cardiac ablation procedure is a cryoablation procedure.

E. FIGURES

Turning to the figures, FIG. 1 illustrates an example ablation system 100 in accordance with the teachings herein. As illustrated in FIG. 1, the ablation system 100 includes a controller 102, an ablation device 104 (also referred to as a tissue ablation device), a power source 106 for the ablation device 104, an esophageal heat transfer device 108, and a fluid source 110 for the esophageal heat transfer device 108.

In the illustrated example, the controller 102 includes a processor and memory. The processor may be any suitable processing device or set of processing devices such as, but not limited to, a microprocessor, a microcontroller-based platform, an integrated circuit, one or more field programmable gate arrays (FPGAs), and/or one or more application-specific integrated circuits (ASICs). The memory may be volatile memory (e.g., RAM including non-volatile RAM, magnetic RAM, ferroelectric RAM, etc.), non-volatile memory (e.g., disk memory, FLASH memory, EPROMs, EEPROMs, memristor-based non-volatile solid-state memory, etc.), unalterable memory (e.g., EPROMs), read-only memory, and/or high-capacity storage devices (e.g., hard drives, solid state drives, etc.). In certain embodiments, the memory includes multiple kinds of memory, particularly volatile memory and non-volatile memory. The memory is computer readable media on which one or more sets of instructions, such as the software for operating the methods of the present disclosure, can be embedded. The instructions may embody one or more of the methods or logic as described herein. For example, the instructions reside completely, or at least partially, within any one or more of the memory, the computer readable medium, and/or within the processor during execution of the instructions.

The terms "non-transitory computer-readable medium" and "computer-readable medium" include a single medium or multiple media, such as a centralized or distributed database, and/or associated caches and servers that store one or more sets of instructions. Further, the terms "non-transitory computer-readable medium" and "computer-readable medium" include any tangible medium that is capable of storing, encoding or carrying a set of instructions for execution by a processor or that cause a system to perform any one or more of the methods or operations disclosed herein. As used herein, the term "computer readable medium" is expressly defined to include any type of computer readable storage device and/or storage disk and to exclude propagating signals.

In the illustrated example, the controller 102 includes an ablation controller 112 and an esophageal controller 114. The ablation controller 112 is configured to control operation of the ablation device 104, and the esophageal controller 114 is configured to control operation of the esophageal heat transfer device 108. For example, the ablation controller 112 is communicatively coupled to the power source 106 (e.g., via a wired or wireless connection) and the power source 106 is electrically coupled to an ablation element 116 (e.g., a tip electrode) of the ablation device 104 to enable the ablation controller 112 to control operation of the ablation device 104 via the power source 106. Further, the esophageal controller 114 is communicatively coupled to the fluid source 110 (e.g., via a wired or wireless connection) and optional sensing element(s) of the esophageal heat transfer device 108 and the fluid source 110 is fluidly coupled to fluid path(s) of the esophageal heat transfer device 108 to enable the esophageal controller 114 to control operation of the esophageal heat transfer device 108 via the fluid source 110 based on data collected by the sensing element(s) of the esophageal heat transfer device 108. The fluid source 110 may be a heat exchanger, such as any of a variety of conventionally designed heat exchangers (e.g., an Arctic Sun Temperature Management System (Bard Medical), a Medi-Therm III Conductive Hyper/Hypothermia System (Gaymar/Stryker), a Blanketrol II or Blanketrol III Hyper-Hypothermia System (Cincinnati Sub-Zero), or equivalent units). In certain embodiments, the fluid source 110 may operate to provide the fluid via negative pressure. The fluid may be a gas, such as, for example, nitrous oxide, Freon, carbon dioxide, or nitrogen. Alternatively, the fluid may be a liquid, such as, for example, water, saline, propylene glycol, ethylene glycol, or mixtures thereof. In particular examples, the fluid is water or saline. In other examples, the fluid may be a gel, such as, for example, a refrigerant gel. In other examples, the fluid may be formed, for example, by mixing a powder with a liquid. Thus, it should be understood that combinations and/or mixtures of the above-mentioned media may be employed to achieve a heat transfer medium according to the present technology.

As illustrated in FIG. 1, the ablation device 104 includes an ablation element 116 that is configured to ablate tissue of a patient via radiofrequency (RF) ablation, cryoablation, and/or other ablation procedure(s). For example, the ablation controller 112 includes an input device (e.g., a control knob, an instrument panel, a touchscreen, a button, a touchpad) that enables an operator to select power setting for the ablation device 104. For example, the operator-selected power setting has a maximum range from about 5 Watts to about 50 Watts. The ablation controller 112 sends a signal to the power source 106. The power source 106 provides power to the ablation element 116 of the ablation device 104 at the operator-selected power setting in response to receiving the corresponding signal from the ablation controller 112. Further, in certain embodiments, the ablation device 104 includes an optional camera 118 and/or other sensing device to identify a location of an ablation site. Additionally or alternatively, the ablation device 104 includes a location sensing element 120 (e.g., a magnetic coil, an acoustic transducer) that enables the location of the ablation device 104 to be identified. For example, the ablation device may include one or more magnetic coils (e.g., one, two, or three magnetic coils) that enable the location of the ablation device 104 to be identified. In certain embodiments, the ablation device 104 includes one or more ring electrodes 122.

Figure 2A:
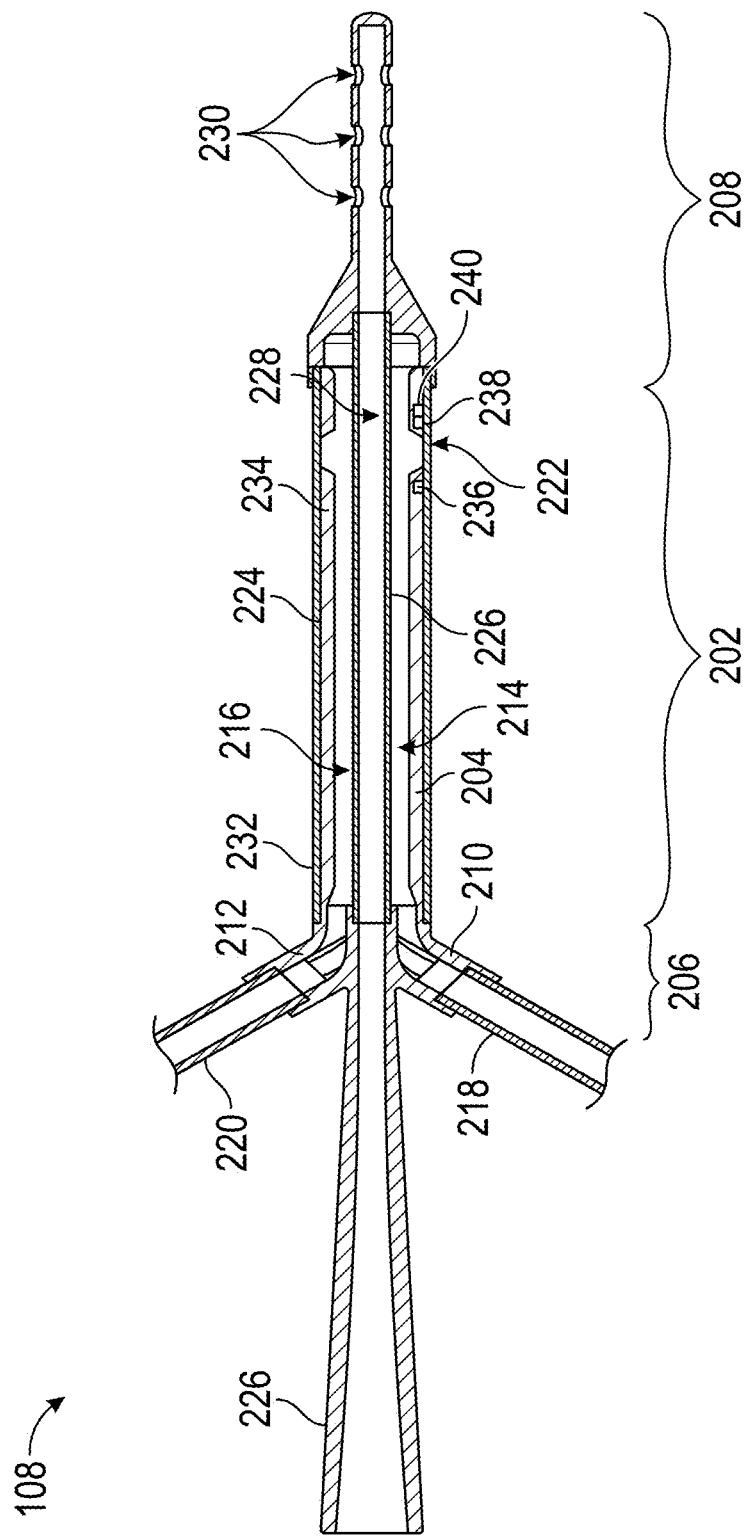
FIG. 2A illustrates an exemplary esophageal heat transfer device.

The esophageal heat transfer device 108 of the illustrated example includes one or more lumens (e.g., a supply lumen 214 of FIG. 2A, a return lumen 216 of FIG. 2A) that define a fluid path for fluid to travel to and from a heat transfer region (e.g., a heat transfer region 222 of FIG. 2A). Further, esophageal heat transfer device 108 includes optional sensing element(s) to collect esophageal data of the esophagus of the patient and/or location data of the esophageal heat transfer device 108. For example, the esophageal controller 114 collects the data from a location sensing element (e.g., a magnetic coil, an acoustic transducer, a thermal imaging element) of the esophageal heat transfer device 108 to identify a location of the esophageal heat transfer device 108 relative to the ablation site, the esophageal tissue adjacent to the ablation site, and/or the ablation device 104. Additionally or alternatively, the esophageal heat transfer device 108 includes a location sensing element (e.g., a magnetic coil, an acoustic transducer) that enables the location of the esophageal heat transfer device 108 to be identified (e.g., in relation to the ablation device and/or esophageal tissue identified as at risk for injury). For example, the esophageal heat transfer device may include one or more magnetic coils (e.g., one, two, or three magnetic coils) that enable the location of the esophageal heat transfer device 108 to be identified.

Further, the esophageal controller 114 of the illustrated example collects the esophageal data from one or more of the sensing element(s) of the esophageal heat transfer device 108. In certain embodiments, the esophageal controller 114 collects other data (e.g., the operator-selected power setting for the ablation device 104, a duration of time for the application of ablating energy to the ablation site, and/or the contact force applied to the ablation site by the ablation catheter) that affect the transfer of heat between esophageal tissue of the patient and the esophageal heat transfer device 108. Based upon the collected data, the esophageal controller 114 determines a temperature setting and/or a flow rate setting for the fluid flowing along a fluid path in the esophageal heat transfer device 108 that enables esophageal tissue adjacent to the ablation site to maintain a target temperature. For example, lesion(s) do not form along a portion of an esophagus that has a temperature from about 37° C. to about 50° C. In certain embodiments, the target temperature is a specific value. In other examples, the target temperature is a range of values. Upon determining the temperature setting and/or the flow rate setting, the esophageal controller 114 sends a signal to the fluid source 110. In turn, the fluid source 110 provides fluid to the fluid path of the esophageal heat transfer device 108 in accordance with the temperature setting and the flow rate setting. For example, based upon the collected esophageal data, the esophageal controller 114 causes the fluid source 110 to adjust the temperature setting and/or the flow rate setting of the fluid provided to the esophageal heat transfer device 108 during the ablation procedure to cause the temperature of esophageal tissue, particularly esophageal tissue adjacent to the ablation site, to remain at and/or return toward a target temperature at which lesion(s) do not form.

Additionally or alternatively, the ablation device and/or the esophageal heat transfer device includes a location sensing element (e.g., a magnetic coil, an acoustic transducer) that enables the location of the ablation device 104 relative to the esophageal heat transfer device 108 to be identified.

FIG. 2A illustrates an example of the esophageal heat transfer device 108 of FIG. 1. In the illustrated example, the esophageal heat transfer device 108 includes a heat transfer body 202 that includes an internal cavity 204. Further, the esophageal heat transfer device 108 of the illustrated example includes a proximal end 206 and a distal end 208. The heat transfer body 202 extends between the proximal end 206 and the distal end 208. The esophageal heat transfer device 108 also includes an inlet port 210 and an outlet port 212. The inlet port 210 is fluidly connected to a supply lumen 214 of the esophageal heat transfer device 108, and the outlet port 212 is fluidly connected to a return lumen 216 of the esophageal heat transfer device 108. The supply lumen 214 and the return lumen 216 are in fluid communication with each other, thereby defining a fluid path for flow of a fluid and/or heat transfer medium through the esophageal heat transfer device 108.

As illustrated in FIG. 2A, the inlet port 210 is configured to connect to an inflow tube 218, and the outlet port 212 is configured to connect to an outflow tube 220. For example, the inflow tube 218 and the outflow tube 220 are coupled to the fluid source 110 to receive fluid from and return fluid to the fluid source 110. Thus, the inflow tube 218 and the outflow tube 220 fluidly connect the fluid source 110 and the esophageal heat transfer device 108 to enable the fluid to flow between the fluid source 110 and the esophageal heat transfer device 108 to heat or cool a heat transfer region 222 of the esophageal heat transfer device 108. That is, the supply lumen 214 and the return lumen 216 define the fluid path to enable the fluid to flow to the heat transfer region 222, and the heat transfer region 222 adds heat to or extracts heat from the esophagus of the patient (e.g., the esophageal tissue adjacent to the ablation site). For example, when the inflow tube 218 is coupled to the inlet port 210 and the outflow tube 220 is coupled to the outlet port 212, the fluid flows from the fluid source 110, through the inflow tube 218 and into the supply lumen 214 to heat or cool a patient via the fluid at the heat transfer region 222. Further, the fluid flows from the supply lumen 214, through the return lumen 216, and to the outflow tube 220 to circulate the fluid back to the fluid source 110.

The esophageal heat transfer device 108 is configured for placement within an esophagus of a patient undergoing a cardiac tissue ablation procedure. The distal end 208 of the esophageal heat transfer device 108 is configured for insertion into a body orifice. For example, the distal end 208 of the esophageal heat transfer device 108 is configured for insertion into the nostrils, mouth, anus, or urethra of a patient. When properly inserted, the distal end 208 of the esophageal heat transfer device 108 is ultimately positioned within an esophagus and/or other anatomical structure that is susceptible to damage during cardiac tissue ablation procedure(s). Upon insertion of the esophageal heat transfer device 108 into the patient (e.g., via nostrils or mouth), the heat transfer body 202 of the esophageal heat transfer device 108 is configured to directly contact esophageal tissue of the patient. For example, when the esophageal heat transfer device 108 is inserted into the esophagus of the patient, at least a portion of the heat transfer body 202 directly contacts the esophageal epithelium of the patient. In the illustrated example, the heat transfer body 202 includes flexible tubing 224 and is generally located between the distal end 208 and the proximal end 206. In other examples, the heat transfer body 202 is defined by the flexible tubing 224 and the distal end 208 of the esophageal heat transfer device 108.

In certain embodiments, the esophageal heat transfer device 108 also includes an optional gastric access tube 226 that defines a gastric access lumen 228 and extends to the distal end 208 of the esophageal heat transfer device 108. Further, the esophageal heat transfer device 108 includes one or more ports 230 along the side of the gastric access tube 226. In the illustrated example, the one or more ports 230 are located along the gastric access tube 226 at the distal end 208 of the esophageal heat transfer device 108. The one or more ports 230 may provide for communication between the space exterior to the esophageal heat transfer device 108 and the gastric access lumen 228. For example, the one or more ports 230 may act as a portal between the patient's stomach and the gastric access lumen 228 allowing the gastric contents to be suctioned from the patient's stomach out through the gastric access lumen 228. The presence of one or more ports 230 provides reduced likelihood of blockage of the gastric access lumen 228 from semi-solid stomach contents. Alternatively, multiple gastric access lumens may be employed. The addition of one or more ports 230 may improve and enhance the removal of stomach contents, which, in turn, may improve contact between gastric mucosa and the heat transfer body 202 of the esophageal heat transfer device 108. Such improved contact may enhance heat transfer between the esophageal heat transfer device 108 and the gastric mucosa and, thus, enhance heating or cooling of the patient. The configuration of the ports 230 shown in FIG. 2 is oval. However, the ports 230 can be, for example, circular, rectangular, or any other shape that permits flow of gastric contents from the stomach to the gastric access lumen 228.

As illustrated in FIG. 2A, the esophageal heat transfer device 108 includes an exterior surface 232. For example, the heat transfer body 202 includes an exterior surface 232 of the flexible tubing 224. Further, an insulating layer 234 extends along a portion (e.g., a first portion) of the exterior surface 232 of the heat transfer body 202 to define the heat transfer region 222 along another portion (e.g., a second portion) of the exterior surface 232. For example, the insulating layer 234 includes material that substantially impedes heat transfer between esophageal tissue of the patient and the fluid flowing through the esophageal heat transfer device 108. The insulating layer 234 is absent from (i.e., not located at) the heat transfer region 222 to facilitate heat transfer between the esophagus of the patient and the fluid flowing through the esophageal heat transfer device 108 at the heat transfer region 222. In certain embodiments, the insulating layer 234 includes a thick layer of tubing to insulate the fluid of the esophageal heat transfer device 108. Additionally or alternatively, the insulating layer 234 includes a pocket of air that insulates the fluid of the esophageal heat transfer device 108. In the illustrated example, the heat transfer region 222 defined by the insulating layer 234 has a substantially small surface area to enable the esophageal heat transfer device 108 to add heat to or extract heat from the esophagus of the patient in a localized manner. For example, the length of the heat transfer region 222 may be less than the length of the esophagus of the patient. In certain embodiments, the heat transfer region 222 is from about 1 centimeter to about 15 centimeters in length along the heat transfer body 202, alternatively from about 2 centimeters to about 10 centimeters in length along the heat transfer body 202, alternatively from about 3 centimeters to about 7 centimeters in length along the heat transfer body 202, or alternatively from about 4 centimeters to about 6 centimeters in length along the heat transfer body 202. Further, in certain embodiments, the heat transfer body 202 has an outer diameter than enables the exterior surface 232 of the esophageal heat transfer device 108 to form a snug fit with a wall of the esophagus of the patient to stabilize a position of the heat transfer region 222 within the esophagus of the patient.

The esophageal heat transfer device 108 of the illustrated example also includes a temperature sensor 236, a pressure sensor 238, and a location sensing element 240 positioned at and/or near the heat transfer region 222. For example, the temperature sensor 236 is configured to measure a temperature of esophageal tissue of the patient when the heat transfer region 222 is in contact with an esophageal wall. Further, the pressure sensor 238 is configured to measure a pressure applied by the esophageal heat transfer device 108 onto esophageal tissue of the patient. For example, when the heat transfer region 222 is in contact with esophageal tissue that is adjacent to an ablation site of the cardiac tissue of the patient, the temperature sensor 236 is configured to measure the current temperature of that esophageal tissue (e.g., while optionally allowing for heat transfer through the sensor) and the pressure sensor 238 is configured to measure the current pressure applied to the esophageal tissue. Additionally or alternatively, the esophageal heat transfer device 108 includes any other type of sensing element configurable to collect esophageal data that the esophageal controller 114 may use to determine the temperature setting and/or the flow rate setting for the fluid flowing from the fluid source 110 into the esophageal heat transfer device 108. Further, the location sensing element 240 is configured to identify the esophageal tissue adjacent to the ablation site and/or the position of the heat transfer device 108. For example, the location sensing element 240 facilitates an operator in positioning the heat transfer region 222 of the esophageal heat transfer device 108 near the ablation device 104, the ablation site of the cardiac tissue, and/or the esophageal tissue adjacent to the ablation site. In certain embodiments, the location sensing element 240 is a thermal imaging element utilized to collect image(s) that enable an operator to identify the esophageal tissue adjacent to the ablation site based upon that esophageal tissue relative to the temperature(s) of other portions of the esophagus. As another example, the location sensing element 240 is a magnetic coil that can create a received signal in response to a magnetic field generated by a magnetic field source to determine a position of the esophageal heat transfer device 108. As yet another example, the location sensing element 240 is an acoustic transducer configured to emit acoustic waves and further configured to receive a pulse-echo reflection of the signal and communicate the signal to a processor to determine the position of the ablation device 104 relative to the esophageal heat transfer device 108.

In certain embodiments, the esophageal heat transfer device 108 is manufactured via an extrusion or over-molding process. For example, utilizing extrusion or over-molding processes to form the esophageal heat transfer device 108 may eliminate the need to seal junctions or affix end caps and reduce the points at which leaks may occur. In a particular embodiment, the manufacturing process comprises an over-molding process, which may reduce, minimize, or eliminate leak points. In certain embodiments, the flexible tubing 224 and the gastric access tube 226 are integrally formed via extrusion. In other examples, the flexible tubing 224 is formed via extrusion, the gastric access tube 226 is formed separately via extrusion, and the gastric access tube 226 is subsequently inserted into the internal cavity 204 defined by the flexible tubing 224.

Figure 2B:
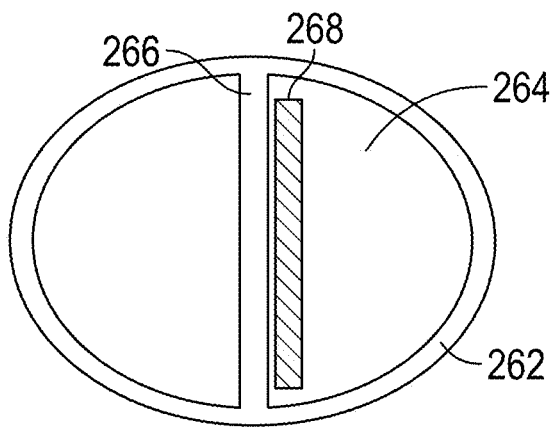
FIG. 2B illustrates a cross section of an exemplary heat transfer device.

FIG. 2B is a cross-sectional view of an exemplary esophageal heat transfer device having an outer wall 262 that at least partially defines a lumen 264 for flow of a heat transfer medium. Lumen 264 is also defined by interior support wall 266. A non-contact temperature sensor 268, which may be, for example, an infrared temperature sensor, is mounted to or embedded in interior support wall 266. Upon placement in a patient's esophagus, at least a portion of outer wall 262 is in thermal contact with the patient's esophageal tissue. Thus, temperature sensor 268 is physically separated (e.g., by lumen 264 and outer wall 262) from a portion of the outer wall 262 that is in thermal contact with the patient's esophageal tissue.

Figure 3:
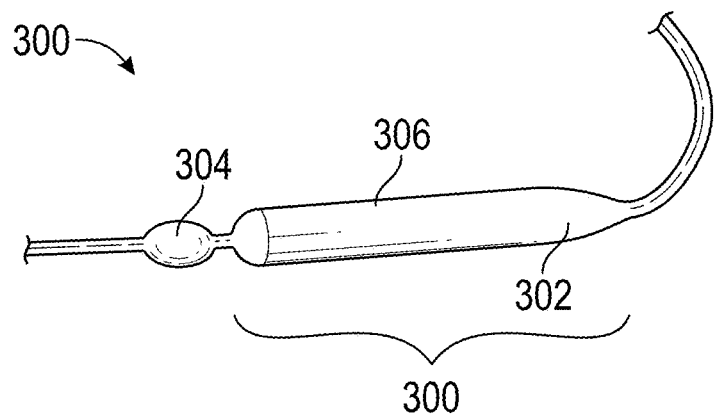
FIG. 3 illustrates another exemplary esophageal heat transfer device.

FIG. 3 illustrates another example of the esophageal heat transfer device. In the illustrated example, the heat transfer region 300 of the esophageal heat transfer device includes a first balloon 302. For example, the first balloon 302 can be inflated with fluid. In certain embodiments, the first balloon 302 (i.e., an inflatable portion) enables the exterior surface 306 of the esophageal heat transfer device to form a snug fit with a wall of the esophagus of the patient. Further, the esophageal heat transfer device of the illustrated example includes an anchoring balloon 304 that stabilizes the position of the heat transfer region 300 within the esophagus of the patient. For example, the anchoring balloon 304 anchors the esophageal heat transfer device to a stomach of the patient to position the heat transfer region 300 within the esophagus of the patient.

Figure 4:
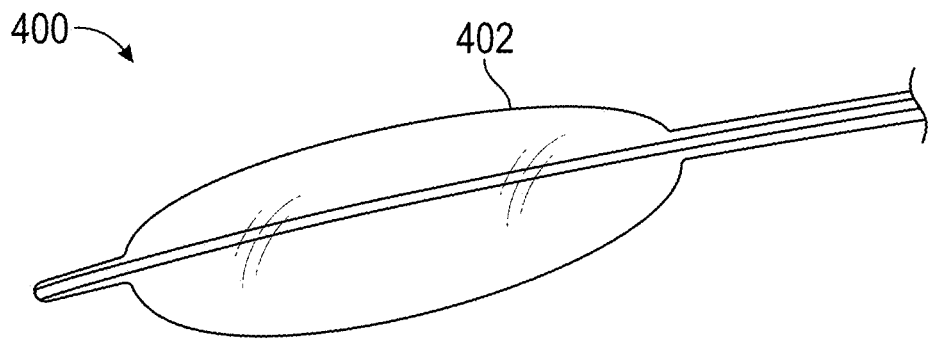
FIG. 4 further illustrates a portion of another exemplary esophageal heat transfer device.

FIG. 4 further illustrates the heat transfer region 400 of another example of the esophageal heat transfer device. In the illustrated example, the heat transfer region 400 includes a balloon 402. For example, the balloon 402 is a compliant intra-esophageal balloon through which saline and/or other fluid flows to transfer heat between the esophageal heat transfer device and esophageal tissue of the patient. In certain embodiments, warm saline and/or other fluid flows through the balloon 402 of the heat transfer region 400 of the esophageal heat transfer device to warm esophageal tissue (e.g., the esophageal tissue adjacent to a cryoablation site). In other examples, cold saline and/or other fluid flows through the balloon 402 to cool esophageal tissue (e.g., the esophageal tissue adjacent to the radiofrequency ablation site). In certain embodiments, balloon 402 (i.e., an inflatable portion) forms a snug fit with a wall of the esophagus of the patient. In certain embodiments, the length of balloon 402 is from about 1 centimeter to about 15 centimeters, alternatively from about 3 centimeters to about 7 centimeters, or alternatively from about 4 centimeters to about 6 centimeters and thereby provides localized heat transfer between the esophageal heat transfer region 400 and a portion of the patient's esophagus.

Figure 5:
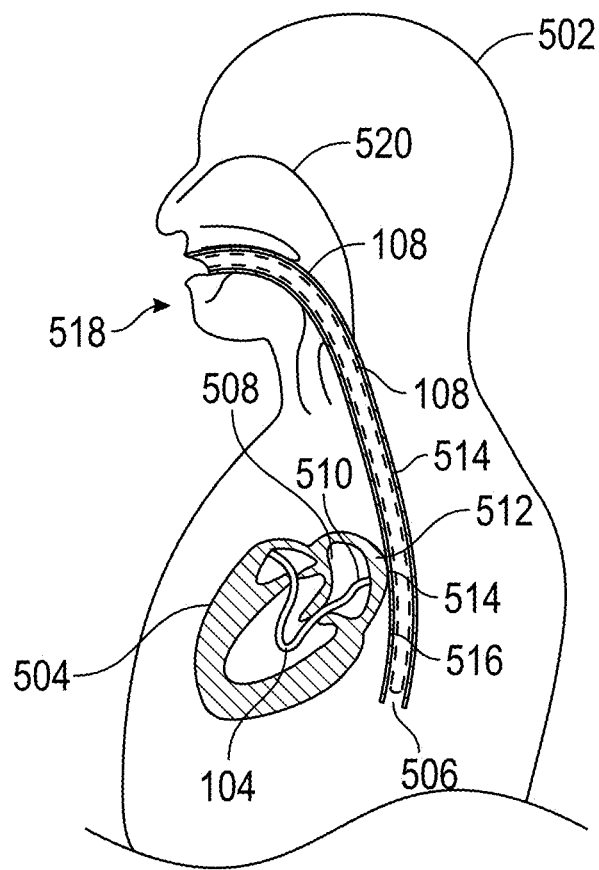
FIG. 5 depicts an exemplary esophageal heat transfer device and an ablation device inserted into a patient.

FIG. 5 depicts the ablation device 104 and the esophageal heat transfer device 108 of the ablation system 100 inserted into a patient 502. More specifically, FIG. 5 depicts the ablation device 104 inserted into a heart 504 of the patient 502 and the esophageal heat transfer device 108 inserted into an esophagus 506 of the patient 502.

In the illustrated example, the ablation device 104 is inserted into a left atrium 508 of the heart 504 of the patient such that the ablation element 116 (not shown in FIG. 5) of the ablation device 104 is in contact with an ablation site 510 in the atrial wall 512 of the patient 502. For example, the ablation site 510 is identified by an operator of the ablation system 100 based upon image(s), such as those obtained by fluoroscopy or from electroanatomic mapping systems and/or video captured by the camera 118 of the ablation device 104.

As illustrated in FIG. 5, the esophageal heat transfer device 108 is inserted into the esophagus 506 of the patient 502 such that the heat transfer region (not shown in FIG. 5) is in contact with a portion 514 of an esophageal wall 516 of the esophagus that is next to the ablation site 510 of the atrial wall 512. In the illustrated example, the portion 514 of the esophageal wall 516 contacts, directly or indirectly via a pericardial fibrofatty layer, and/or is otherwise positioned near the ablation site 510 such that heat applied to the ablation site 510 by the ablation device 104 transfers, at least partially, to the portion 514 of the esophageal wall 516. In certain embodiments, the operator of the ablation system 100 utilizes the location sensing element 240 of the esophageal heat transfer device 108 to identify and position the heat transfer region near the portion 514 of the esophageal wall 516, the ablation site 510, and/or the ablation device 104. Further, in the illustrated example, the esophageal heat transfer device 108 is inserted through a mouth 518, past a pharynx 520, and into the esophagus 506 of the patient 502. Additionally or alternatively, the esophageal heat transfer device 108 is configured to be inserted into the esophagus 506 via nostrils of the patient 502.

Figure 6:
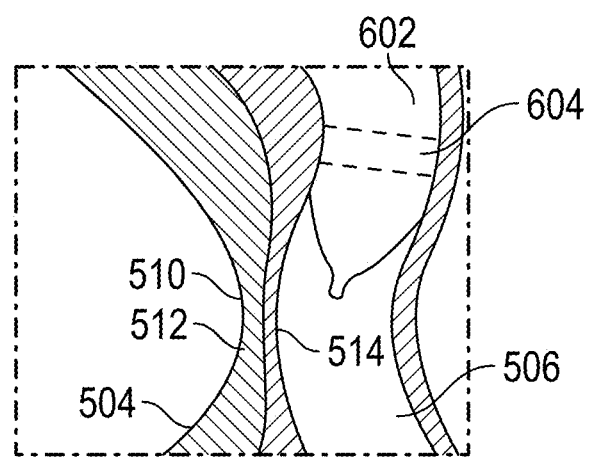
FIG. 6 further depicts the exemplary esophageal heat transfer device inserted into the patient of FIG. 5.

FIG. 6 further depicts a portion of an exemplary esophageal heat transfer device 602 inserted into the esophagus 506 of the patient 502. In the illustrated example, the heat transfer region 604 of the esophageal heat transfer device 602 is approaching the portion 514 of the esophageal wall 516 that is next to the ablation site 510 of the atrial wall 512 of the heart 504.

Figure 7:
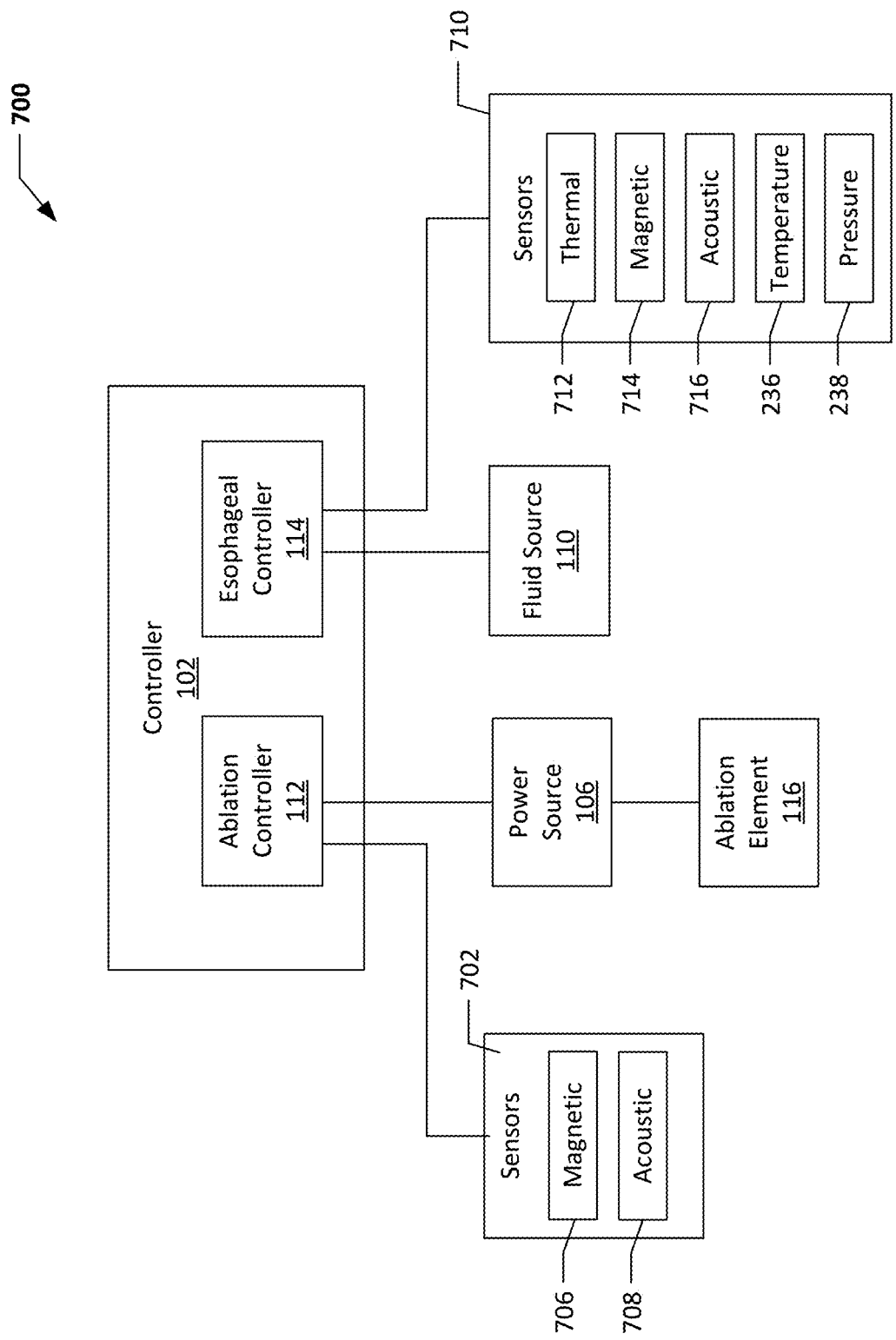
FIG. 7 is a block diagram of electronic components of the ablation system of FIG. 1.

FIG. 7 is a block diagram of electronic components 700 of the ablation system 100. As illustrated in FIG. 7, the controller 102 includes the ablation controller 112 and the esophageal controller 114.

The ablation controller 112 of the illustrated example is communicatively coupled to sensing elements 702 of the ablation device 104. For example, the sensing elements 702 include a magnetic coil 706, an acoustic transducer 708, and/or any other type of location sensing element(s) that facilitates an operator in positioning the ablation element 116 of the ablation device 104 relative to the ablation site 510. The ablation controller 112 also is communicatively coupled to the power source 106 to instruct the power source 106 to provide the operator-selected power setting to the ablation element 116 of the ablation device 104.

The esophageal controller 114 of the illustrated example is communicatively coupled to sensing elements 710 of the esophageal heat transfer device 108. For example, the sensing elements 710 include a thermal imaging element 712, a magnetic coil 714, an acoustic transducer 716, and/or any other type of location sensing element(s) that facilitates an operator in positioning the heat transfer region of the esophageal heat transfer device 108 relative to the ablation site 510, the portion 514 of the esophageal wall 516 next to the ablation site 510, and/or the ablation device 104. Further, the sensing elements 710 include the temperature sensor 236 that is configured to measure a current temperature of the portion 514 of the esophageal wall 516 next to the ablation site 510 and the pressure sensor 238 that is configured to measure a current pressure that is applied onto the portion 514 of the esophageal wall 516 next to the ablation site 510. Additionally or alternatively, the sensing elements 710 include any other type of sensing element(s) configured to collect esophageal data of the esophagus 506 that facilitates the esophageal controller 114 in determining the temperature setting and/or the flow rate setting for the fluid flowing through the esophageal heat transfer device 108. The esophageal controller 114 also is communicatively coupled to the fluid source 110 to instruct the fluid source 110 to provide the fluid to the esophageal heat transfer device 108 in accordance with the temperature setting and/or the flow rate setting.

Figure 8:
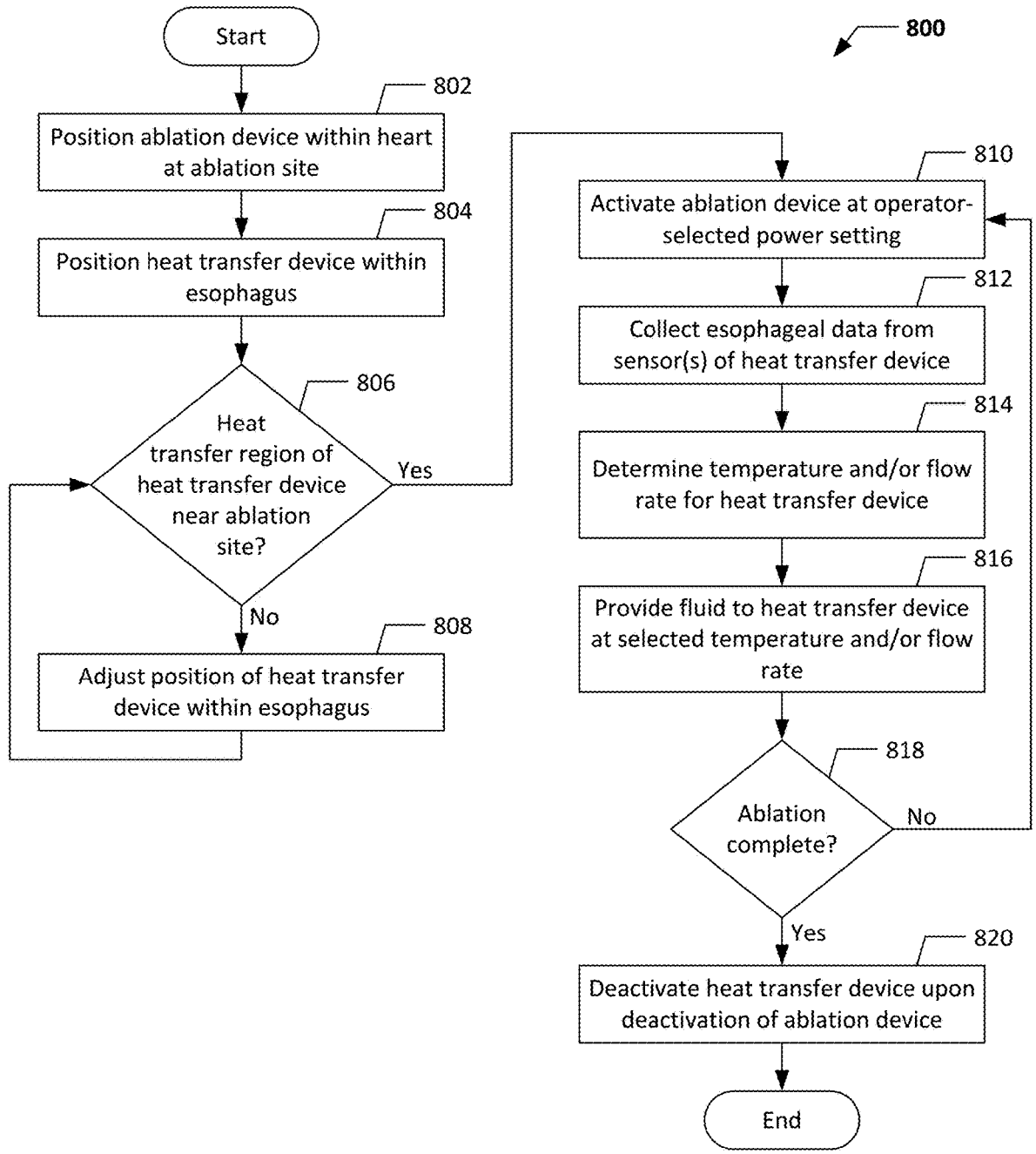
FIG. 8 is a flowchart for protecting esophageal tissue of a patient via an esophageal heat transfer device during a cardiac ablation procedure in accordance with the teachings herein.

FIG. 8 is a flowchart of an exemplary method 800 to protect esophageal tissue of a patient via an esophageal heat transfer device during a cardiac ablation procedure. The flowchart of FIG. 8 is representative of machine readable instructions that are stored in memory and include one or more programs which, when executed by a processor, cause the ablation controller 112, the esophageal controller 114, and/or, more generally, the controller 102 of FIGS. 1 and 7. While the example program is described with reference to the flowchart illustrated in FIG. 8, many other methods of implementing the example controller 102 may alternatively be used. For example, the order of execution of the blocks may be rearranged, changed, eliminated, and/or combined to perform the method 800. Further, because the method 800 is disclosed in connection with the components of FIGS. 1-7, some functions of those components will not be described in detail below.

Initially, at block 802, the ablation device 104 is positioned within the heart 504 of the patient 502 at and/or near the ablation site 510 of the atrial wall 512. For example, the ablation device 104 is positioned such that the ablation element 116 of the ablation device 104 contacts and/or is next to the ablation site 510. At block 804, the esophageal heat transfer device 108 is positioned within the esophagus 506 of the patient 502.

At block 806, it is determined whether the heat transfer region 222 of the esophageal heat transfer device 108 is positioned near the ablation site 510 such that the heat transfer region 222 of the esophageal heat transfer device 108 is in contact with the portion 514 of the esophageal wall 516 next to the ablation site 510 of the atrial wall 512. In certain embodiments, the relative location of the portion 514 of the esophageal wall 516 is identified via the thermal imaging element 712 of the esophageal heat transfer device 108. For example, the portion 514 of the esophageal wall 516 next to the ablation site 510 is warmer or colder than other portions of the esophagus 506 during an ablation procedure. Further, in certain embodiments, the position of the ablation device 104 relative to the esophageal heat transfer device 108 is detected and the relative position of the portion 514 of the esophageal wall 516 next to the ablation site 510 is identified based upon the relative position of the ablation device 104 that is located at the ablation site 510. For example, the position of the ablation device 104 is detected via the magnetic coil 706 of the ablation device 104. As another example, the position of the ablation device 104 relative to the esophageal heat transfer device 108 is detected via the acoustic transducers 708, 716 of the ablation device 104 and the esophageal heat transfer device 108, respectively.

In response to it being determined that the heat transfer region 222 of the esophageal heat transfer device 108 is not near and/or in contact with the portion 514 of the esophageal wall 516 next to the ablation site 510, the method 800 proceeds to block 808 at which the position of the esophageal heat transfer device 108 is adjusted within the esophagus 506. Otherwise, in response to it being determined that the heat transfer region 222 of the esophageal heat transfer device 108 is near and/or in contact with the portion 514 of the esophageal wall 516 next to the ablation site 510, the method 800 proceeds to block 810.

At block 810, the ablation controller 112 activates the ablation device 104 at an operator-selected power setting. Further, the ablation element 116 of the ablation device 104 is placed in contact with to the ablation site 510 to ablate a portion of the atrial wall 512. For example, the ablation element 116 is placed in contact with the ablation site 510 when the ablation device 104 is activated at the operator-selected power setting to perform radiofrequency ablation. In certain embodiments, the ablation device 104 remains activated at the operator-selected power setting throughout the ablation procedure. In some such embodiments, the operator-selected power setting is a constant value (e.g., between about 5 Watts and 50 Watts) that remains unchanged throughout the ablation procedure.

At block 812, the esophageal controller 114 collects esophageal data from one or more of the sensing elements 710 of the esophageal heat transfer device 108 positioned within the esophagus 506 of the patient 502. For example, the collected esophageal data includes a current temperature of the portion 514 of the esophageal wall 516 next to the ablation site 510 that is measured via the temperature sensor 236 of the esophageal heat transfer device 108 and/or a current pressure applied onto the portion 514 of the esophageal wall 516 next to the ablation site 510 (e.g., by the esophageal heat transfer device 108) that is measured by the pressure sensor 238 of the esophageal heat transfer device 108.

At block 814, the esophageal controller 114 determines, based upon the collected esophageal data, the operator-selected power setting, a duration of time for the application of ablating energy to the ablation site, and/or the contact force applied to the ablation site by the ablation catheter, a temperature and/or a flow rate of the fluid provided to the esophageal heat transfer device 108 by the fluid source 110 to enable the heat transfer region 222 to maintain a target temperature of the portion 514 of the esophageal wall 516 next to the ablation site 510 to prevent or reduce the risk of lesion(s) from forming on the esophagus 506 during the ablation procedure without substantially interfering with the ability to obtain a durable lesion. In a particular embodiment, the esophageal controller 114 determines the temperature and/or the flow rate based on the operator-selected power setting, a duration of time that the ablating energy is applied to the ablation site, and/or the contact force applied to the ablation site by the ablation catheter.

At block 816, the esophageal controller 114 causes the fluid source 110 to provide the fluid to the esophageal heat transfer device 108 in accordance with the selected temperature and/or flow rate. At block 818, the controller 102 determines whether the ablation procedure is complete.

In response to the controller 102 determining that the ablation procedure is not complete, the method 800 returns to block 810 to enable the esophageal controller 114 to maintain the portion 514 of the esophageal wall 516 next to the ablation site 510 at the target temperature. For example, during the ablation procedure, the esophageal controller 114 adjusts the fluid source 110 to provide the fluid to the esophageal heat transfer device 108 at an adjusted temperature and/or flow rate. The temperature and/or the flow rate is adjusted by the esophageal controller 114 during the ablation procedure to prevent or reduce the risk of lesion(s) from forming at the portion 514 of the esophageal wall 516 next to the ablation site 510.

Returning to block 818, in response to the controller 102 determining that the ablation procedure is complete, the method 800 proceeds to block 820. At block 820, the esophageal controller 114 deactivates the esophageal heat transfer device 108 in response to detecting that the ablation device 104 has been deactivated.

F. EXAMPLES

The following examples are merely illustrative, and not limiting to this disclosure in any way.

Example 1. Swine Model

Methods

Design. This prospective interventional study was performed by an experienced team that included a practicing electrophysiologist and assistant professor of cardiology, with input and contribution from an additional two practicing university-based electrophysiologists, under a protocol approved by the Institutional Animal Care and Use Committee (IACUC) of American Preclinical Services, Minneapolis, MN The study utilized methods consistent with current veterinary and USDA standards, with a state-of-the-art, Association for Assessment and Accreditation of Laboratory Animal Care (AAALAC) International-accredited vivarium. Animal care and handling was in accord with Office of Laboratory Animal Welfare guidance for humane care and use of animals and with regulations outlined in the USDA Animal Welfare Act (9 CFR Parts 1, 2 and 3) and the conditions specified in the Guide for the Care and Use of Laboratory Animals (National Academy Press, Washington DC, 1996). A swine model of the size chosen has similarity in size, physiology, and thoracic anatomy to typical adult patients undergoing ablation for the prevention of atrial fibrillation.

Procedures. A total of six male Yorkshire swine weighing a mean of 81.5 kg±7 kg, housed on site, were given 12 hours food restriction but free access to water before the intervention. Subjects were medicated with a pre-anesthetic mix of Telazol (tiletamine/zolazepam)/Xylazine 3.5-5.5 mg/kg intramuscularly, endotracheally intubated and anesthetized with 3% inhalational isoflurane (with concentration adjusted as needed to maintain anesthesia). No paralytics were used during any part of the study. Normal saline was instilled at a maintenance rate (2 cc/kg/hr) via ear vein. Continuous cardiac monitoring was performed with a 3-lead EKG rhythm recorder.

Intervention. An exemplary esophageal heat transfer device was placed following standard procedure. Briefly, the device was connected to an external heat exchange unit (either a Medi-Therm III, Stryker Corp., Kalamazoo, MI, or a Thermotek Harmony, Thermotek Inc., Flower Mound, TX), both of which circulate distilled water as the coolant at a temperature range from 4° C. to 42° C. with a flow rate of 115 L/hour or 60 L/hour, respectively. After water flow was initiated, the tip of the device was lubricated with a water soluble lubricant and inserted through the oropharynx into the esophagus to a depth sufficient for the tip to rest beyond the thoracic esophagus.

Lesion Placement. In each subject, a right lateral thoracotomy was performed exposing a region of esophagus. A range of 6 to 10 ablations, based on esophageal length, were placed directly on the esophagus. A 4 mm ablation catheter (Safire 7Fr Quadripolar Catheter, St. Jude Medical, St. Paul, MN) was used, powered by an RF generator (IBI 1500T9 RF, Irvine Biosciences Inc., Irvine, CA). Ablation energy was set at 10 W, with a 30-45 second duration. In one lesion, 20 W was utilized. Contact force was measured on the first lesion to gauge pressure requirements (15 g), and subsequent lesions were performed manually by an experienced electrophysiologist physician.

Control lesions were performed with 37° C. water held still with no flow within the device (i.e., with no water circulation). Treatment lesions were performed with cooled water (range 5° C.-37° C.) circulating within the device at two different flow rates. Each subject received a combination of control and treatment lesions. The presence of mucosal lesions was evaluated visually after triphenyltetrazolium chloride (TTC) staining and thermal injury depth was measured by target tissue histology, performed by a DVM and Diplomate, American College of Veterinary Pathologists. Descriptive statistics are reported with comparisons of means via independent sample t-tests.

Results

A total of 52 ablations were performed across 6 swine (average mass 81.5±7 kg). Six (6) ablations were used to validate experimental parameters. A total of 46 ablations were included for analysis, 23 treatment and 23 control. All ablations performed under control 142 conditions produced external esophageal lesions. Transmural lesions extending into the esophageal mucosa were consistently visible on gross examination after 30 seconds of 10 W RF energy application in subjects less than 80 kg. In subjects greater than 80 kg, transmural lesions were obtained in at least 20% of cases with 30 seconds duration and 70% of cases with a 45 seconds duration.

In contrast, ablations performed under treatment conditions using 10 W of RF energy using 37° C., 10° C., or 5° C. circulating water, for 30 or 45 seconds duration, did not produce visible transmural lesions and only 6 ablations (25%) produced visible external lesions. Ablations performed during the most aggressive treatment condition (5° C. circulating water), did not demonstrate any visible lesions throughout the thickness of the esophageal musculature, including on the external surface of the esophagus at the point of contact with the ablation catheter.

Figure 9:
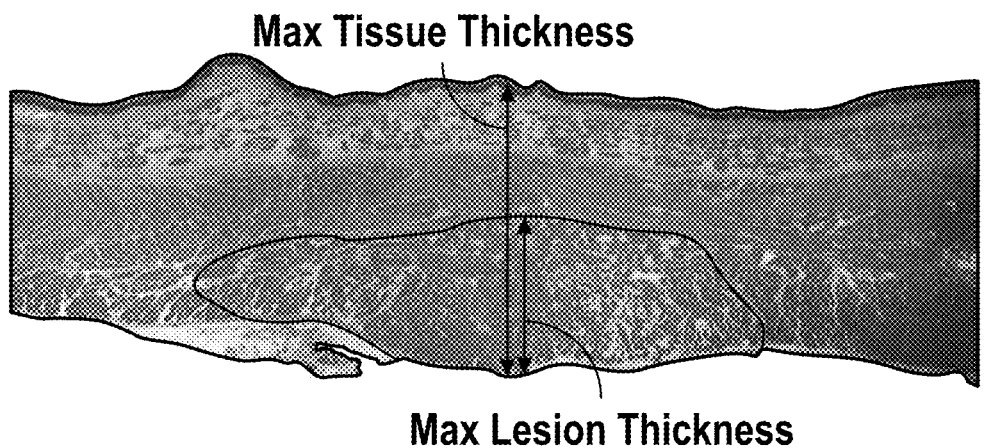
FIG. 9 depicts histopathological evaluation of lesioned esophageal tissue where Max Tissue Thickness includes the entire thickness of the tissue on the slide at the site of measurement and Max Lesion Thickness includes the thickness of the lesion starting at the adventitial connective tissue and going toward the epithelium to the maximum depth of the lesion damage. Measurement lines are illustrated separately for visual clarity but were taken at the same location for data collection to ensure accurate measurements for percentage calculation.
Figure 10:
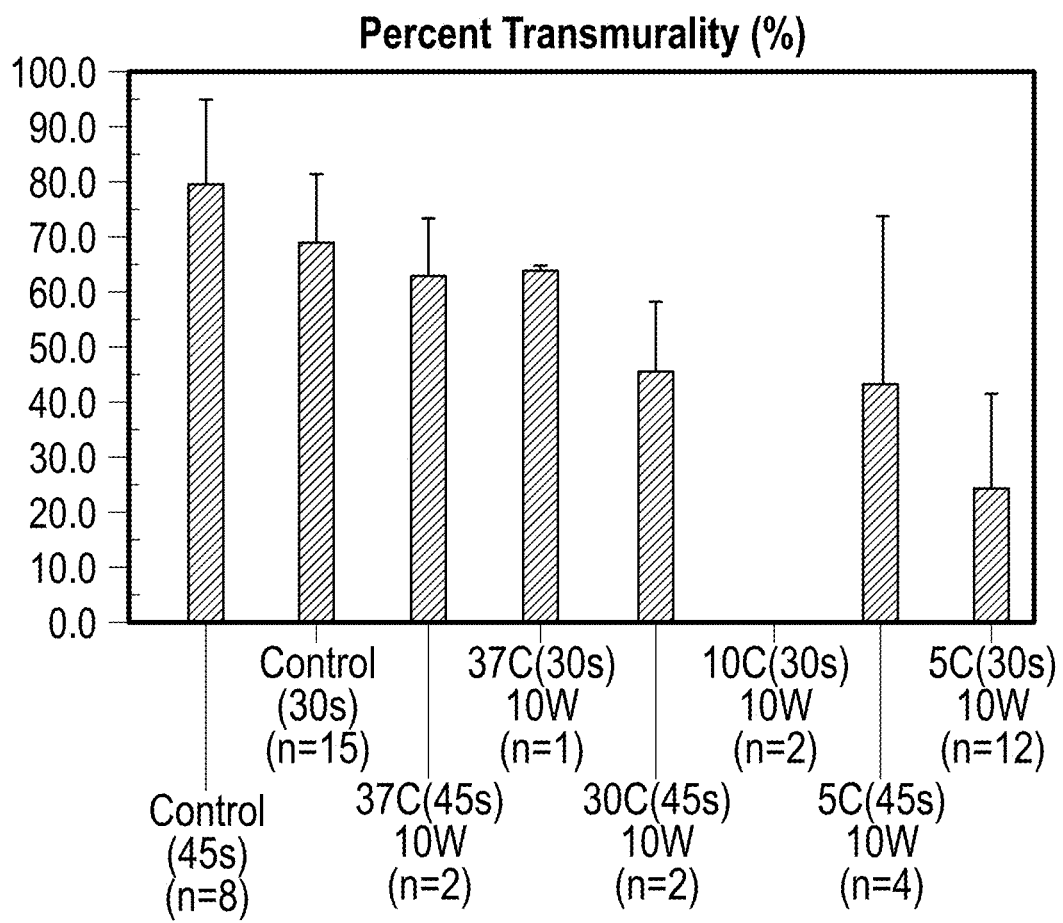
FIG. 10 shows a graphical representation of histopathological evaluation described in FIG. 9. Percent lesion depth (transmurality) for each group is shown by operational parameters (power, duration, water temperature).

Histopathological evaluation was performed with the measurement method as shown in FIG. 9, in which the maximum lesion thickness was determined, and divided by the maximum tissue thickness. Measurements of lesion thickness confirmed that the percent transmurality of lesions decreased as water temperature flowing through the esophageal heat transfer device was decreased (Table 1A). FIG. 10 shows a graphical representation of results. No lesions were identifiable in the region of RF ablations during cooling with 10° C. water flow and 30 seconds of duration using 10 W of power. The absolute reduction in percent transmurality from control (45 seconds of application) with the use of 37° C. water was 16.0% (p=0.2), while the absolute reduction with the use of 30° C. water was 33.6% (p=0.02) and the absolute reduction using 5° C. water was 35.6% (p=0.02). In the group with 30 seconds of RF application time, the absolute reduction in percent transmurality from control with the use of 37° C. water was 5.1% (p=0.7), while the absolute reduction with the use of 10° C. water was 69.7% (p<0.001) and the absolute reduction using 5° C. water was 44.5% (p<0.001). Mean submucosal edema scores, muscularis mucosa damage scores, and epithelial damage scores likewise decreased with decreases in coolant temperature (and hence increases in heat extraction capacity). See Table 1B.

rates of coolant. A finite element model investigating the effects of a cooled intra-esophageal balloon suggested that this approach could be a viable method to prevent thermal injury to the esophagus during intraoperative ablation of the left atrium, with authors suggesting that the temperature of the cooling fluid has a more significant effect on the minimization of the lesion than the rate of cooling, but actual

TABLE 1A

Histopathology findings summarized by experimental group.

| Group | # of lesions | Energy (W) | Duration (sec) | Cooling Temp (° C.) | Transmurality (%) | Std Dev (± %) | Significance (p value) |
|---|---|---|---|---|---|---|---|
| Control – 45 s | 8 | 10 | 45 | N/A | 79.9 | 0.0 | Ref |
| Control – 30 s | 15 | 10 | 30 | N/A | 69.7 | 0.0 | Ref |
| Cool_37 – 45 s | 2 | 10 | 45 | 37 | 64.0 | 0.0 | 0.20 |
| Cool_37 – 30 s | 1 | 10 | 30 | 37 | 64.6 | N/A | 0.70 |
| Cool_30 – 45 s | 2 | 10 | 45 | 30 | 46.3 | 0.0 | 0.02 |
| Cool_10 – 45 s | 2 | 10 | 45 | 10 | 0.0 | N/A | <0.001 |
| Cool_05 – 45 s | 4 | 10 | 45 | 5 | 44.4 | 30.4 | 0.02 |
| Cool_05 – 30 s | 12 | 10 | 30 | 5 | 25.2 | 0.0 | <0.001 |

TABLE 1B

Histopathology findings summarized by experimental group.

| Group | # of lesions | Energy (W) | Duration (sec) | Cooling Temp (° C.) | Myofiber contraction band necrosis score (mean) | Submucosal edema score (mean) | Muscularis mucosa damage score (mean) | Epithelial damage score (mean) |
|---|---|---|---|---|---|---|---|---|
| Control – 45 s | 8 | 10 | 45 | N/A | 3.4 | 1.3 | 1.1 | 0.4 |
| Control – 30 s | 15 | 10 | 30 | N/A | 2.9 | 0.7 | 0.3 | 0.1 |
| Cool_37 – 45 s | 2 | 10 | 45 | 37 | 2.8 | 0.0 | 0.0 | 0.0 |
| Cool_37 – 30 s | 1 | 10 | 30 | 37 | 3.0 | 0.0 | 0.0 | 0.0 |
| Cool_30 – 45 s | 2 | 10 | 45 | 30 | 1.5 | 0.0 | 0.0 | 0.0 |
| Cool_10 – 45 s | 2 | 10 | 45 | 10 | 0.0 | 0.0 | 0.0 | 0.0 |
| Cool_05 – 45 s | 4 | 10 | 45 | 5 | 0.8 | 0.0 | 0.0 | 0.0 |
| Cool_05 – 30 s | 12 | 10 | 30 | 5 | 0.7 | 0.0 | 0.0 | 0.0 |

Scores: (0) = none; (1) = minimal; (2) = mild; (3) = moderate; (4) = severe

The data presented in this Example suggest a significant protective capability of an esophageal cooling device against esophageal injury from the application of RF energy ablation. Using a water temperature of 5° C. supplied to the device by either of two models of heat exchanger (supplying a flow rate of 60 L/hour or 115 L/hour), a direct application of RF energy at 10 W for 30 seconds was unable to elicit visual evidence of thermal impact. In contrast, under control conditions without water flow through the device, this same energy resulted in fully transmural lesions visible on gross pathology. Even at a coolant temperature of 37° C., a protective effect was seen, suggesting that high coolant flow rates may be an important component of this effect.

Previous work in the area of esophageal protection via direct cooling has in general utilized significantly lower flow rates were represented by convection coefficient estimation rather than raw coolant flow. Subsequent studies using an agar phantom-based model found that this method was able to provide effective thermal protection, although it was noted that the method could fail under certain conditions; however a coolant flow rate of only 25 mL per minute was used, which likely significantly limits the capability to extract heat effectively (as contrasted with the esophageal cooling device evaluated which utilized a flow of water at over 60 liters per hour, or more than 1000 mL per minute). Further studies by this same group utilized varying coolant temperatures between 5° C. and 37° C. but maintained the coolant flow rate at 25 mL per minute, resulting in the conclusion that it is possible to thermally protect esophageal tissue (including the transmural region 2 mm away from the mucosal surface) utilizing a coolant temperature of 5° C. or less. Of note, the temperatures measured at the inlet and outlet of the cooling circuit were 4.9±0.3° C. and 13.6±0.3° C., respectively, a difference of over 8° C., in contrast to only an average increase of 0.3° C. with the current esophageal heat transfer device.

A custom developed system utilizing temperature controlled saline or water circulating at a flow rate between 50 to 300 mL per minute and a temperature of 5 to 25° C. was evaluated using an in vitro lamb heart and esophagus preparation, followed by an in vivo model with six dogs. This custom system consisted of a 12 French probe with a distal expandable compliant latex sack with a diameter of up to 3 cm fully expanded. The authors found that a circulating water temperature of 25° C. failed to spare esophageal tissue from thermal injury. However lowering the circulating temperature to 10° C. or 5° C. spared thermal injury (although expanding the balloon diameter by increasing circulating volume displaced the esophagus towards the left atrium and allowed the development of shallow esophageal injury to the external layers of the muscularis).

A clinical study of eight patients used a closed loop system with low flow rates (25 mL/min) and a water temperature of 4.5° C. found that without cooling, esophageal temperature increased from a baseline of 36.4° C. up to 40.5° C. in under 30 seconds during ablation, whereas with the esophageal cooling balloon, esophageal temperature decreased down to 30.2° C. with the balloon in place, and allowed an increase in temperature to only 33.5° C. The authors conclude that luminal esophageal temperature during the left atrial ablation was lowered by esophageal cooling using their catheter to a level where no thermal damage to esophageal tissue would likely be induced. A study presented in 2007 in abstract form described the use of a saline filled esophageal balloon to attempt esophageal protection in an animal model, and found that in four dogs, a non-flowing saline solution of 10° C. was not sufficient to prevent thermal injury.

Free water instillation into the esophagus has been tried with varying success. A study of 100 patients used very small volumes (5 mL) of ice water as the instilled volume, which was injected prior to RF energy delivery, and subsequently when esophageal temperatures reached 42° C. The authors found that this approach alleviated the severity of esophageal lesions, but did not reduce the incidence: lesions occurred in 20% of the experimental group, and 22% of the controls, with 3 moderate and 7 mild in the cooled group and 3 severe, 1 moderate, and 7 mild in the control. Another study utilized an infusion of cooled saline mixed with Gastrografin or Iopamidol, with slightly higher, but still limited volumes (10-20 mL in repeated injected aliquots with a temperature of approximately 10° C.). A total of 318 patients were randomized between groups receiving only temperature monitoring without cooling, temperature monitoring with cooling when temperature exceeded 43° C., and temperature monitoring with cooling received when temperatures exceeded 39° C. The percentage of patients free from any ulceration or erosion in each group was found to be 63.6%, 87.5%, and 95.2%, respectively, and the authors conclude that esophageal damage can be reduced by infusing cooling solution into the esophagus via a gastric tube when luminal temperature exceeds 39° C. during ablation.

Collectively, these data from prior investigations into esophageal protection via direct cooling suggest that although some efficacy was apparent, a limitation stemmed from the lower, or absent, flow rates of coolant employed. Additionally, it was noted in one paper that the methods previously investigated were somewhat complicated to perform in clinical practice, and thus no follow-up studies were conducted. In contrast, the esophageal heat transfer device evaluated in this study is straightforward to deploy without disruption in typical workflow in the electrophysiology lab.

The study described in this Example did not utilize a contact-force sensing catheter to measure applied force at each lesion. The first application utilized force measurement with an external gauge, while all subsequent lesions relied on the judgement of an experienced electrophysiologist. Although some variability in contact force is inevitable with this approach, a systematic bias is unlikely, and the effect sizes identified are such that they would likely overwhelm. Likewise, in lieu of irrigation supplied through the tip of the ablation catheter, saline was used as a water bath during ablations; however, this likely provides a more severe thermal insult to the tissue than would be the case with irrigation. This study did not involve ablation of the atria directly; however the design utilized (ablating directly on the esophagus) provided a worst-case model that eliminates confounders such as variations between patients in location of the esophagus relative to the atria, variations in the amount of interspersed tissue, and variations in atrial wall thickness, all of which would confound the data.

In addition, the prior investigations into esophageal protection via direct cooling did not assess the impact of cooling on the quality of the atrial lesion (i.e., the interplay between achieving a durable ablation while simultaneously protecting esophageal tissue during a cardiac ablation). Furthermore, the essentially static operating parameters of previous approaches precluded detailed investigation into the impact of lesion formation in the atrium. Indeed, as mentioned above, use of a cooling balloon could reduce the possibility of achieving a transmural lesion in the atrium, particularly in cases where the atrium is of considerable thickness, and when using a short duration and a low target temperature. See Berjano & Hornero, *Phys Med Biol* 2005, 50(20):N269-279.

In conclusion, use of an esophageal cooling device resulted in significant protection against esophageal injury from direct radiofrequency ablation. The protective effects seen in this data suggest that this may be an effective approach to the prevention of esophageal injury during RF ablation of atrial fibrillation.

Example 2

A reliable mathematical model was derived to describe the effects seen experimentally above, in order to establish a framework from which to guide further analysis and development of this new esophageal protective strategy.

Mathematical modeling software was used to build a 2D model of esophageal injury. The model was compared to the experimentally-derived data from the above animal model utilizing direct application of RF energy to exposed esophagus.

The modeling governing equations utilized mass, momentum and energy balances, with the boundary conditions defined by the experimental values for temperatures of the ablation catheter tip, cooling water and patient animal. Additional inputs were the heat capacity, density and thermal conductivity of the esophagus and cooling device walls, and the dynamic viscosity and ratio of specific heats for the water domain.

RF ablation utilizes two electrodes for application: one corresponds to the catheter at certain wattage and the other serves as a ground reference. The ground electrode is generally embedded within a patch and placed on the patient's back during the RF ablation, while the catheter is taken to the desired place of action in the atrium for application on the myocardium at the inner wall. Due to the electrode's positioning, a simplification of the thoracic cavity allows accurate modeling of the RF energy distribution in the body and, consequently, of the tissue's heating.

The geometries which serve as computational domains for the different models evaluated were considered in 2D in the sagittal plane, because the most relevant heat changes occur in this plane.

Direct Application of RF to Esophagus

This section includes the problem formulation, model implementation and comparison between both simulated and experimental results for RF ablation directly on the esophagus.

Figure 11A:
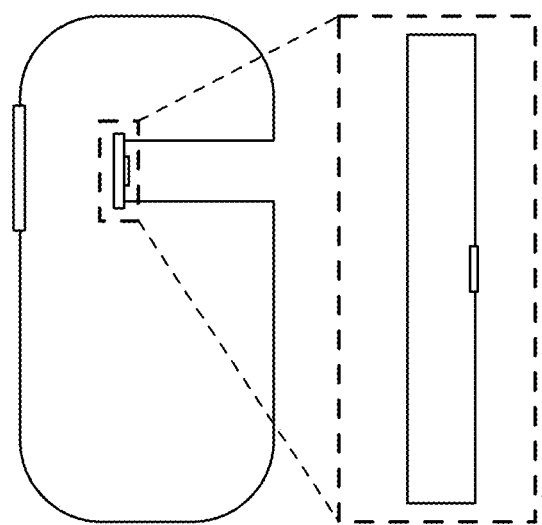
FIG. 11A depicts a computational domain for RF ablation modeling and includes the following domains: (1) thoracic cavity and (2) collapsed esophagus and boundaries: (a) ablation catheter tip and (b) grounding pad.

Computational domain (Geometry). FIG. 11A shows the computational domain marking its subdomains and main boundaries. The esophagus thickness can be adjusted based on prior knowledge, imaging output, or population means. The esophagus height in this example is 45 mm, the ablation catheter tip is 4 mm, and the grounding pad is 76.2 mm.

Governing equations and boundary conditions. The model governing equations were associated with two phenomena: (1) RF electromagnetic energy as a heat source and (2) the resulting heat transfer. The detailed governing equations and boundary conditions were discriminated as described below, following which are shown how the equations involved are coupled.

(1) RF Electromagnetic Energy as Heat Source

Governing equations. Maxwell equations govern the electromagnetism. The AC/DC module from Comsol was used to model electromagnetic phenomena at low frequency. According to RF ablation modeling recommendations found in https://www.comsol.com/blogs/study-radiofrequency-tissue-ablation-using-simulation/, the electrical skin depth of the human body is on the order of one meter, while the heated regions have a typical size on the order of a centimeter, hence, the assumption was made that heating due to induced currents in the tissue is negligible and was not calculated (although this assumption would not be valid if some small pieces of metal exist within the tissue, such as a stent within a nearby blood vessel). Given this assumption, electric currents were considered as the heating source, and the Electric Currents interface from the AC/DC module was used, which solved the equations shown in Equation Set 1 to obtain the electric potential in the computational domain; J is the current density, $Q_{j,V}$ is the current source term, $\sigma$ is the electric conductivity, E is the electric field intensity, D is the electric displacement, $\omega$ is the angular frequency, $J_e$ is the external current density, and V is the electric potential.

Equation Set 1, governing equations for RF energy inside the body:

$$\nabla \cdot J = Q_{j,v}$$

$$J = \sigma E + j\omega D + J_e$$

$$E = -\nabla V$$

Table 2 shows and describes the applied boundary conditions needed to solve the previously described governing equations.

TABLE 2

Boundary conditions for RF ablation directly on the esophagus

| Boundary Condition | Equation | Specifications |
|---|---|---|
| (a) Power terminal at Ablation Cathter Tip | Terminal power (P) and characteristic impedance (Z) are specified | P = 10 W<br>Z = 45Ω, 73Ω<br>Taken from experimental ablation conditions |
| (b) Reference Impedance at Grounding Pad | $n \cdot J = \dfrac{1}{d_s}(\sigma + j\omega\varepsilon_0\varepsilon_r)(V - V_{ref})$<br>$d_s$ = surface thickness<br>$\sigma$ = electrical conductivity<br>$\omega$ = angular frequency<br>$\varepsilon_0$ = vacuum permittivity<br>$\varepsilon_r$ = relative permitttivity<br>$V_{ref}$ = reference voltage | Skin values for $\sigma$ and $\varepsilon_r$<br>$V_{ref}$ = 0 [V]<br>$d_s$ = 5 [mm] (default value) |
| (c) Electric Insulation at Skin | $n \cdot J = 0$ | |

(2) Heat Transfer.

Governing equations. An energy balance governs the heat transfer, and the Heat Transfer module from Comsol was used to model the heat transfer phenomena. According to the RF ablation modeling instructions found in https://www.comsol.com/blogs/study-radiofrequency-tissue-ablation-using-simulation/, the governing equations for heat transfer in tissues are given by the Pennes Bioheat equation (Equation Set 2). This equation was solved through the Bioheat Transfer interface from the Heat Transfer module. The equation was solved to obtain the temperatures in all of the computational domains. In the Pennes Bioheat equation, T is the temperature, $d_z$ is the thickness (out of plane), $\rho$ is the is the density, $C_p$ is the heat capacity, u is the fluid velocity, k is the thermal conductivity, Q is the heat source term, $q_0$ is the radiation heat term and $Q_{bio}$ is the metabolic heat production rate.

Equation Set 2, governing equations for bioheat transfer inside the body:

$$d_Z \rho C_P \frac{\partial T}{\partial t} + d_Z \rho C_p u \cdot \nabla T + \nabla \cdot q = d_Z Q + q_0 + d_Z Q_{bio}$$

$$q = -d_z k \nabla T$$

Table 3 shows and describe the applied boundary conditions needed to solve the previously described governing equations.

TABLE 3

Boundary conditions for bioheat transfer due RF ablation

| Boundary Condition | Equation | Specifications |
|---|---|---|
| (a) Convective heat flux at skin | $-n \cdot q = d_z q_0$<br>$q_0 = h(T_{ext} - T)$<br>$d_z$ = thickness (out of plane)<br>h = heat transfer coefficient<br>$T_{ext}$ = room temperature | Esophagus<br>$d_z$ = 6 [mm]<br>Thoracic Cavity<br>$d_z$ = 6[cm]<br>(calibrted to fit experiments)<br>$T_{ext}$ = 20° C. |
| (b) Thermal Isolation at Grounding Pad | $-n \cdot q = 0$ | |

Multiphysics coupling. To couple RF energy and bioheat transfer, the interface Electromagnetic Heat Source from the Multiphysics module of Comsol was used, as it contains the relation shown in Equation Set 3, which establishes the heat source as that produced by the electromagnetic energy source.

Equation Set 3, electromagnetic energy and bioheat transfer coupling equations:

$$\rho C_p u \cdot \nabla T = \nabla \cdot (k \nabla T) + Q_e$$

$$Q_e = J \cdot E$$

TABLE 4

Electric material properties for RF ablation directly to the esophagus.

| Domain or boundary | Material Properties | Observations |
|---|---|---|
| 1 Thoracic Cavity | $\sigma = 0.50$[S/m] $\varepsilon_r = 65$ | Average human tissue values |
| 2 Esophagus | $\sigma = 0.50$[S/m] $\varepsilon_r = 65$ | Average human tissue values |
| A Skin in contact with Grounding Pad | $\sigma = 0.50$[S/m] $\varepsilon_r = 65$ | Average human tissue values |

TABLE 5

Thermal properties for heat transfer during RF ablation.

| Domain or boundary | Material Properties | Observations |
|---|---|---|
| 1 Thoracic Cavity | $C_p = 3421$ [J/(kg*K)] $\rho = 1090$ [kg/m^3] $k = 2.00$ [W/(m*K)] | Muscle tissue values available in Comsol materials library, k calibrated to fit the experiments |
| 2 Esophagus | $C_p = 3421$ [J/(kg*K)] $\rho = 1090$ [kg/m^3] $k = 0.50$ and 1.91 [W/(m*K)] | Muscle tissue values available in Comsol materials library for $\rho$ and $C_p$. k are limit values found in literature |

TABLE 5-continued

Thermal properties for heat transfer during RF ablation.

| Domain or boundary | Material Properties | Observations |
|---|---|---|
| A Skin-air interface | h = 7.50 [W/m$_2$ · K] | Between 5-10 [W/m$_2$ · K] |

Figure 12:
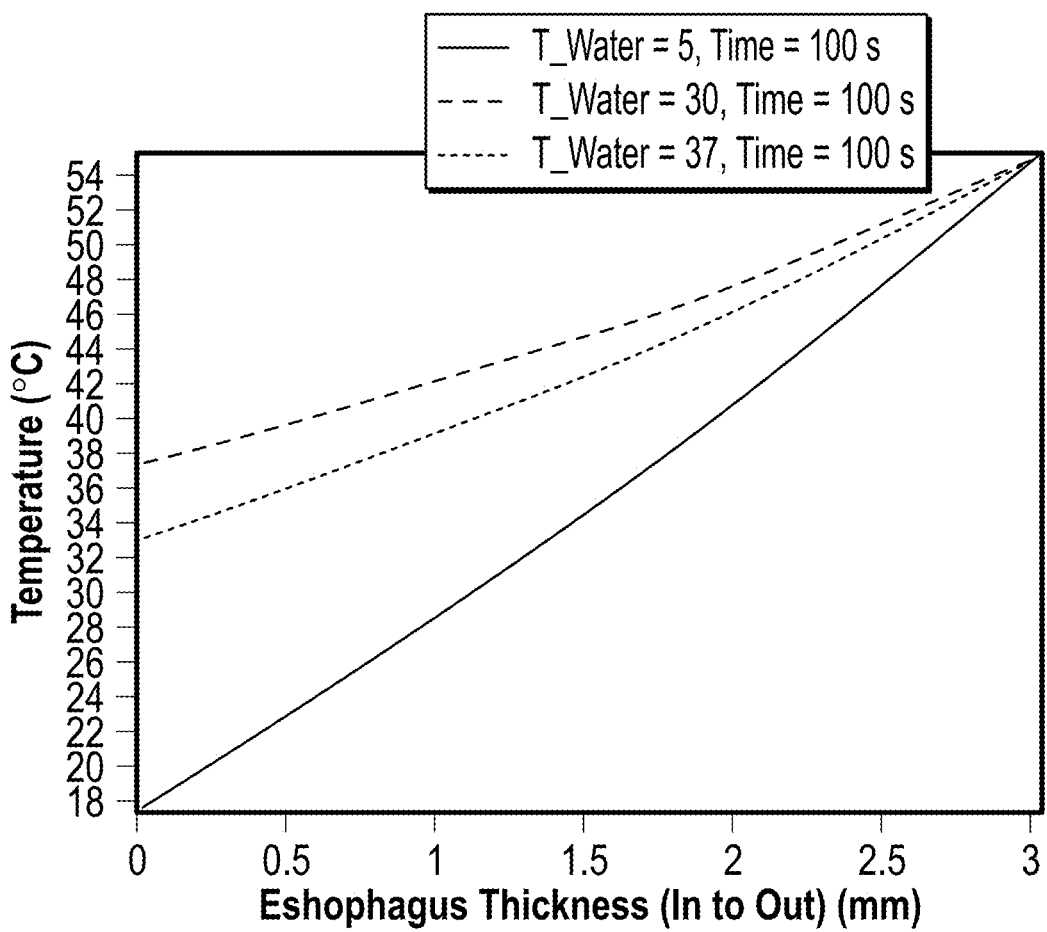
FIG. 12 is a line graph depicting computed esophageal temperature during an ablation procedure with water flow at different temperatures and 100 second ablation time.

Domain decomposition was used to solve a boundary value problem by splitting it into smaller boundary value problems on subdomains and iterating to coordinate the solution between adjacent subdomains. After solving for the temperature given the known tissue parameters and applied RF energy, the profile of temperature through the tissue at the end of a 100 second ablation procedure, using differing circulating coolant temperatures through the esophageal heat transfer device, is shown graphically in FIG. 12.

Full Model Incorporating Atrial Ablation with Esophageal Protection

This section includes the problem formulation, model implementation and comparison between both simulated and experimental results for the full model incorporating atrial ablation with esophageal protection.

Figure 11B:
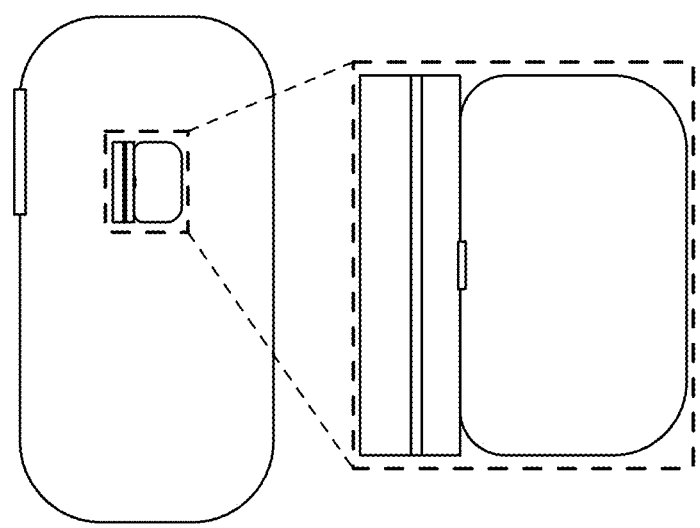
FIG. 11B depicts a computation domain for RF ablation modeling in the 2D sagittal plane and includes the following domains: (1) thoracic cavity, (2) contracted esophagus, (3) pericardium, (4) myocardium, and (5) left atrium and boundaries: (a) ground pad and (b) catheter tip.

Computational domain (Geometry). FIG. 11B shows the 2D geometry. The whole domain was separated in five regions: (1) thoracic cavity, (2) contracted esophagus, (3) pericardium, (4) myocardium, and (5) left atrium.

Governing equations and boundary conditions. RF ablation modeling requires solving equations associated to three physics phenomena: (1) blood dynamics, (2) RF energy as heat source, and (3) heat transfer. The detailed governing equations and boundary conditions are discriminated by physics as follows.

(1) Blood Dynamics in the Left Atrium (Mass and Momentum Transfer)

Governing equations. The mass and momentum balances govern the fluid dynamics. The CFD module of Comsol was used to model the dynamics of fluids. Depending on flow regime (given by Reynolds number), one or the other CFD interface must be used. As some turbulence can occur in the left atrium in the cardiac cycle, the CFD module interface selected from Comsol for this modeling was Turbulent Flow, k–ε, which solves the equations shown in Equation Set 4 in order to obtain the blood velocity and pressure profile. The blood flow was considered incompressible to reduce computational time. In the equations shown in Equation Set 4, $\rho$ is the fluid density, u is the velocity field, p is the pressure, $\mu$ is the fluid dynamic viscosity, and F represents bulk forces. The turbulent k–ε model is based on the transported variables k (turbulent kinetic energy) and ε (the rate of dissipation of turbulence energy). The k-E model also needs already calibrated constants: $\sigma_k$, $\sigma_\varepsilon$, $P_k$, $c\varepsilon 1$, $c_{\varepsilon 2}$, $c_\mu$.

Equation Set 4, boundary conditions for turbulent flow:

$$\rho(u \cdot \nabla)u = \nabla \cdot [-p1 + (\mu + \mu_T)(\nabla u + (\nabla u)^T)] + F \qquad \varepsilon = ep$$

$$\rho \nabla \cdot (u) = 0 \qquad \mu_r = \rho C_\mu \frac{k^2}{\varepsilon}$$

$$\rho(u \cdot \nabla)k = \nabla \cdot \left[\left(\mu + \frac{\mu_T}{\sigma_k}\right)\nabla k\right] + P_k \cdot \rho\varepsilon \qquad P_k = \mu_T[\nabla u : (\nabla u + (\nabla u)^T)]$$

$$\rho(u \cdot \nabla)u\varepsilon = \nabla \cdot \left[\left(\mu + \frac{\mu_T}{\sigma_\varepsilon}\right)\nabla \varepsilon\right] + C_{\varepsilon 1} \frac{\varepsilon}{k} P_k - C_{\varepsilon 2} \rho \frac{\varepsilon^2}{k},$$

Results

The model results compared favorably to the above experimental conditions. Temperature profiles determined by the model corresponded to findings on histopathology, in which temperature rises sufficient to induce moderate-to-severe muscularis mucosa damage were eliminated with esophageal cooling using 5° C. water.

Thus, esophageal protection can be modeled accurately, allowing for additional investigation and refinement of protective strategies during ablation of the left atrium for the treatment of atrial fibrillation.

Figure 13:
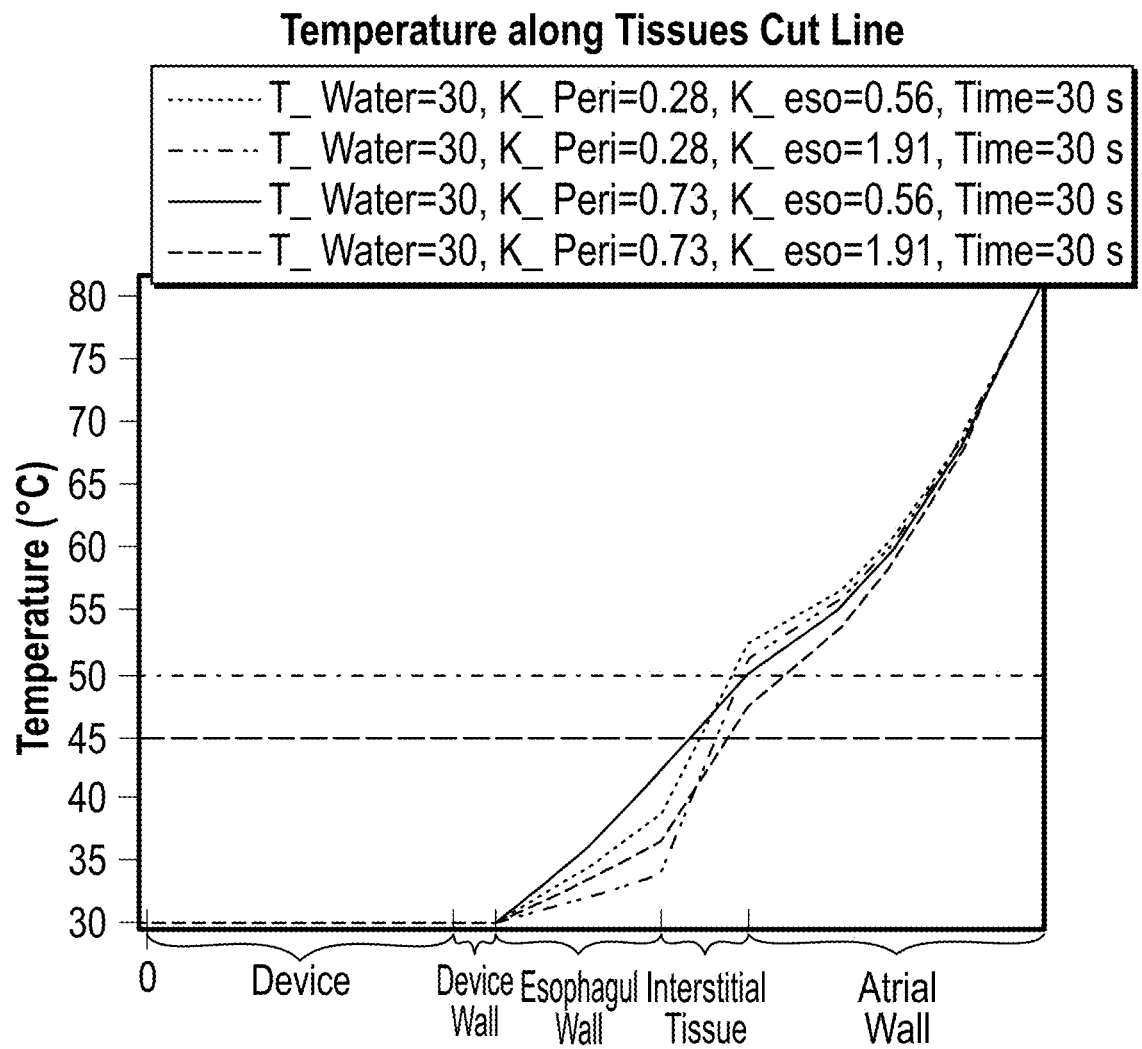
FIG. 13 is a line graph depicting computed temperatures across tissues (esophageal wall, interstitial tissue, and atrial wall) during an ablation procedure with water flow at 30° C. and 30 second ablation time.

In FIG. 13, the x-axis corresponds to distance between the esophageal heat transfer device and the ablation site (from left to right). In particular, from "0" to the first tick mark represents the device, from the first tick mark to the second tick mark represents the device wall, from the second tick mark to the third tick mark represents the esophageal wall (e.g., having temperatures below 45° C.), from the third tick mark to the fourth tick mark represents the interstitial tissue, and from the fourth tick mark to the fifth tick mark represents the atrial wall (e.g., having temperatures above 50° C.).

Example 3. Esophageal Protection During RF Ablation

The results presented below demonstrate that coolant temperature can be adjusted for specific RF ablation parameters to assure the desired myocardial tissue ablation is obtained while protecting esophageal tissue from thermal injury.

Example 3A. Model Using 45 Second Ablation Time

This example describes a simulation of the process of RF ablation of left atrium in two situations: (1) a collapsed esophagus in contact with left atrium and (2) where esophageal tissue is protected from burning by inserting a cooling device with different temperatures of water flow. The governing equations and boundary conditions were generally as described in Example 2 above.

The thermal conductivity was specified for myocardium, esophagus, and pericardium, evaluated at 10 W to 50 W applied power, with the cooling device operating with circulating water ranging from as cold as 5° C. to as warm as 37° C.

Figure 14:
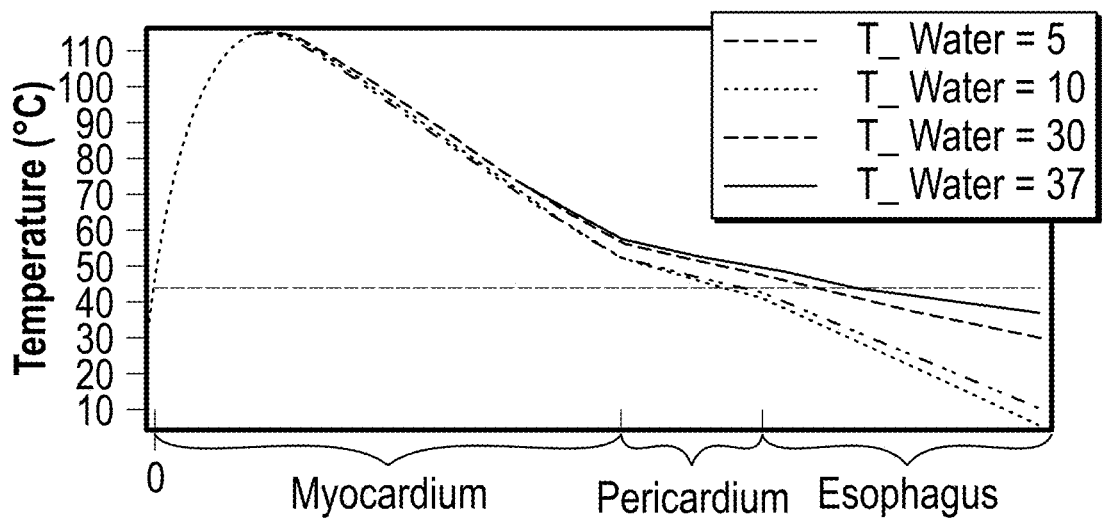
FIG. 14 is a line graph depicting computed temperatures across tissues (myocardium, pericardium, esophagus) during an ablation procedure with water flow at different temperatures and 45 second ablation time.
Figure 15:
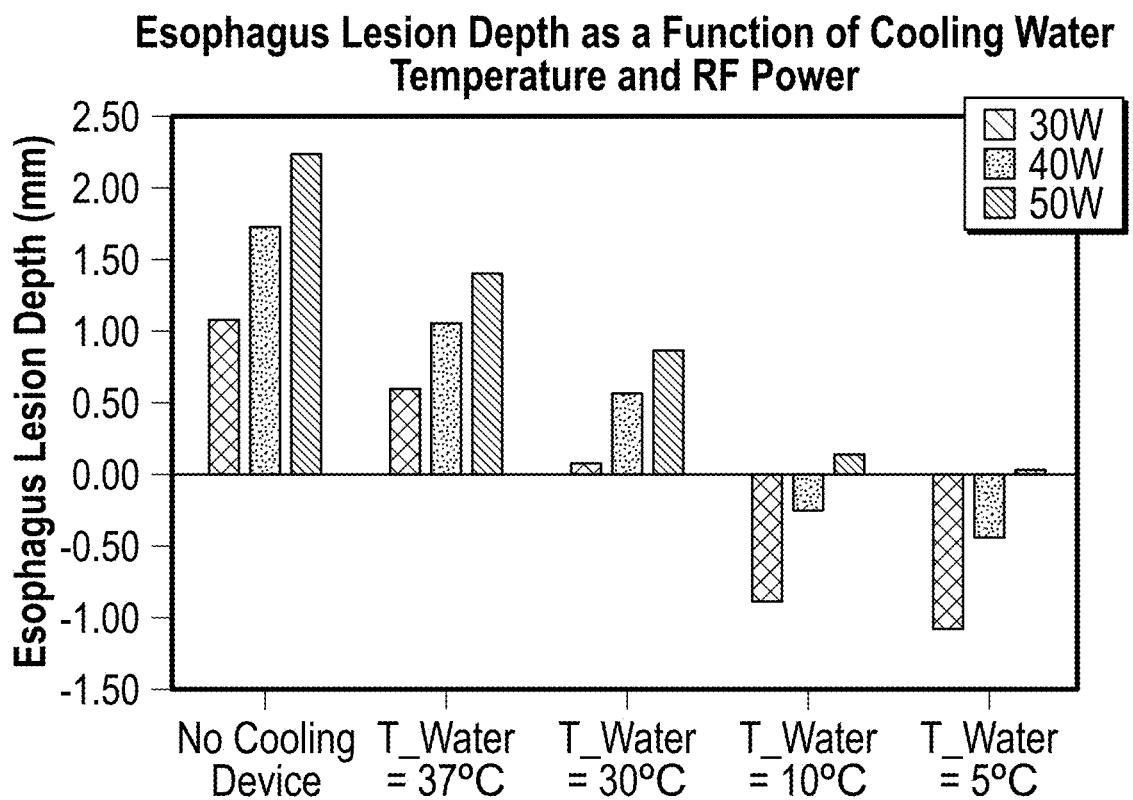
FIG. 15 is a bar graph depicting lesion depth for both non-protected and protected esophageal tissue at different RF power values with water flow at different temperatures and 45 second ablation time.

FIG. 14 shows the temperature across ablated tissues at 40 W RF power applied and for all considered cooling water temperatures. FIG. 15 shows a bar graph of lesion depth for both non-protected and protected esophagus at different RF power values.

Figure 16:
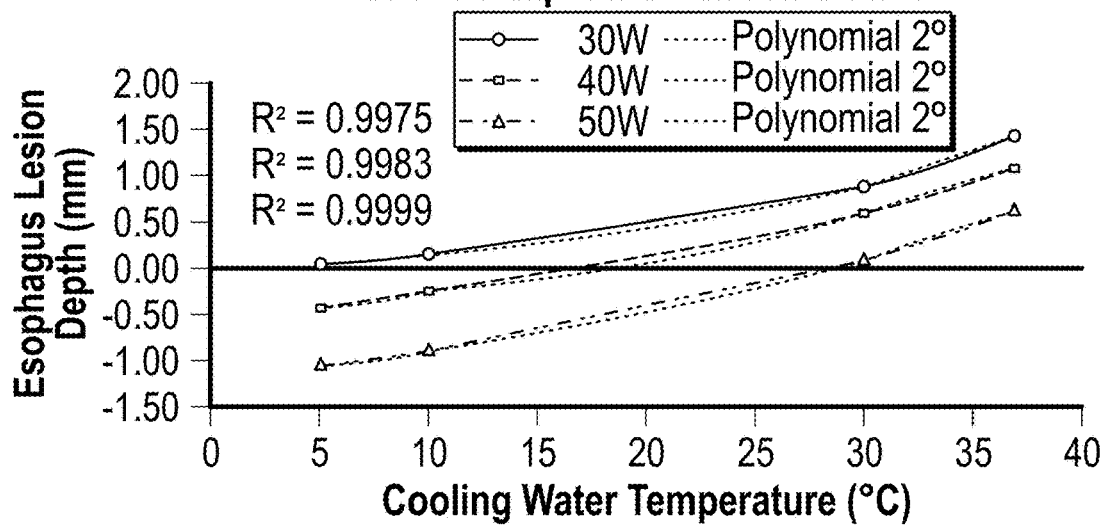
FIG. 16 is a line graph depicting esophageal lesion depth as a function of cooling water temperature at different RF power values after 45 second ablation. Adjusting lines correspond to second order polynomial interpolations.
Figure 17:
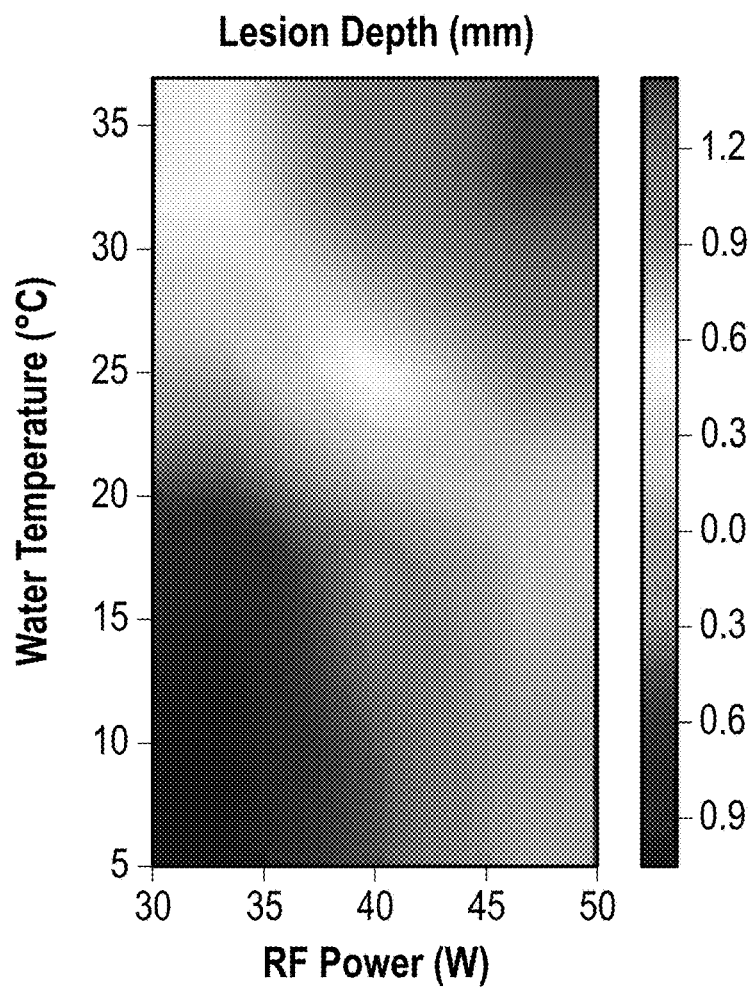
FIG. 17 is a lesion depth contour plot showing the lesion depth as a function of water temperature and RF power.

The esophageal lesion depth as a function of cooling water temperature for 30 W, 40 W and 50 W applied RF power is shown in FIG. 16. Interpolation lines are also shown corresponding to second order polynomials and $R^2$ values are shown. Finally, a contour plot showing the lesion depth as a function of both cooling water temperature an applied RF power is shown in FIG. 17.

Using a lethal isotherm of above 44° C., the cooling device protected esophageal tissue for all cases where damage was predicted. (FIG. 16 and FIG. 17).

Example 3B. Model Using 60 Second Ablation Time

This example describes a simulation of the process of RF ablation of left atrium in two situations: (1) a collapsed esophagus in contact with left atrium and (2) where esophageal tissue is protected from burning by inserting a cooling device with different temperatures of water flow. The governing equations and boundary conditions were generally as described in Example 2 above.

The simulations were designed to study the influence of coolant temperature on up to 60 s of RF ablation using 40 W RF power and 0 mm insertion depth. Although the lethal isotherm for radiofrequency catheter ablation of myocardium has often been considered to be 50° C., and some have suggested an even higher value near 61° C. for radiofrequency energy deliveries less than 240 seconds in duration, a more conservative 44° C. was used in order to avoid overestimating the protective capacity of this approach.

Figure 18A:
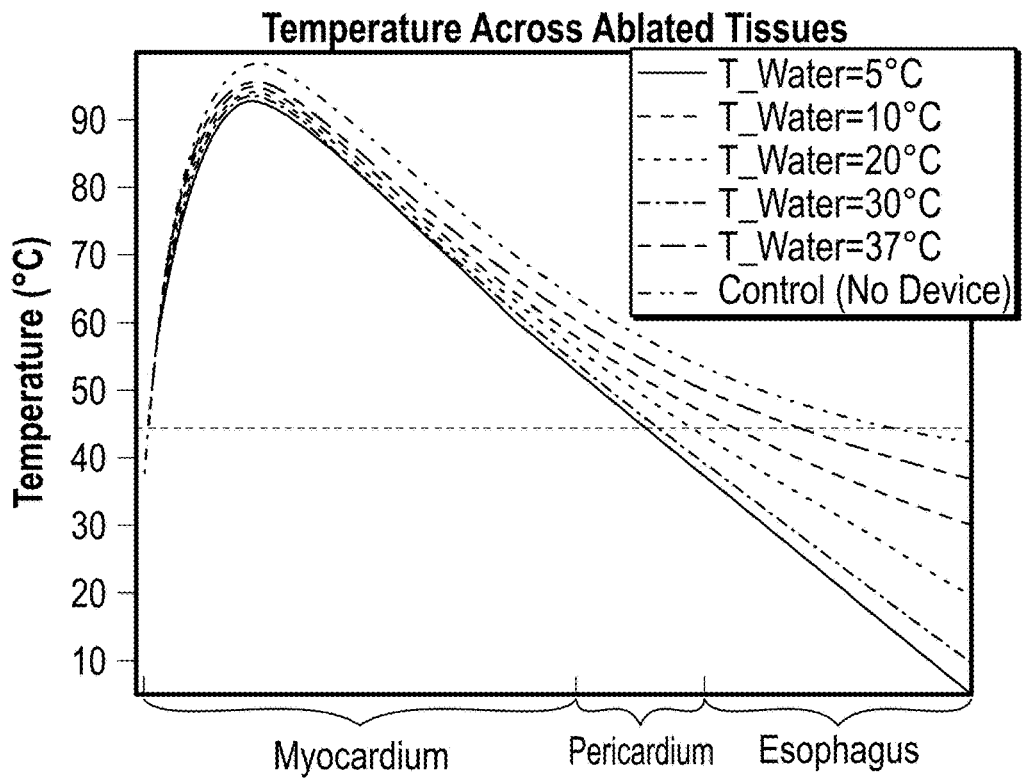
FIG. 18A is a line graph depicting computed temperatures across tissues (myocardium, pericardium, esophagus) during an ablation procedure using 40 W RF power applied and 0 mm insertion depth with water flow at different temperatures.
Figure 18B:
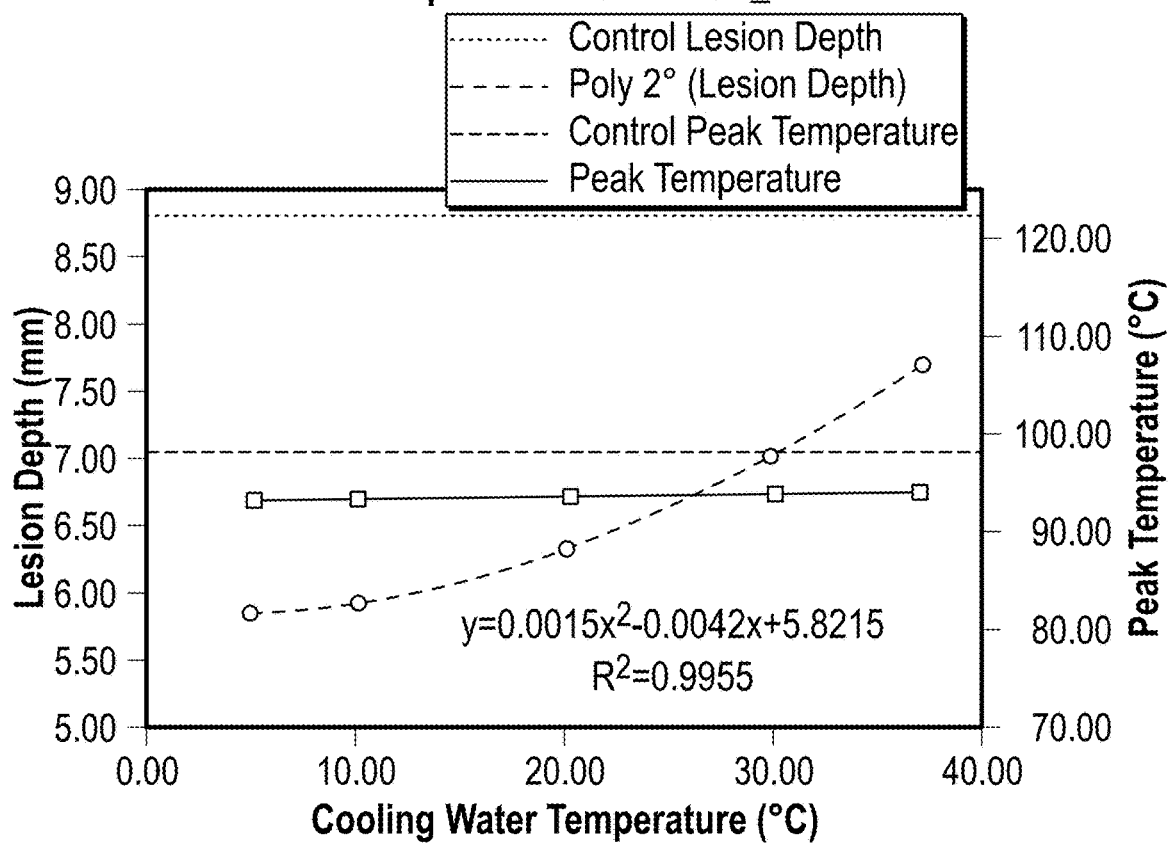
FIG. 18B is a line graph depicting peak temperature and lesion depth as a function of water temperature referred to control values (collapsed esophagus study). A second order polynomial (parabolic) line was adjusted to five data points of cooling water temperature (T_Water), and the resulting equation and $R^2$ value is presented. No regression was applied for peak temperature data as the variations within T_water values are small.

FIGS. 18A and 18B shows esophageal protection from thermal injury at different cooling water temperatures and demonstrate how lesion formation and depth changes with cooling water temperature. FIG. 18A shows temperature profile while varying water temperature. FIG. 18B shows peak temperature and lesion depth as a function of water temperature (Ablation time=60 s, RF Power=40 W, Insertion Depth=0 mm).

Figure 19A:
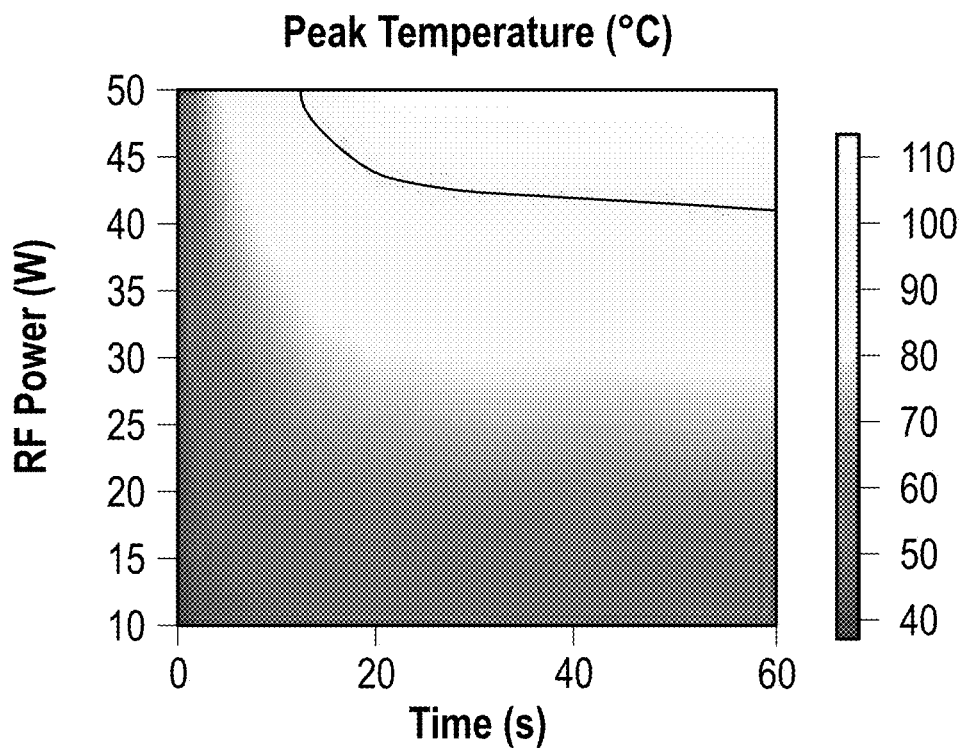
FIG. 19A is a contour plot showing peak temperature as a function of RF power and time (Insertion depth=0 mm).
Figure 19B:
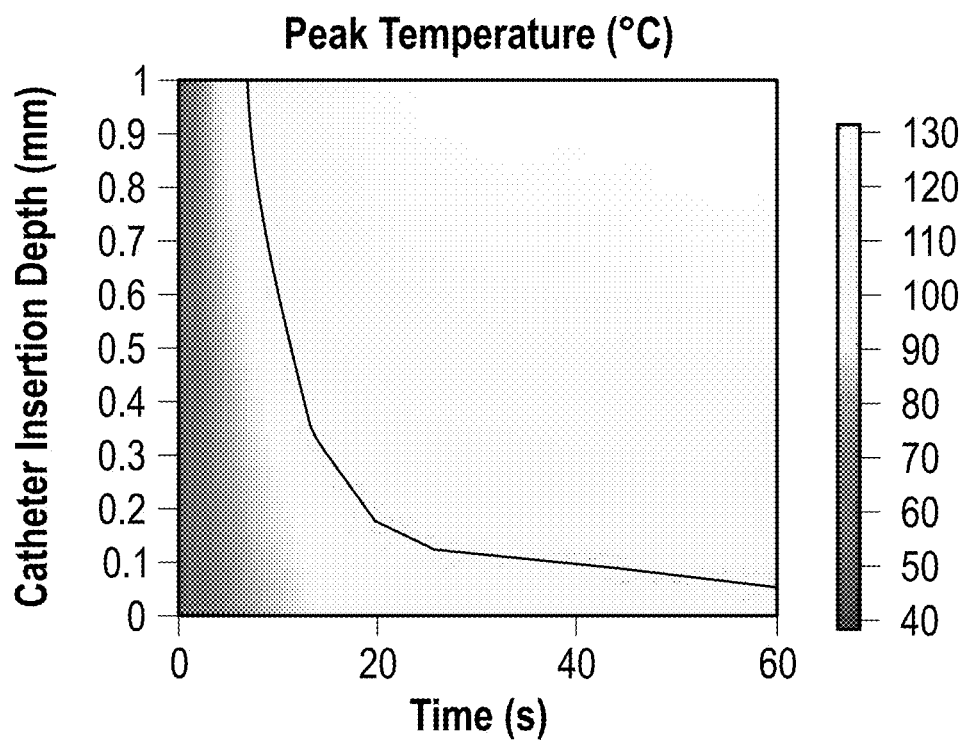
FIG. 19B is a contour plot showing peak temperature as a function of insertion depth and time (RF Power=40 W).
Figure 19C:
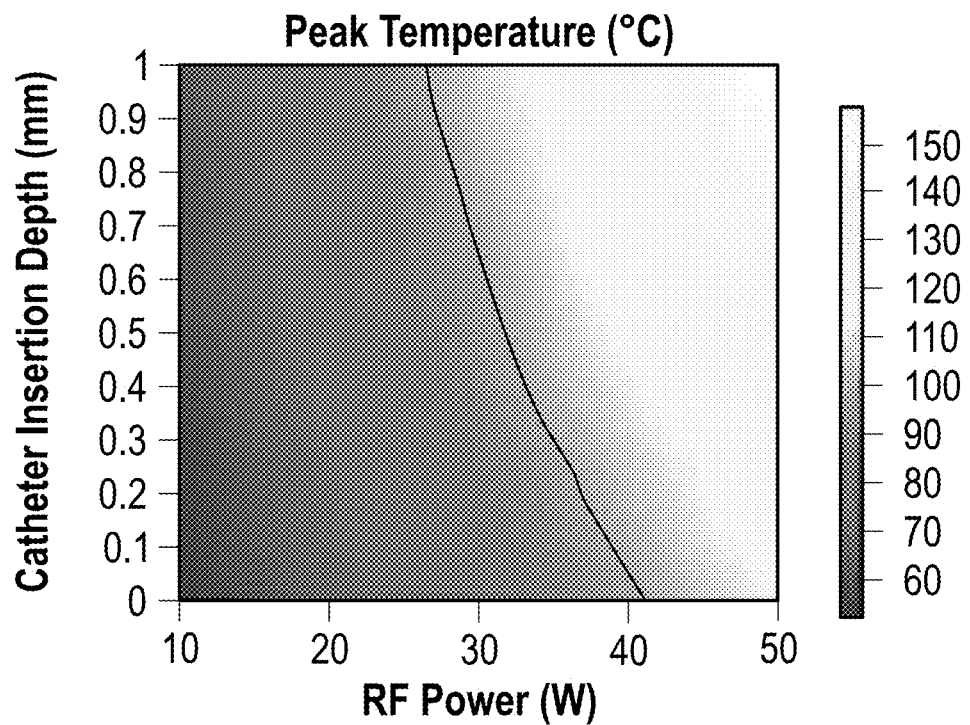
FIG. 19C is a contour plot showing peak temperature as a function of insertion depth and RF power (ablation time=60 s). Lines mark 100° C. limit temperature.
Figure 20A:
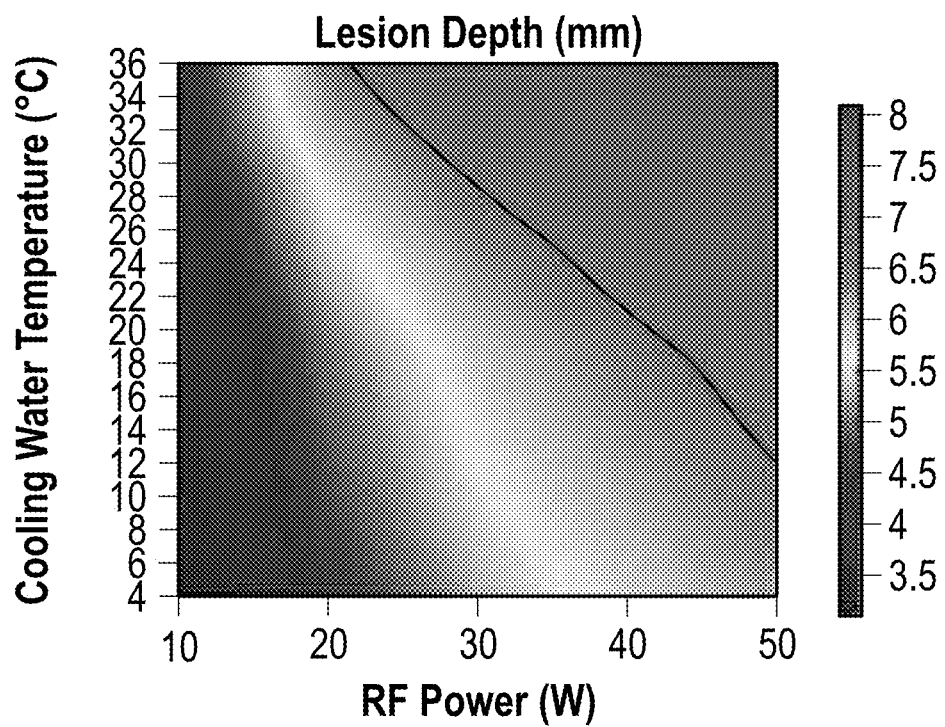
FIG. 20A is a lesion depth contour plot showing the lesion depth as a function of cooling water temperature and RF power (Insertion depth=0 mm, ablation time=60 s).
Figure 20B:
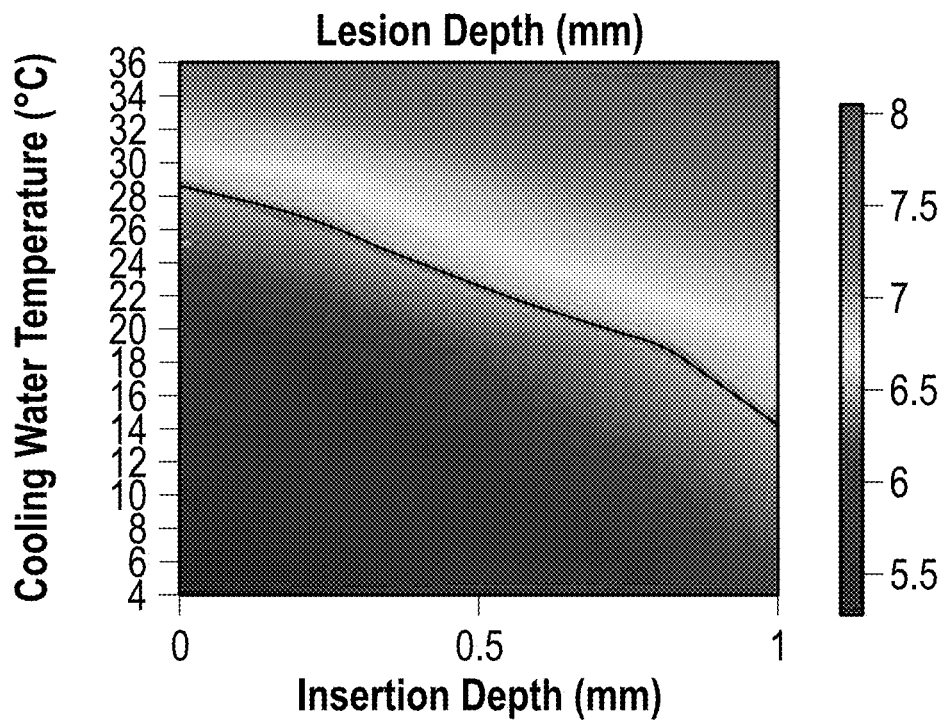
FIG. 20B is a lesion depth contour plot showing the lesion depth as a function of cooling water temperature and insertion depth (RF Power=40 W, ablation time=60 s).
Figure 20C:
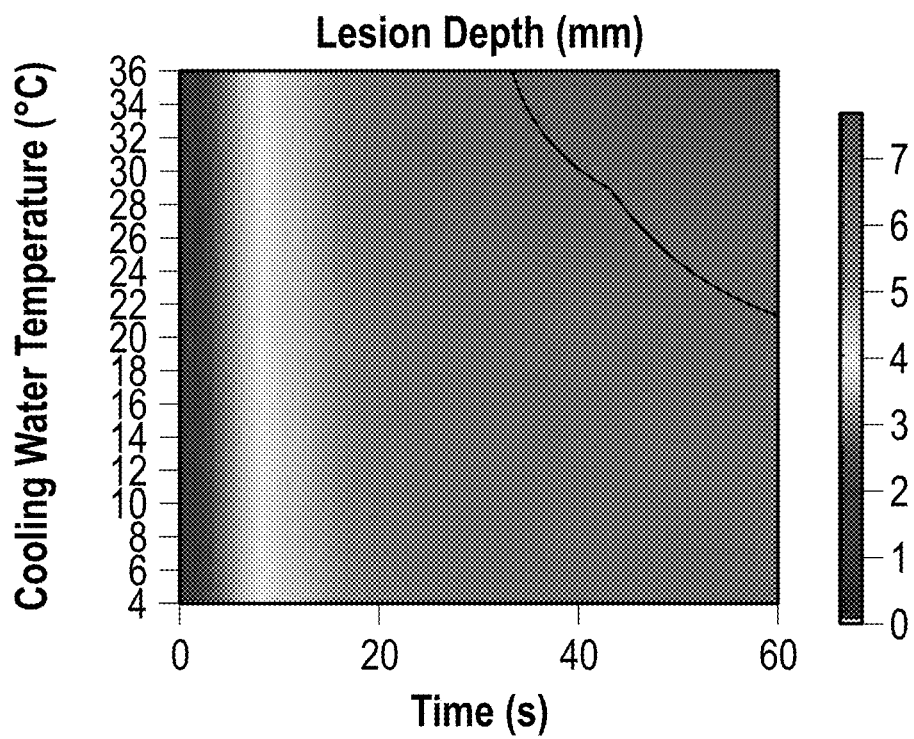
FIG. 20C is a lesion depth contour plot showing the lesion depth as a function of cooling water temperature and time (RF Power=40 W, insertion depth=0 mm). Lines mark 6.5 mm optimum lesion depth for the tissue thicknesses considered.

FIGS. 19A, 19B, and 19C are contour plots showing the peak temperature as a function of both RF power and ablation time, insertion depth and time and RF power and insertion depth.

Example 4. Esophageal Protection During Cryoablation

The results presented below demonstrate that esophageal warming provided protection from dangerous nadir temperatures at all typical treatment times. In particular, the results show that even in the most unfavorable conditions, with minimal pericardial fat insulation, esophageal warming can prevent luminal temperatures from decreasing to dangerous levels.

Example 4A. Model Using −50° C. Cryoablation Temperature

This example describes a simulation of the process of cryoablation of left atrium. The governing equations and boundary conditions were generally as described in Example 2 above.

Figure 21:
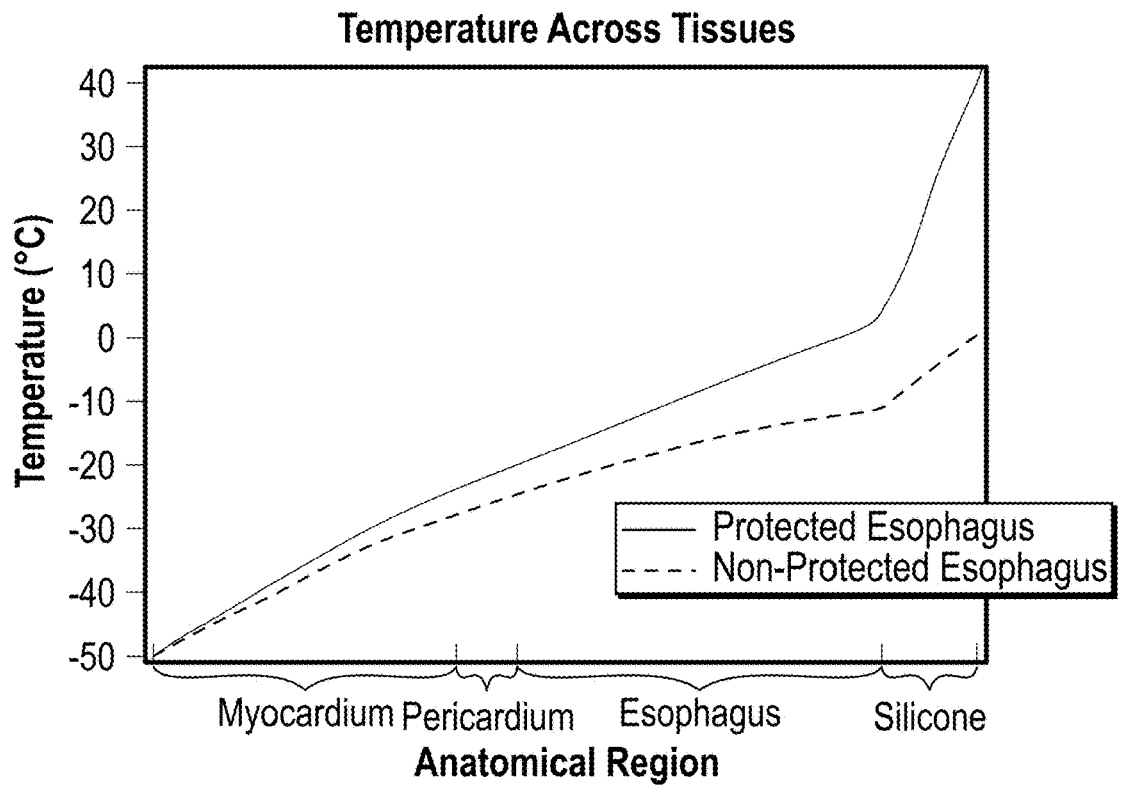
FIG. 21 is a line graph depicting computed temperatures across tissues (myocardium, pericardium, esophagus) during a cryoablation procedure with and without esophageal protection at −50° C. cryoballoon temperature.

The cryoablation balloon (modelled after the Medtronic Arctic Front Advance Cardiac CryoAblation Catheter system) was set to −50° C., and the model included the myocardial wall, fatty tissue, pericardium, the esophageal wall, and finally the device, with a water flow of 60 L/min at 42° C. The temperature across tissues after 3 min cryoablation is shown in FIG. 21, suggesting considerable esophageal protection with 42° C. water flow through the esophageal heat transfer device.

Example 4B. Model Using −70° C. Cryoablation Temperature

This example describes a simulation of the process of cryoablation of left atrium. The governing equations and boundary conditions were generally as described in Example 2 above.

The model utilized a configuration where esophageal tissue was in contact with left atrium and an esophageal warming device was placed within the esophagus. Cryoballoon temperatures were evaluated as low as −70° C., and the model included the myocardial wall, fatty tissue, pericardium, the esophageal wall, and finally the device, with water flow temperature of 42° C.

Figure 22A:
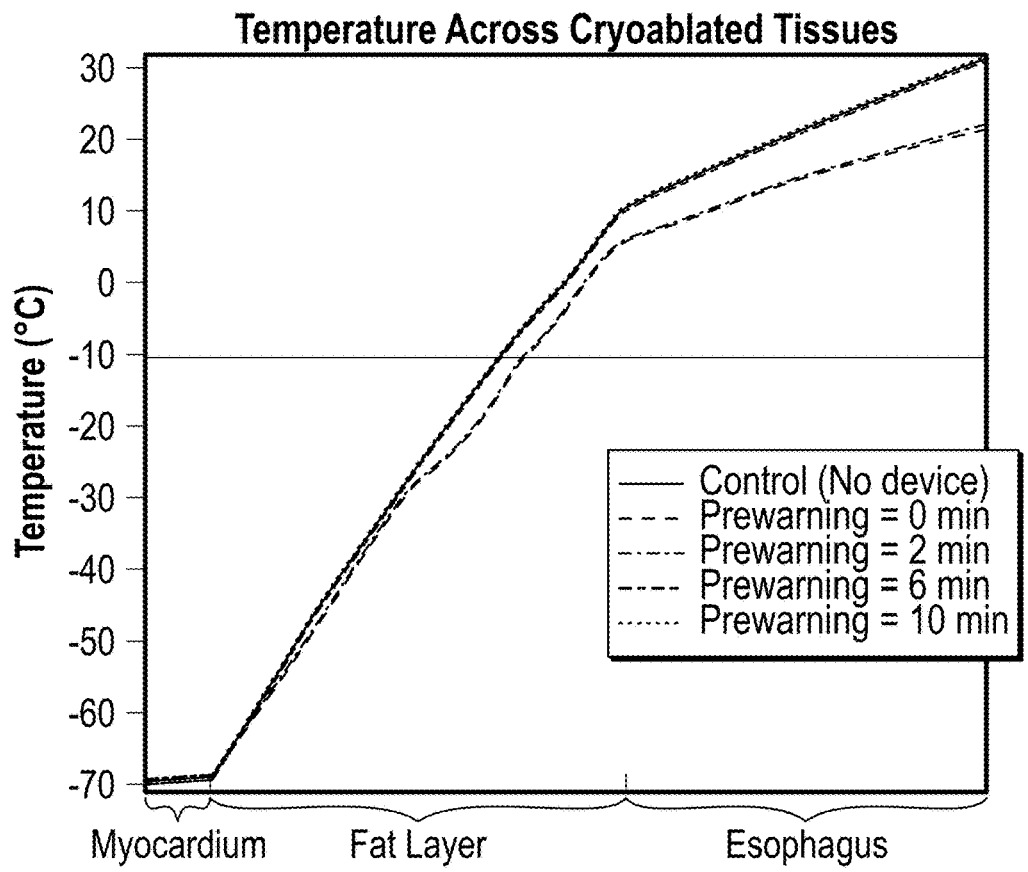
FIG. 22A is a line graph depicting computed temperatures across tissues (myocardium, fat layer, esophagus) during a cryoablation procedure for an unprotected (control) and a protected esophagus at different prewarming times using a myocardial thickness of 0.5 mm.
Figure 22B:
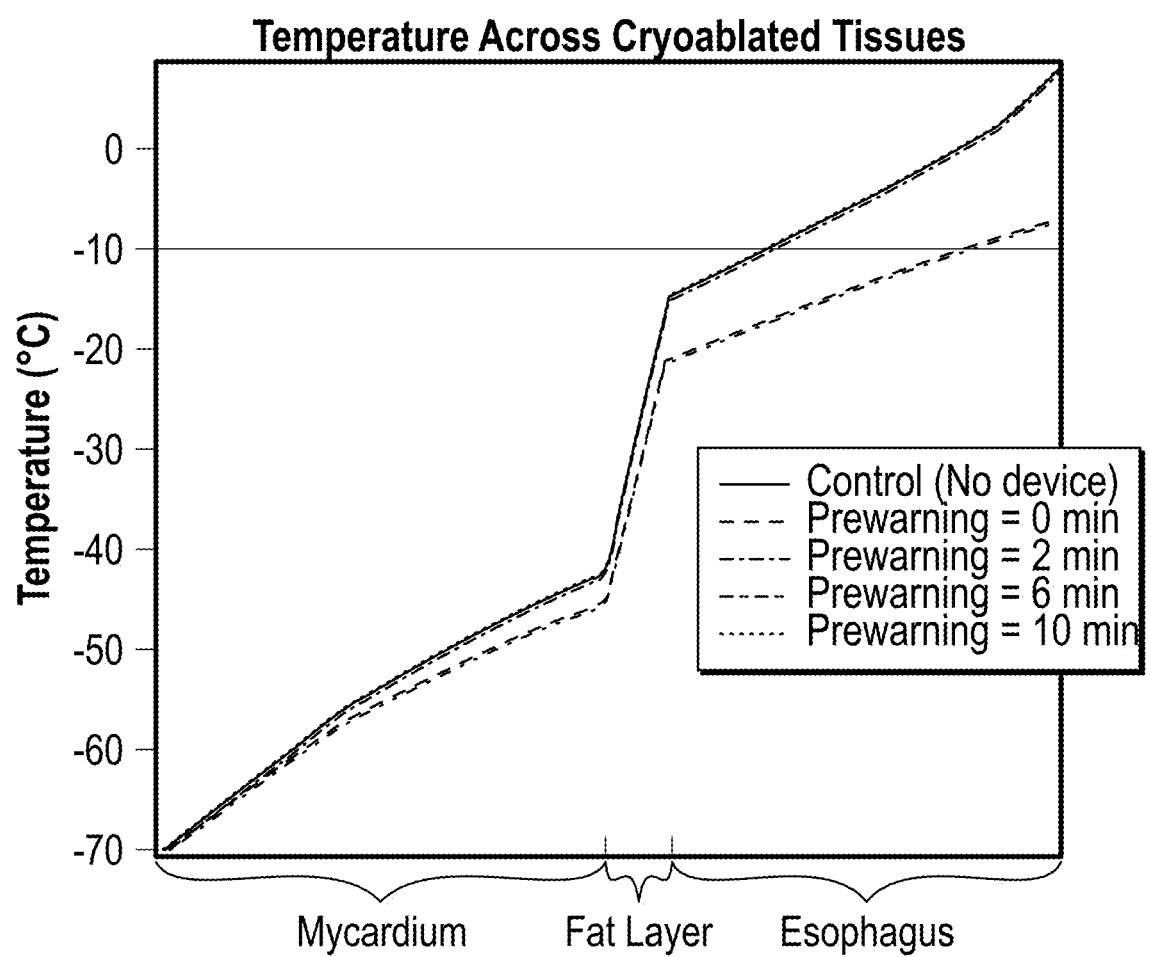
FIG. 22B is a line graph depicting computed temperatures across tissues (myocardium, fat layer, esophagus) during a cryoablation procedure for an unprotected (control) and a protected esophagus at different prewarming times using a myocardial thickness of 3.5 mm.

FIG. 22A and FIG. 22B compare the temperature across cryoablated tissues for an unprotected (control) and a protected esophagus at different prewarming times and at −70° C. cryoballoon temperature and 3 minutes of cryoablation. Myocardial thickness is 0.5 mm in FIG. 22A and 3.5 mm in FIG. 22B. Results for the control condition (no device), and various durations of prewarming are shown.

Figure 23A:
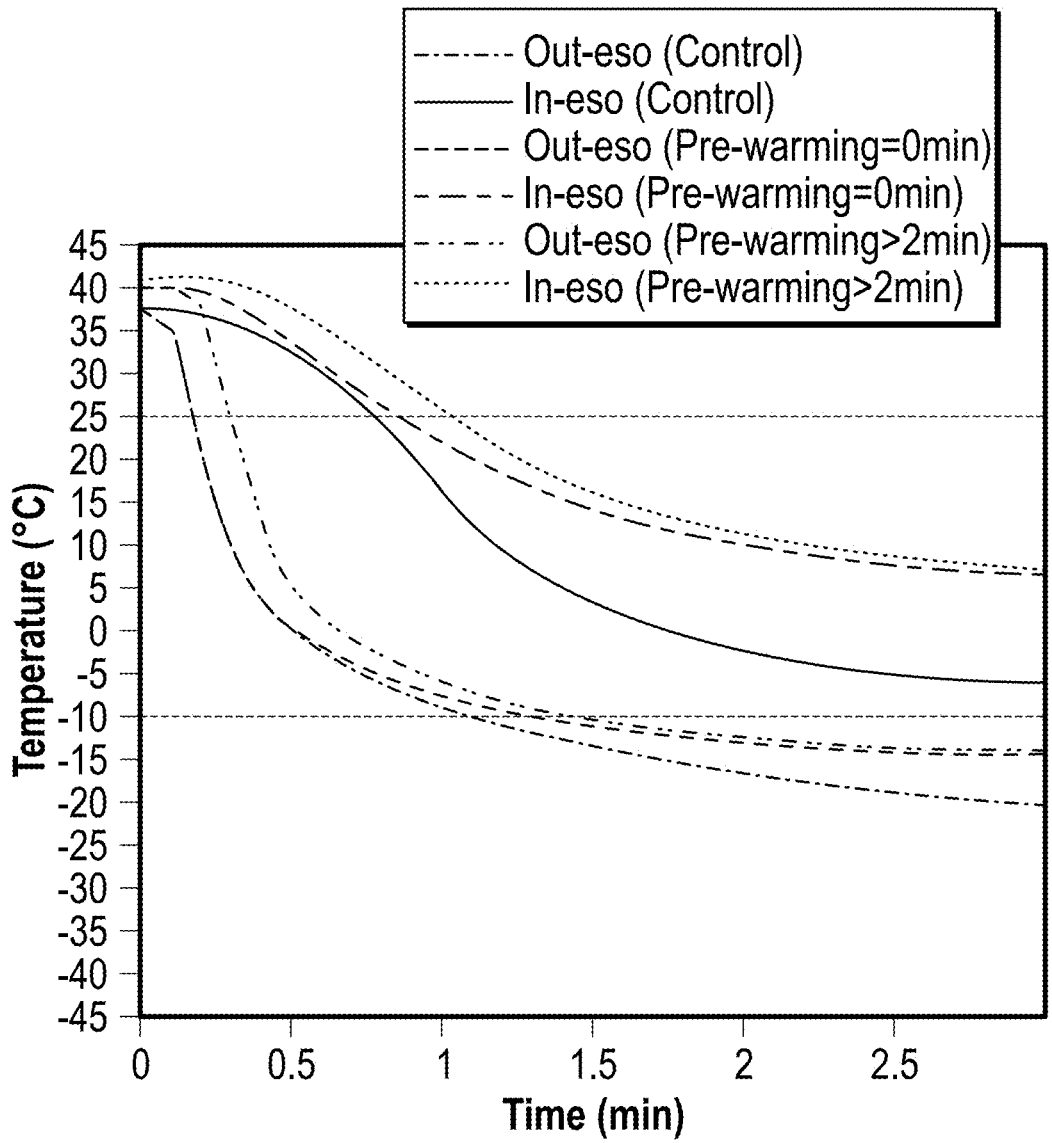
FIG. 23A is a line graph depicting computed temperatures over time for the inner and outer esophagus (In-eso, Out-eso) during a cryoablation procedure for an unprotected (control) and a protected esophagus at different prewarming times using a myocardial thickness of 3.5 mm.
Figure 23B:
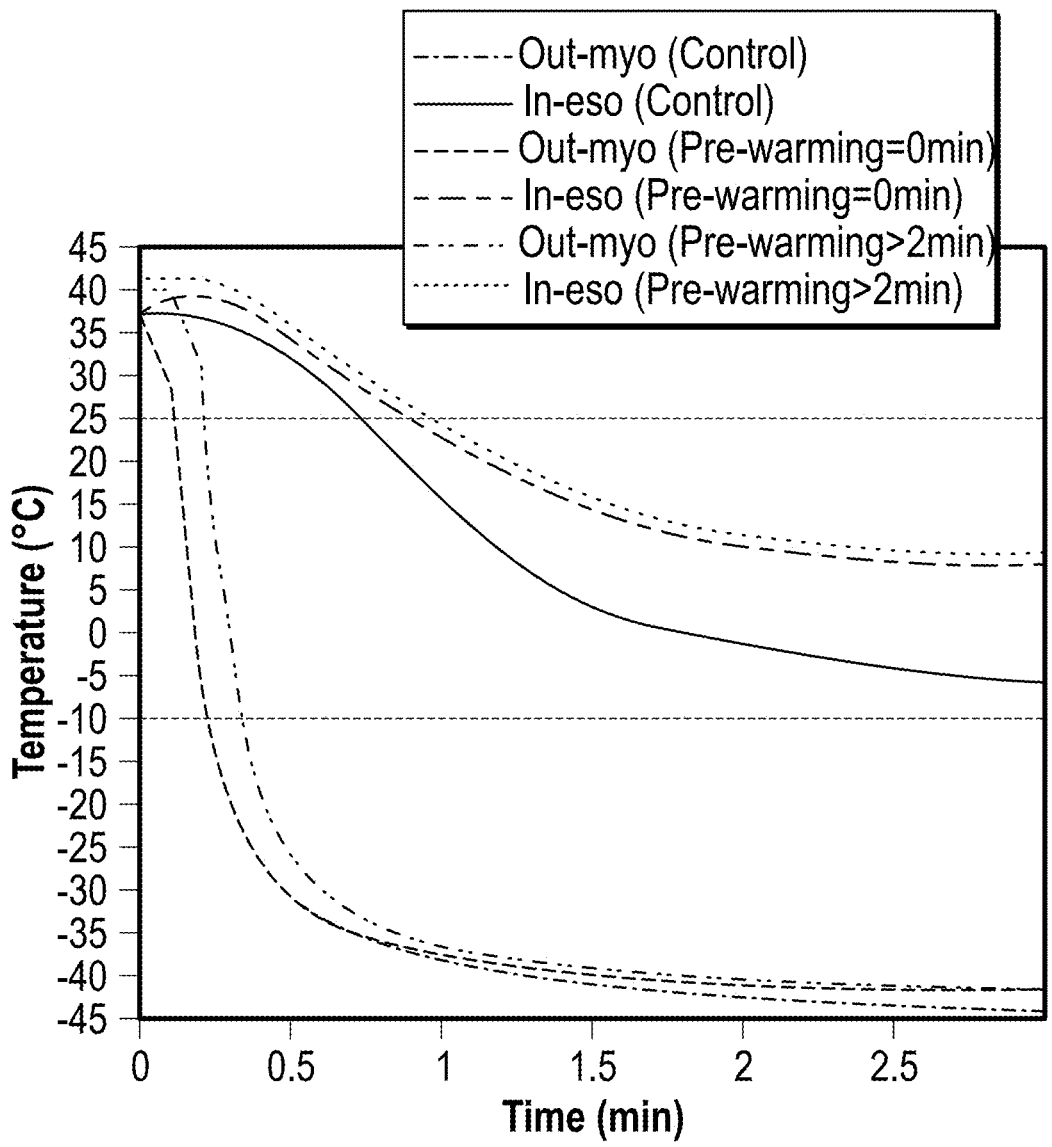
FIG. 23B is a line graph depicting computed temperatures over time for the inner esophagus and outer myocardium (In-eso, Out-myo) during a cryoablation procedure for an unprotected (control) and a protected esophagus at different prewarming times using a myocardial thickness of 3.5 mm.

FIG. 23A and FIG. 23B show temperature as a function of cryoablation time at relevant points from outer myocardium to inner esophageal wall. Results for the control condition (no device), and various durations of prewarming are shown. Cryoablation temperature=−70° C. Myocardial thickness is 3.5 mm. FIG. 23A shows the inner and outer esophagus (In-eso, Out-eso), and FIG. 23B shows the inner esophagus and outer myocardium (In-eso, Out-myo).

Example 5

High-power, short-duration (HPSD) ablation is a relatively new strategy for performing RF ablation. It has been proposed that HPSD may reduce or eliminate the detrimental impact on esophageal tissue as compared to using standard (low-power, long-duration) ablation (typically 20-30 Watts for 20-30 seconds or so). However, retrospective evaluation of patients who had received HPSD showed similar esophageal thermal injury patterns as compared to low-power, long-duration ablation. The following example demonstrates that an esophageal heat transfer device can reduce and even eliminate esophageal thermal injury associated with HPSD ablation.

Part 1. A finite element model of HPSD ablation with RF energy (50 W for 5-10 seconds, and 90 W for 4 seconds) in the left atrium. Tissue parameters as defined in COMSOL Multiphysics were utilized; however, because a wide range of myocardial thermal conductivities are reported in the literature, the entire range (from 0.5 W/m*K to 1.5 W/m*K) was examined. Additionally, electrical conductivity was modeled as a function of tissue temperature according to the most widely cited definitions, giving 3 different ranges of electrical conductivity to evaluate in the model. Using average tissue dimensions, with a myocardium thickness of 3 mm, a pericardium thickness of 0.5 mm, and an esophageal thickness of 3 mm, with a lethal isotherm set at a conservative 44° C., almost all configurations of power and duration demonstrated the potential to damage esophageal tissue.

Part 2. Using the above-described model, the change in esophageal lesion formation and the depth of lesions (measured as percent transmurality) with an esophageal cooling device in place and operating at a temperature from 5° C. to 37° C. was assessed. Tissue parameters were set to average values obtained from existing literature, and energy settings were evaluated at 50 W for between 5 and 10 seconds, and at 90 W for a duration of 4 seconds.

Figure 24:
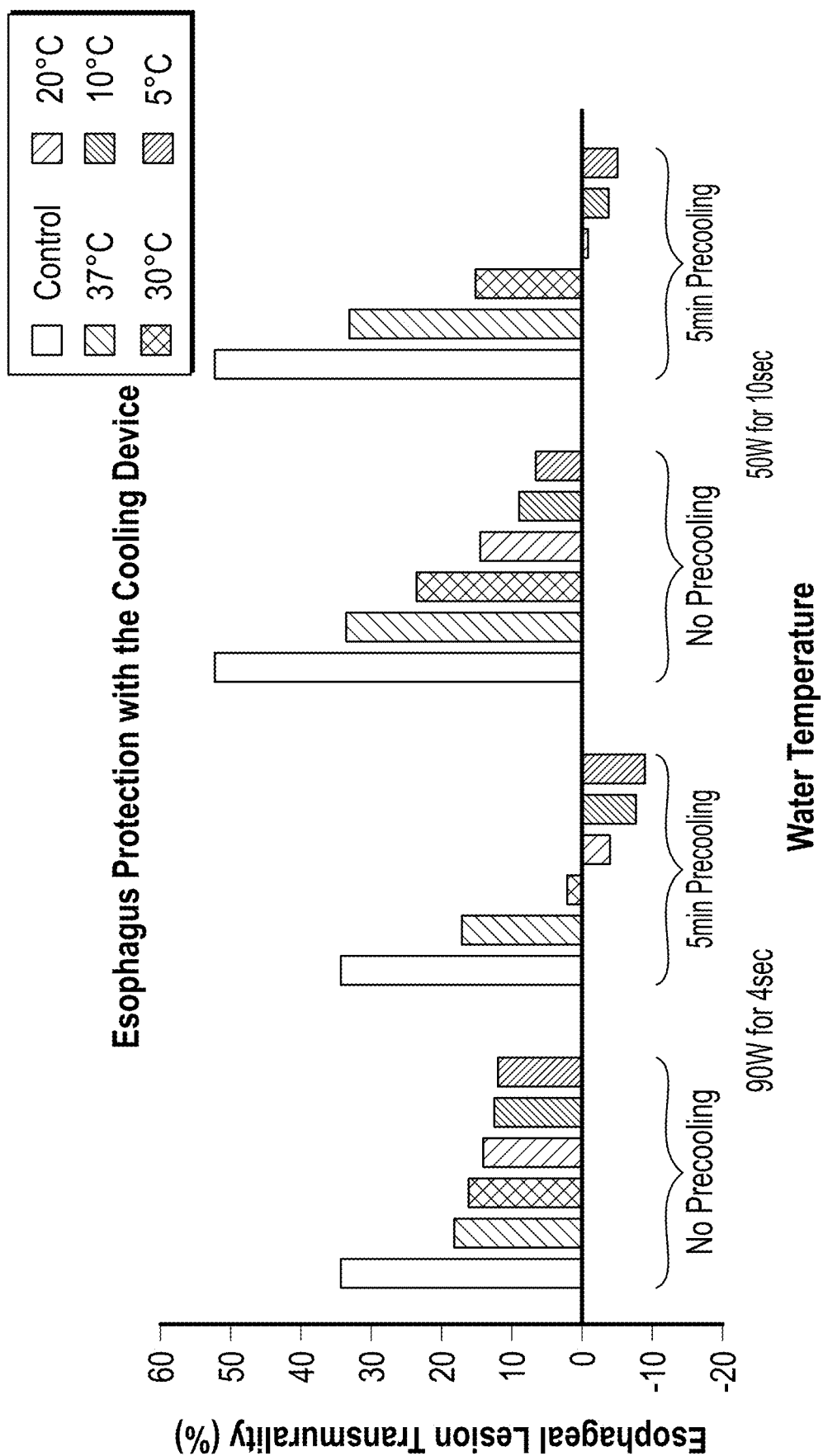
FIG. 24 is a bar graph showing the protective effect of esophageal cooling on esophageal lesion transmurality across a range of temperature settings, with and without 5 minutes of pre-cooling.

Esophageal injury as measured by percent transmurality was considerably higher at 50 W and 10 s duration than at 90 W of power with 4 s duration, although both settings showed potential for esophageal injury. The protective effect of an esophageal cooling device was evident for both cases, with a greater effect when using 50 W for 10 s (FIG. 24). Using a pre-cooling period of 5 minutes showed no significant impact when using 37° C. cooling water temperature, but showed a pronounced effect on esophageal lesion transmurality when using colder water temperatures. At the coldest device settings, using a 5 min pre-cooling period also reduced the transmurality of the intended atrial lesions.

Esophageal cooling with an esophageal cooling device shows protective effects against thermal injury during RF ablation using a range of high-power settings, including 90 W applied for 4 seconds. Adjusting the cooling power by adjusting the circulating water temperature in the device allows for a tailoring of the protective effects to operating conditions.

Example 6

Current technology used in the performance of cardiac ablation for the treatment of atrial fibrillation is limited by the fact that esophageal tissue is in contact with the left atrium, such that ablation against the posterior wall of the left atrium risks thermal damage (from heating or cooling, via radiofrequency [RF] or cryotherapy energy, respectively) to the anterior wall of the esophagus. This damage can range from mild erythema to complete ulceration, and can lead to the formation of an almost uniformly fatal atrioesophageal fistula.[1]

A metric used to quantify ablation performance uses the variables of contact force, power, and time of application to derive a number above which an intended lesion is more likely to be successful in maintaining electrical isolation.[2] Nevertheless, use of this index does not avoid the inadvertent, and dangerous, heating of esophageal tissue, with clinical study of this measure demonstrating 2 out of 40 patients inadequately treated due to overheating of the esophagus.[2]

The present disclosure demonstrates that cooling of esophageal tissue (or warming, in the case of cryo ablation) can be achieved, allowing greater ablation energy application, greater contact force, and or longer contact time (and hence achievement of higher ablation index parameters), while tuning the level of cooling using as described below to avoid unwanted cooling (or warming) of the intended region of impact in the atria.

This example describes a novel clinical model for evaluating optimal temperatures of circulating heat transfer medium for providing esophageal protection during a PVI procedure without adversely impacting the ability to achieve a durable lesion. This model reasonably predicted the effectiveness of esophageal protection across a variety of ablation parameters in a PVI procedure.

A mechanistic model was used to model the relationship between thermal protection of esophageal tissue, the adjustable parameters of the PVI procedure, and the relatively non-adjustable clinical values obtained from imaging studies.

A Performance Derivative (PD) was derived from the adjustable parameters of ablation and the non-adjustable clinical values obtained from imaging studies as follows:

$$\frac{(P*CF*t)}{(AT*JD*ET)} * \frac{1}{T_p}$$

where P is power in Watts, CF is contact force in grams, t is time in seconds, AT is atrial thickness in mm, JD is interstitial distance in mm, ET is esophageal thickness in mm, and $T_p$ is the Thermal Protectivity, which is derived from the following:

$$\frac{Q}{T} * k$$

where Q is the flow rate of the heat transfer medium (L/hr), T is the temperature of the heat transfer medium (° C.), and k is the thermal conductivity of the material of esophageal heat transfer device.

T varies as shown in the following tables for different ablation conditions and average clinical parameters (i.e., atrial thickness of about 3 mm, esophageal thickness of about 3 mm, and interstitial distance of about 2 mm) for an exemplary esophageal heat transfer device comprising silicone (k=0.4) and an exemplary chiller set at a flow rate of 60 L/h.

In Table 6, a target of value of PD approximately 500 was assumed to provide optimal lesion formation in the intended region of the atria, while protecting esophageal tissue from damage.

| Power (W) | Contact Force (g) | Time (sec) | T(° C.) |
|---|---|---|---|
| 30 | 10 | 40 | 18 |
| 30 | 15 | 30 | 16 |
| 30 | 20 | 20 | 18 |
| 30 | 30 | 15 | 16 |
| 30 | 40 | 10 | 18 |
| 50 | 10 | 40 | 11 |
| 50 | 15 | 30 | 10 |
| 50 | 20 | 20 | 11 |
| 50 | 30 | 15 | 10 |
| 50 | 40 | 10 | 11 |

In Table 7, a target of value of PD approximately 250 was assumed to provide optimal lesion formation in the intended region of the atria, while protecting esophageal tissue from damage.

| Power (W) | Contact Force (g) | Time (sec) | T(° C.) |
|---|---|---|---|
| 30 | 10 | 40 | 9 |
| 30 | 15 | 30 | 8 |
| 30 | 20 | 20 | 9 |
| 30 | 30 | 15 | 8 |
| 30 | 40 | 10 | 9 |
| 50 | 10 | 40 | 5 |
| 50 | 15 | 30 | 5 |
| 50 | 20 | 20 | 5 |
| 50 | 30 | 15 | 5 |
| 50 | 40 | 10 | 5 |

In Table 8, a target of value of PD approximately 100 was assumed to provide optimal lesion formation in the intended region of the atria, while protecting esophageal tissue from damage.

| Power (W) | Contact Force (g) | Time (sec) | T(° C.) |
|---|---|---|---|
| 10 | 15 | 10 | 29 |
| 20 | 15 | 10 | 14 |
| 30 | 15 | 10 | 10 |
| 40 | 15 | 10 | 7 |
| 50 | 15 | 10 | 6 |
| 10 | 15 | 20 | 14 |
| 20 | 15 | 20 | 7 |
| 30 | 15 | 20 | 5 |
| 40 | 15 | 20 | 4 |
| 50 | 15 | 20 | 3 |
| 10 | 15 | 30 | 10 |
| 20 | 15 | 30 | 5 |
| 30 | 15 | 30 | 3 |
| 40 | 15 | 30 | 2 |
| 50 | 15 | 30 | 2 |

Example 7. Cryoballoon Ablation Case Report

A 68-year-old male with past medical history of hypertension and increasing episodes of paroxysmal atrial fibrillation presented for cryoballoon ablation. An esophageal heat transfer device circulating 42° C. water was placed in the esophagus after a single-sensor temperature probe. Ablations were performed with a Medtronic Arctic Front Advance Cardiac CryoAblation Catheter system.

Initial patient core temperature was measured at 36.3° C. via Foley catheter temperature sensor. Temperatures in the esophagus at each pulmonary vein cryoballoon application were as follows. Beginning with cryoablation at the left superior pulmonary vein, the initial esophageal temperature measured was 38.6° C. and reached a nadir of 36.4° C. during the cryoablation. At the left inferior pulmonary vein, beginning temperature was 38.5° C. and reached a low of 38.0° C. after two cycles of treatment. In the right superior pulmonary vein, initial esophageal temperature was 38.4° C., remained unchanged through two cycles, and ended at 38.5° C. Finally, in the right inferior pulmonary vein, initial esophageal temperature was 38.9° C. and reached a nadir of 38.8° C. throughout two cycles of treatment. Patient temperature at the end of the procedure was 36.0° C.

An esophageal heat transfer device prevented temperature decreases below 36.4° C. in the esophagus during cryoablation, and thereby avoided the need to stop treatment during the procedure. Avoidance of temperature nadirs near the recommended cutoff threshold, typically 25° C., may also limit potential impact of cryoablation on esophageal tissue.

Example 8. Clinical Study in Atrial Ablation

This study was a prospective, double-blind randomized controlled trial of patients undergoing AF ablation to evaluate if esophageal cooling using an exemplary esophageal heat transfer device limits the frequency and/or severity of thermal injury during catheter ablation.

Patients were randomized to have a catheter ablation procedure (1) with utilization of the esophageal heat transfer device (and without use of a temperature probe) or (2) using standard esophageal protection methods, which is an esophageal temperature probe, to measure for any temperature changes during application of ablation energy. In the experimental group, cooling was controlled by the procedural doctor, with temperatures set in the range of patient safety. In particular, in the experimental group cooling fluid was circulated at a temperature from 4 to 6° C. In the control group, if measured esophageal temperatures reached beyond 38° C. then ablation was halted in that area.

Within one week after the ablation procedure, a follow up upper GI endoscopy test was performed by an endoscopist to review for any ablation-related thermal injury. The endoscopist performing the follow up endoscopy test was be 'blinded' to the randomization of the trial participant, to minimize bias.

TABLE 9

| Patient | Group | Thermal Lesions | Comments |
|---|---|---|---|
| 1 | Cool | No | Normal |
| 2 | Cool | No | Normal |
| 3 | Cool | No | Normal |
| 5 | Cool | No | Normal |
| 7 | Cool | No | Normal |
| 10 | Cool | No | Normal |
| 4 | Control | No | Hiatus hernia 3 cm |
| 6 | Control | No | Barretts (COM2) |
| 8 | Control | No | Normal |
| 9 | Control | Yes | Esophageal erosion; gastric ulcer |
| 11 | Control | No | Normal |
| 12 | Control | No | Normal |
| 13 | Control | No | Normal |
| 14 | Control | No | Normal |
| 15 | Control | No | Hiatus hernia 3 cm |
| 16 | Control | Yes | Linear erythema |
| 17 | Control | No | Normal |
| 18 | Control | No | Normal |
| 19 | Control | Yes | Submucosal bleed |
| 20 | Control | Yes | Two erosions |

An esophageal heat transfer device prevented thermal lesions and damage to esophageal tissue during atrial ablation. The results demonstrate that LET monitoring can be safely avoided by esophageal cooling using an exemplary esophageal heat transfer device. Moreover, avoiding LET monitoring and possible interruptions and/or stoppages to ablation treatment during the procedure may result in reduced procedure time.

In this application, the use of the disjunctive is intended to include the conjunctive. The use of definite or indefinite articles is not intended to indicate cardinality. In particular, a reference to "the" object or "a" and "an" object is intended to denote also one of a possible plurality of such objects. Further, the conjunction "or" may be used to convey features that are simultaneously present instead of mutually exclusive alternatives. In other words, the conjunction "or" should be understood to include "and/or". The terms "includes," "including," and "include" are inclusive and have the same scope as "comprises," "comprising," and "comprise" respectively.

The above-described embodiments, and particularly any "preferred" embodiments, are possible examples of implementations and merely set forth for a clear understanding of the principles of the invention. Many variations and modifications may be made to the above-described embodiment(s) without substantially departing from the spirit and principles of the techniques described herein. All modifications are intended to be included herein within the scope of this disclosure and protected by the following claims.

The above-described embodiments, and particularly any "preferred" embodiments, are possible examples of implementations and merely set forth for a clear understanding of the principles of the invention. Many variations and modifications may be made to the above-described embodiment(s) without substantially departing from the spirit and principles of the techniques described herein. All modifications are intended to be included herein within the scope of this disclosure and protected by the following claims.

The following references are incorporated by reference in their entirety:

Tzou W S, et al., J Cardiovasc Electrophysiol 2013, 24(9): 965-967.
Nair G M, et al., Can J Cardiol 2014, 30(4):388-395.
Liu E, et al., J Interv Card Electrophysiol 2012, 35(1):35-44.
Scanavacca M, Arquivos brasileiros de cardiologia 2016, 106(5):354-357.
Tschabrunn C M, et al., Europace 2015, 17(6):891-897.
Calkins H, et al., Journal of arrhythmia 2017, 33(5):369-409.
Halm U, et al., Am J Gastroenterol 2010, 105(3):551-556.
Knopp H, et al., Heart Rhythm, 11(4):574-578.
Leite L R, et al., Circ Arrhythm Electrophysiol 2011, 4(2): 149-156.
Carroll B J, C et al., J Cardiovasc Electrophysiol 2013, 24(9):958-964.
Hornero F, et al., J Thorac Cardiovasc Surg 2006, 132(1): 212-213; author reply 213-214.
Deneke T, et al., J Cardiovasc Electrophysiol 2011, 22(3): 255-261.
Berjano E J, et al., Phys Med Biol 2005, 50(20):N269-279.
Lequerica I L, et al., J Cardiovasc Electrophysiol 2008, 19(11):1188-1193.
Lequerica I L, et al., Phys Med Biol 2008, 53(4):N25-34.
Arruda M S, et al., J Cardiovasc Electrophysiol 2009, 20(11):1272-1278.
Tsuchiya T, et al., J Cardiovasc Electrophysiol 2007, 18(2): 145-150.
Scanavacca M I, et al., In: ESC Congress 2007, 1-5 September. vol. 28. Vienna, Austria; 2007: 156.
Kuwahara T, et al., Europace 2014, 16(6):834-839.
Sohara H, et al., J Cardiovasc Electrophysiol 2014, 25(7): 686-692.
Khan I, Ha et al., Ther Hypothermia Temp Manag 2017.
Kalasbail P, et al., Anesthesia & Analgesia 2018,
Goury A, et al., Resuscitation 2017, 121:54-61.
Hegazy A F, et al., Heart & Lung: The Journal of Acute and Critical Care 2017, 46(3):143-148.
Markota A, et al., The American Journal of Emergency Medicine 2016, 34(4):741-745.
Williams D, et al., Case Reports in Anesthesiology 2016, 2016:6.
Naiman M, et al., Expert Rev Med Devices 2016, 13(5): 423-433.
Naiman M I, et al., JoVE 2017(129):e56579.
Kapur S, et al., Circulation Sep. 26, 2017; 136:1247-1255.
Das M, et al., Europace May 1, 2017; 19:775-783.

The invention claimed is:

1. A method for achieving a durable atrial lesion and preventing or reducing the risk of thermal injury to esophageal tissue in a patient undergoing a cardiac tissue ablation procedure, the method comprising:
orally or nasally inserting an esophageal heat transfer device into the patient, wherein the heat transfer device includes a heat transfer region and one or more lumens configured to provide a heat transfer fluid to the heat transfer region and to remove the heat transfer fluid from the heat transfer region;
positioning the heat transfer region in thermal contact with esophageal tissue susceptible to damage during the cardiac tissue ablation procedure;
selecting a temperature setting for the heat transfer fluid, wherein the temperature setting is from about 0° C. to about 10° C.;
circulating the heat transfer fluid through the one or more lumens at the selected temperature setting to maintain a target temperature of the esophageal tissue susceptible to damage; and performing the cardiac tissue ablation procedure;
wherein the method achieves a durable atrial lesion while simultaneously protecting esophageal tissue during the cardiac tissue ablation procedure.

2. The method of claim 1, further comprising: adjusting, via a controller, a fluid source to provide the fluid to the esophageal heat transfer device in accordance with the temperature setting.

3. The method of claim 1, further comprising: collecting data via one or more sensing elements of the esophageal heat transfer device.

4. The method of claim 3, wherein the one or more sensing elements includes a temperature sensor or a location sensing element.

5. The method of claim 1, wherein the cardiac tissue ablation procedure is a radiofrequency ablation procedure.

6. The method of claim 1, wherein the method does not comprise luminal esophageal temperature (LET) monitoring.

7. The method of claim 5, further comprising: improving an outcome in the patient undergoing the radiofrequency ablation procedure.

8. The method of claim 7, wherein the outcome is at least one of achievement of a durable lesion on a posterior segment of an atrial wall; freedom from any symptomatic atrial arrhythmia (atrial fibrillation, atrial flutter, atrial tachycardia) 12 months post-RF ablation procedure; or reduction in amount and/or severity of damage to esophageal tissue relative to performing the RF ablation procedure without such temperature management.

9. The method of claim 5, wherein the radiofrequency ablation procedure comprises application of ablation energy to a posterior atrial wall segment of the patient and a target minimum Ablation Index ($AI_{min}$) value of from 300 to 550 on the posterior atrial wall segment.

10. The method of claim 1, wherein the esophageal heat transfer device further comprises a device-location sensing element.

11. The method of claim 10, wherein the device-location sensing element includes a fiducial marker detectable by a mapping and/or imaging system.

12. The method of claim 10, wherein the device-location sensing element includes one or more magnetic field sensors.

13. The method of claim 12, wherein the one or more magnetic field sensors create a signal in response to a magnetic field emitted by a magnetic field emitter.

14. The method of claim 10, wherein the device-location sensing element includes a tri-axial sensor.

15. The method of claim 14, wherein the tri-axial sensor includes three orthogonally configured coils.

* * * * *